(12) United States Patent
Teranishi et al.

(10) Patent No.: US 10,781,177 B2
(45) Date of Patent: Sep. 22, 2020

(54) PYRIDINE COMPOUND AND USE THEREOF

(71) Applicant: Nippon Soda Co., Ltd., Chiyoda-ku, Tokyo (JP)

(72) Inventors: Takaaki Teranishi, Odawara (JP); Shinya Uesusuki, Odawara (JP); Jun Iwata, Odawara (JP); Takuya Kamada, Odawara (JP); Youhei Munei, Odawara (JP); Satoshi Nishimura, Haibara-gun (JP); Hiroki Inoue, Tokyo (JP); Tetsuya Tanaka, Odawara (JP); Yuka Nakamura, Odawara (JP); Yusuke Fukushima, Odawara (JP); Tomomi Kobayashi, Odawara (JP); Shinya Koubori, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 16/080,494

(22) PCT Filed: Mar. 9, 2017

(86) PCT No.: PCT/JP2017/009536
§ 371 (c)(1),
(2) Date: Aug. 28, 2018

(87) PCT Pub. No.: WO2017/155052
PCT Pub. Date: Sep. 14, 2017

(65) Prior Publication Data
US 2019/0071403 A1 Mar. 7, 2019

(30) Foreign Application Priority Data

Mar. 9, 2016 (JP) ................................ 2016-046046

(51) Int. Cl.
| | | |
|---|---|---|
| *C07D 213/69* | (2006.01) | |
| *C07D 417/06* | (2006.01) | |
| *A01N 43/80* | (2006.01) | |
| *A01N 43/82* | (2006.01) | |
| *A01N 47/06* | (2006.01) | |
| *C07D 211/40* | (2006.01) | |
| *C07D 213/68* | (2006.01) | |
| *C07D 213/74* | (2006.01) | |
| *C07D 213/79* | (2006.01) | |

(Continued)

(52) U.S. Cl.
CPC ........... *C07D 213/69* (2013.01); *A01N 43/40* (2013.01); *A01N 43/80* (2013.01); *A01N 43/82* (2013.01); *A01N 47/06* (2013.01); *C07D 211/40* (2013.01); *C07D 213/68* (2013.01); *C07D 213/74* (2013.01); *C07D 213/79* (2013.01); *C07D 213/84* (2013.01); *C07D 213/89* (2013.01); *C07D 401/06* (2013.01); *C07D 405/06* (2013.01); *C07D 409/06* (2013.01); *C07D 413/06* (2013.01); *C07D 417/06* (2013.01)

(58) Field of Classification Search
CPC .. C07D 417/06; C07D 413/06; C07D 409/06; C07D 405/06; C07D 401/06; C07D 213/89; C07D 213/84; C07D 213/79; C07D 213/74; C07D 213/68; C07D 211/40; C07D 213/69; A01N 47/06; A01N 43/82; A01N 43/80; A01N 43/40
See application file for complete search history.

(56) References Cited

U.S. PATENT DOCUMENTS

| | | |
|---|---|---|
| 6,537,948 B1 | 3/2003 | Tohyama et al. |
| 2003/0216444 A1 | 11/2003 | Nishide et al. |

(Continued)

FOREIGN PATENT DOCUMENTS

| | | |
|---|---|---|
| AR | 083609 A1 | 3/2013 |
| DE | 19917160 A1 | 10/2000 |

(Continued)

OTHER PUBLICATIONS

International Search Report dated Jun. 13, 2017, in PCT/JP2017/009536.
Comins et al., "Ortho Lithiation of 2-, 3-, and 4-Methoxypyridines," Tetrahedron Letters, 1988, 29(7):773-776.
Chung et al., "New 4-Hydroxypyridine and 4-Hydroxyquinoline Derivatives as Inhibitors of NADH-ubiquinone Reductase in the Respiratory Chain," Zeitschrift fuer Naturforschung, C: Journal of Biosciences, 1989, 44(7-8):609-616.

(Continued)

*Primary Examiner* — Ali Soroush
*Assistant Examiner* — Danielle Sullivan
(74) *Attorney, Agent, or Firm* — Foley & Lardner LLP

(57) ABSTRACT

The present invention provides a compound represented by formula (I) (in the formula, $R^1$ to $R^4$ each represent a hydrogen atom, an unsubstituted or $G^1$-substituted C1-6 alkyl group or the like, A represents an oxygen atom or the like, Cy represents a C6-10 aryl group or the like), an N-oxide compound thereof, a tautomer or salt thereof. The present invention also provides an agricultural and horticultural fungicide, harmful organism control agent and insecticidal/acaricidal agent containing at least one compound selected from the group consisting of a compound represented by formula (I), a tautomer and salt thereof, as an active ingredient.

(I)

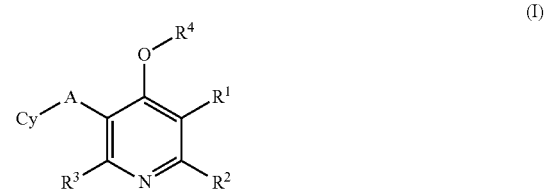

3 Claims, No Drawings

(51) Int. Cl.
| | |
|---|---|
| C07D 213/84 | (2006.01) |
| C07D 213/89 | (2006.01) |
| C07D 401/06 | (2006.01) |
| C07D 405/06 | (2006.01) |
| C07D 409/06 | (2006.01) |
| C07D 413/06 | (2006.01) |
| A01N 43/40 | (2006.01) |

(56) References Cited

U.S. PATENT DOCUMENTS

| | | |
|---|---|---|
| 2004/0266835 A1 | 12/2004 | Omura et al. |
| 2006/0089390 A1 | 4/2006 | Nishide et al. |
| 2006/0094878 A1 | 5/2006 | Peterson et al. |
| 2009/0259046 A1 | 10/2009 | Hamamoto et al. |
| 2009/0312383 A1 | 12/2009 | Aso et al. |
| 2009/0318694 A1 | 12/2009 | Hamamoto et al. |
| 2012/0010183 A1 | 1/2012 | Bell et al. |

FOREIGN PATENT DOCUMENTS

| | | | |
|---|---|---|---|
| EP | 0245230 A1 | | 11/1987 |
| EP | 0284174 A1 | | 9/1988 |
| EP | 1254904 A1 | | 11/2002 |
| JP | 62-267266 A | | 11/1987 |
| JP | 63-253069 A | | 10/1988 |
| JP | 07-500321 A | | 1/1995 |
| JP | 08198719 A | * | 8/1996 |
| JP | 08-283246 A | | 10/1996 |
| JP | 2001-270867 A | | 10/2001 |
| JP | 2001-270883 A | | 10/2001 |
| JP | 2002-155061 A | | 5/2002 |
| JP | 2002-356474 A | | 12/2002 |
| JP | 2004-051628 A | | 2/2004 |
| JP | 2006-117651 A | | 5/2006 |
| JP | 2008-518918 A | | 6/2008 |
| JP | 2008-539247 A | | 11/2008 |
| JP | 2013-532184 A | | 8/2013 |
| WO | WO 93/07146 A1 | | 4/1993 |
| WO | WO 99/41237 A1 | | 8/1999 |
| WO | WO 00/15616 A1 | | 3/2000 |
| WO | WO 03/103667 A1 | | 12/2003 |
| WO | WO 2004/039155 A1 | | 5/2004 |
| WO | WO 2006/137389 A1 | | 12/2006 |
| WO | WO 2007/040280 A1 | | 4/2007 |
| WO | WO 2007/040282 A1 | | 4/2007 |
| WO | WO 2007/086584 A1 | | 8/2007 |
| WO | WO 2011/014008 A2 | | 2/2011 |
| WO | WO 2016/039048 A1 | | 3/2016 |

OTHER PUBLICATIONS

Schroeder et al., "Neuritogenic Militarinone-Inspired 4-Hydroxypyridones Target the Stress Pathway Kinase MAP4K4," Angew. Chem. Int. Ed., 2015, 54(42):12398-12403.

Selby et al., "Synthetic atpenin analogs: Potent mitochondrial inhibitors of mammalian and fungal succinate-ubiquinone oxidoreductase," Bioorganic & Medicinal Chemistry Letters, 2010, 20(5):1665-1668.

Trecourt et al., "New Synthesis of Orelline by Metalation of Methoxypyridines," Tetrahedron, 1993, 49(37):8373-8380.

Trecourt et al., "Total Synthesis of (±)-Atpenin B. An Original "Clockwise" Functionalization of 2-chloropyridine," J. Org. Chem., 1994, 59(21):6173-6178.

Trecourt et al., "First Synthesis of (±)-Harzianopyridone by Metalation of Polysubstituted O-Pyridylcarbamates," J. Heterocyclic Chem., 1995, 32(4):1117-1124.

Yeates et al., "Synthesis and Structure-Activity Relationships of 4-Pyridones as Potential Antimalarials," J. Med. Chem., 2008, 51:2845-2852.

Supplementary Partial European Search Report dated Oct. 10, 2019, in EP 17763392.2.

Office Action dated Jun. 9, 2020 in JP 2018-504595, with English translation.

Chemical Abstract, 2014, AN 2014_1100201, DN 161:111393, AR 083609A1 (Mar. 6, 2013), RN 1613468-72-6, 2 pages.

Chi et al., "One-Pot Synthesis of Mannich Base Using Hydroxy Aromatic Rings and Secondary Amines," Bull. Korean Chem. Soc., 1999, 20(8):973-976.

Miki et al., "Synthesis of 3-methoxyellipticine and ellipticine by Friedel-Crafts reaction of indole-2,3dicarboxylic anhydride and selective demethylation," Heterocycles, 2005, 65(11):2693-2703.

Trecourt et al., "Synthesis of Xanthones and Thioxanthones having Two Heteroaromatic Rings," J. Chem. Research, 1982, 3:76-77.

* cited by examiner

PYRIDINE COMPOUND AND USE THEREOF

TECHNICAL FIELD

The present invention relates to a pyridine compound and use thereof such as agricultural and horticultural fungicides, harmful organism control agents, insecticidal agents or acaricidal agents, or the like.

This application is a National Stage application of PCT/JP2017/009536, filed Mar. 9, 2017, which claims priority from Japanese Patent Application No. 2016-046046, filed Mar. 9, 2016, the content of which is incorporated herein by reference.

BACKGROUND ART

In cultivation of agricultural and horticultural crops, a large number of control agents for crop diseases have been proposed. Most of those proposed control agents are not always satisfactory because the controlling effect thereof is insufficient, the use thereof is restricted due to the emergence of drug-resistant pathogenic bacteria, phytotoxicity or pollution to plants occurs, or the toxicity to livestocks and fish and the environmental impact were great. Therefore, an emergence of a control agent capable of being safely used without such disadvantages is strongly expected.

Patent Document 1 discloses a compound represented by formula (1) or formula (2). According to Patent Document 1, this compound seems to be useful as a complex II inhibitor of an electron transfer system.

[Chemical formula 1]

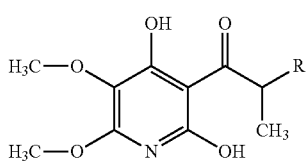

(1)

[Chemical formula 2]

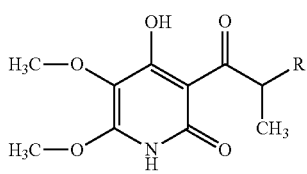

(2)

Further, Non-Patent Document 1 discloses a compound represented by formula (3). According to Non-Patent Document 1, this compound seems to be useful as an anti-malarial agent.

[Chemical formula 3]

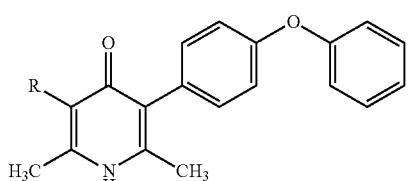

(3)

R: CF$_3$, OMe, H, Cl, Br

In addition, Non-Patent Document 2 discloses a compound represented by formula (4). According to Non-Patent Document 2, this compound seems to have an inhibitory activity of complex II of mammalian and fungi.

[Chemical formula 4]

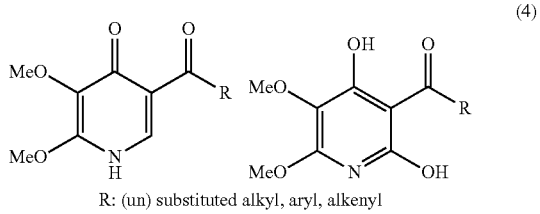

(4)

R: (un) substituted alkyl, aryl, alkenyl

PRIOR ART LITERATURE

Patent Documents

Patent document 1: WO 2003/103667 A

Non-Patent Document

Non-patent document 1: J. Med. Chem. 2008, 51, 2845-2852
Non-patent document 2: Bioorg. Med. Chem. Lett. 2010, 20, 1665-1668

DISCLOSURE OF INVENTION

Problems to be Solved by the Invention

An object of the present invention is to provide a novel pyridine compound, an agricultural and horticultural fungicide, a harmful organism control agent, and an insecticidal or acaricidal agent.

Means for Solving the Problems

As a result of studies to solve the above problems, the present invention including the following aspects has been completed.

[1] A pyridine compound represented by formula (I), an N-oxide compound thereof, or a tautomer or salt thereof.

[Chemical formula 5]

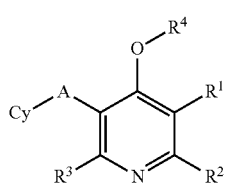

(I)

In formula (I), R$^1$ represents a hydrogen atom, an unsubstituted or G$^1$-substituted C1-6 alkyl group, an unsubstituted or G$^1$-substituted C2-6 alkenyl group, an unsubstituted or G$^1$-substituted C1-6 alkoxy group, an unsubstituted or G$^1$-substituted C1-6 alkoxycarbonyl group, an unsubstituted or G$^1$-substituted C1-6 alkylthio group, an unsubstituted or G$^1$-substituted C1-6 alkylaminocarbonyl group, an unsubstituted or G$^2$-substituted C6-10 aryl group, a cyano group or a halogeno group.

In formula (I), $R^2$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, an unsubstituted or $G^1$-substituted C1-6 alkoxy group, a formyloxy group, an unsubstituted or $G^1$-substituted C1-6 alkylcarbonyloxy group, an unsubstituted or $G^2$-substituted C6-10 aryl group, an (unsubstituted or $G^1$-substituted C1-6 alkoxyimino)-C1-6 alkyl group, an unsubstituted or $G^2$-substituted 3- to 10-membered heterocyclyl C1-6 alkyl group, a cyano group or a halogeno group.

In formula (I), $R^3$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, an unsubstituted or $G^1$-substituted C1-6 alkoxy group, an unsubstituted or $G^1$-substituted C1-6 alkylcarbonyl group, an unsubstituted or $G^1$-substituted C1-6 alkoxycarbonyl group, a carboxyl group, a formyl group, a formyloxy group, an unsubstituted or $G^1$-substituted C1-6 alkylcarbonyloxy group, an unsubstituted or $G^2$-substituted C6-10 aryl group, an unsubstituted or $G^2$-substituted 3- to 10-membered heterocyclyl group, an (unsubstituted or $G^1$-substituted C1-6 alkoxyimino)-C1-6 alkyl group, an unsubstituted or $G^1$-substituted mono C1-6 alkylamino group, an unsubstituted or $G^1$-substituted di C1-6 alkylamino group, a cyano group or a halogeno group.

In formula (I), $R^4$ represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl C1-6 alkyl group, an unsubstituted or $G^2$-substituted 3- to 10-membered heterocyclyl C1-6 alkyl group, a formyl group, an unsubstituted or $G^1$-substituted C1-6 alkylcarbonyl group, an unsubstituted or $G^2$-substituted C3-8 cycloalkylcarbonyl group, an unsubstituted or $G^1$-substituted C2-6 alkenylcarbonyl group, an unsubstituted or $G^2$-substituted C6-10 arylcarbonyl group, an unsubstituted or $G^1$-substituted C1-6 alkoxycarbonyl group, an unsubstituted or $G^1$-substituted C2-6 alkenyloxycarbonyl group, an unsubstituted or $G^1$-substituted C1-6 alkylsulfonyl group, an unsubstituted or $G^1$-substituted C1-6 alkylaminocarbonyl group, an unsubstituted or $G^1$-substituted (C1-6 alkylthio) carbonyl group, an unsubstituted or $G^1$-substituted C1-6 alkylamino (thiocarbonyl) group or an organic group represented by formula (II).

[Chemical formula 6]

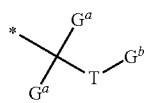

(II)

In formula (II), * represents bonding site.

In formula (II), each $G^a$ independently represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, or an unsubstituted or $G^2$-substituted C6-10 aryl group.

In formula (II), $G^b$ represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl group, or an unsubstituted or $G^2$-substituted 3- to 10-membered heterocyclyl group.

In formula (II), T represents an oxygen atom, an oxycarbonyl group, a carbonyloxy group, an oxycarbonyloxy group, a sulfur atom, a (thio) carbonyl group, a carbonyl (thio) group, a (thio) carbonyloxy group, an oxycarbonyl (thio) group or a divalent group represented by —O—C(=O)—N($G^b$)-.

In formula (I), A represents an oxygen atom or a divalent organic group represented by formula (III).

[Chemical formula 7]

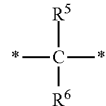

(III)

In formula (III), * represents bonding site.

In formula (III), $R^5$ and $R^6$ each independently represent a hydrogen atom, an unsubstituted or $G^1$-substituted C1-6 alkyl group, an unsubstituted or $G^1$-substituted C1-6 alkoxy group, an unsubstituted or $G^2$-substituted C6-10 aryloxy group, an unsubstituted or $G^1$-substituted alkoxycarbonyloxy group, a halogeno group, a hydroxyl group. $R^5$ and $R^6$ may bond to form a 3- to 6-membered ring together with the carbon atom to which $R^5$ and $R^6$ are bonded.

In formula (I), Cy represents an unsubstituted or $G^2$-substituted C6-10 aryl group, a $G^2$-substituted C3-8 cycloalkyl group, an unsubstituted or $G^2$-substituted 3- to 10-membered heterocyclyl group or a 13-membered heteroaryl group.

$G^1$ represents a hydroxyl group, a C1-6 alkoxy group, a C1-6 alkoxy C1-6 alkoxy group, a C1-6 alkoxycarbonyl group, a formyloxy group, a C1-6 alkylcarbonyloxy group, a C1-6 alkoxycarbonyloxy group, a mono C1-6 alkoxycarbonylamino group, a cyano group, an amino group or a halogeno group. When there are two or more $G^1$-substituted groups, such $G^1$s may be the same as or different from each other.

$G^2$ represents an unsubstituted or $G^{21}$-substituted C1-8 alkyl group, an unsubstituted or $G^{21}$-substituted C2-6 alkenyl group, an unsubstituted or $G^{21}$-substituted C2-6 alkynyl group, a hydroxyl group, an unsubstituted or $G^{21}$-substituted C1-6 alkoxy group, a formyl group, an unsubstituted or $G^{21}$-substituted C1-6 alkylcarbonyl group, an unsubstituted or $G^{21}$-substituted C1-6 alkoxycarbonyl group, a formyloxy group, an unsubstituted or $G^{21}$-substituted C1-6 alkylcarbonyloxy group, a formylamino group, an unsubstituted or $G^{21}$-substituted mono C1-6 alkylcarbonylamino group, an unsubstituted or $G^{21}$-substituted N—(C1-6 alkylcarbonyl)-N—(C1-6 alkyl) amino group, an unsubstituted or $G^{21}$-substituted N—(C1-6 alkylcarbonyl)-N—(C1-6 alkoxycarbonyl) amino group, an unsubstituted or $G^{21}$-substituted C1-6 alkoxycarbonyloxy group, an unsubstituted or $G^{21}$-substituted mono C1-6 alkoxycarbonylamino group, an unsubstituted or $G^{22}$-substituted C3-8 cycloalkyl group, an unsubstituted or $G^{22}$-substituted C3-8 cycloalkenyl group, an unsubstituted or $G^{22}$-substituted C 3-8 cycloalkylcarbonylaminocarbonyl group, an unsubstituted or $G^{22}$-substituted C6-10 aryl group, an unsubstituted or $G^{22}$-substituted C6-10 aryl C2-6 alkynyl group, an unsubstituted or $G^{22}$-substituted C6-10 aryloxy group, an unsubstituted or $G^{22}$- substituted 3- to 10-membered heterocyclyl group, a 13-membered heteroaryl group, an unsubstituted or $G^{22}$-substituted 3- to 10-membered heterocyclyloxy group, a mercapto group, an unsubstituted or $G^{21}$-substituted C1-6 alkylthio group, an unsubstituted or $G^{21}$-substituted C1-6 alkylsulfinyl group, an unsubstituted or $G^{21}$-substituted C1-6 alkylsulfonyl group, a pentafluorosulfanyl group, an unsubstituted or $G^{22}$-substituted unsubstituted C6-10 arylthio group, an unsubstituted or $G^{22}$-substituted C6-10 arylsulfinyl group, an unsubstituted or $G^{22}$-substituted C6-10 arylsulfonyl group, an unsubstituted or $G^{22}$-substituted monovalent C6-10 arylamino group, a dihydroboryl group, a nitro group, a cyano group, a halogeno group, an unsubstituted or $G^{21}$-substituted C1-6 alkylene group, an unsubstituted or $G^{21}$-substituted C1-6 alkylene monooxy group, an unsubstituted or $G^{21}$-substituted C1-6 alkylenedioxy group, a group represented by —$CR^a$=$NR^b$.

Here, $R^a$ represents a hydrogen atom, a C1-6 alkyl group, an unsubstituted or $G^{21}$-substituted mono C1-6 alkylcarbonylamino group, or an unsubstituted or $G^{22}$-substituted mono C 3-8 cycloalkylcarbonylamino group, $R^b$ represents an unsubstituted or $G^{21}$-substituted C1-6 alkoxy group, an unsubstituted or $G^{22}$-substituted C3-8 cycloalkoxy group, an unsubstituted or $G^{22}$-substituted phenoxy group, an unsubstituted or $G^{21}$-substituted mono C1-6 alkylamino group, or an unsubstituted or $G^{21}$-substituted di C1-6 alkylamino group. When there are two or more $G^2$-substituted groups, such $G^2$s may be the same as or different from each other.

$G^{21}$ represents a C1-6 alkoxy group, a C1-6 haloalkoxy group, a mono C1-6 alkylamino group, a di C1-6 alkylamino group, a mono (C1-6 alkoxy C1-6 alkylcarbonyl) amino group, an unsubstituted or $G^{211}$-substituted C6-10 aryl group, an unsubstituted or $G^{211}$-substituted C6-10 aryloxy group, an unsubstituted or $G^{211}$-substituted 3- to 10-membered heterocyclyl group, an unsubstituted or $G^{211}$-substituted 3- to 10-membered heterocyclyloxy group or a halogeno group. When there are two or more $G^{21}$-substituted groups, such $G^{21}$s may be the same as or different from each other.

$G^{211}$ represents a C1-6 alkyl group, a C1-6 haloalkyl group, a C1-6 alkoxy group, a C1-6 haloalkoxy group or a halogeno group. When there are two or more $G^{211}$-substituted groups, such $G^{211}$s may be the same as or different from each other.

$G^{22}$ represents an unsubstituted or hydroxyl-substituted C1-6 alkyl group, a C1-6 haloalkyl group, a C2-6 alkenyl group, a C2-6 haloalkenyl group, a C2-6 alkynyl group, a C1-6 alkoxy group, a C1-6 haloalkoxy group, a C1-6 alkylcarbonyl group, a mono C1-6 alkylamino group, a di C1-6 alkylamino group, a C1-6 alkylaminocarbonyl group, a C1-6 alkylthio group, a C1-6 haloalkylthio group, a C1-6 alkylsulfinyl group, a C1-6 haloalkylsulfinyl group, a C1-6 alkylsulfonyl group, a C1-6 haloalkylsulfonyl group, an unsubstituted or $G^{221}$-substituted C3-8 cycloalkyl group, an unsubstituted or $G^{221}$-substituted C3-8 cycloalkyl C1-6 alkyl group, an unsubstituted or $G^{221}$-substituted C6-10 aryl group, an unsubstituted or $G^{221}$-substituted 3- to 10-membered heterocyclyl group, an unsubstituted or $G^{221}$-substituted 3- to 10-membered heterocyclylcarbonyl group, a pentafluorosulfanyl group, a nitro group, a cyano group, a halogeno group, an oxo group, an unsubstituted or $G^{211}$-substituted C1-6 alkylenedioxy group or a group represented by —$CR^c$=$NOR^d$. Here, $R^c$ represents a C1-6 alkyl group, $R^d$ represents an unsubstituted or $G^{221}$-substituted C3-8 cycloalkyl group. When there are two or more $G^{22}$-substituted groups, such $G^{22}$s may be the same as or different from each other.

$G^{221}$ represents a C1-6 alkyl group, a C1-6 haloalkyl group, a C1-6 alkoxy group, a C1-6 haloalkoxy group, a mono C1-6 alkylamino group, a di C1-6 alkylamino group, a C6-10 aryl group or a halogeno group. When there are two or more $G^{221}$-substituted groups, such $G^{221}$s may be the same as or different from each other.

[2] An agricultural and horticultural fungicide including as an active ingredient at least one selected from the group consisting of the pyridine compound, the N-oxide compound thereof, and the tautomer and salt thereof according to [1].

[3] A harmful organism control agent including as an active ingredient at least one selected from the group consisting of the pyridine compound, the N-oxide compound thereof, and the tautomer and salt thereof according to [1].

[4] An insecticidal or acaricidal agent including as an active ingredient at least one selected from the group consisting of the pyridine compound, the N-oxide compound, and the tautomer and salt thereof according to [1].

[5] An ectoparasite control agent including as an active ingredient at least one selected from the group consisting of the pyridine compound, the N-oxide compound, and the tautomer and salt thereof according to [1].

Effects of the Invention

The pyridine compound according to the present invention has a harmful organism controlling effect, fungicidal effect, acaricidal and insecticidal effects, and the like, and does not cause phytotoxicity to plants, and is a novel compound having less toxicity to livestocks and fish and less environmental impact. In particular, it shows an excellent controlling effect against wheat disease. The pyridine compound according to the present invention is useful as an active ingredient of agricultural and horticultural fungicides, harmful organism control agents, and insecticidal or acaricidal agents.

BEST MODE FOR CARRYING OUT THE INVENTION

The pyridine compound according to the present invention is a pyridine compound represented by formula (I) (hereinafter may be referred to as a compound (I)), an N-oxide compound thereof, a tautomer of compound (I) or a salt of compound (I).

[Chemical formula 8]

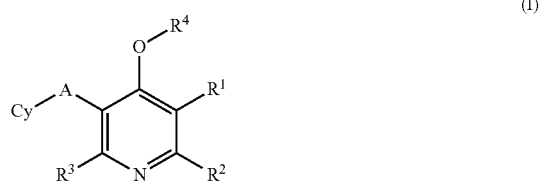

(I)

First, groups $G^1$ and $G^2$ which may be a substituent of the groups in formula (I) will be explained.

[$G^1$]

Substituent $G^1$ represents a hydroxyl group, a C1-6 alkoxy group, a C1-6 alkoxy C1-6 alkoxy group, a C1-6 alkoxycarbonyl group, a formyloxy group, a C1-6 alkylcarbonyloxy group, a C1-6 alkoxycarbonyloxy group, a mono C1-6 alkoxycarbonylamino group, a cyano group, an amino group or a halogeno group. When there are two or more $G^1$-substituted groups, such $G^1$s may be the same as or different from each other.

Examples of the C1-6 alkoxy group include a methoxy group, ethoxy group, n-propoxy group, n-butoxy group, n-pentyloxy group, n-hexyloxy group, i-propoxy group, i-butoxy group, s-butoxy group, t-butoxy group, i-hexyloxy group and the like.

Examples of the C1-6 alkoxy C1-6 alkoxy group include a methoxymethoxy group, 1-methoxyethoxy group, 2-methoxyethoxy group and the like.

Examples of the C1-6 alkoxycarbonyl group include a methoxycarbonyl group, ethoxycarbonyl group, n-propoxycarbonyl group, i-propoxycarbonyl group, t-butoxycarbonyl group and the like.

Examples of the C1-6 alkylcarbonyloxy group include an acetyloxy group, propionyloxy group, butyryloxy group and the like.

Examples of the C1-6 alkoxycarbonyloxy group include a methoxycarbonyloxy group, ethoxycarbonyloxy group, n-propoxycarbonyloxy group, i-propoxycarbonyloxy group, n-butoxycarbonyloxy group, t-butoxycarbonyloxy group and the like.

The mono C1-6 alkoxycarbonylamino group is the one in which an amino group is mono substituted with the aforementioned C1-6 alkoxycarbonyl group. Examples of the C1-6 alkoxycarbonylamino group include a methoxycarbonylamino group, ethoxycarbonylamino group, n-propoxycarbonylamino group, i-propoxycarbonylamino group, n-butoxycarbonylamino group, t-butoxycarbonylamino group and the like.

Examples of the halogeno group include a fluoro group, chloro group, bromo group and iodo group.

$G^1$ is preferably a hydroxyl group, a C1-6 alkoxy group or a halogeno group.

[$G^2$]

$G^2$ represents an unsubstituted or $G^{21}$-substituted C1-8 alkyl group, an unsubstituted or $G^{21}$-substituted C2-6 alkenyl group, an unsubstituted or $G^{21}$-substituted C2-6 alkynyl group, a hydroxyl group, an unsubstituted or $G^{21}$-substituted C1-6 alkoxy group, a formyl group, an unsubstituted or $G^{21}$-substituted C1-6 alkylcarbonyl group, an unsubstituted or $G^{21}$-substituted C1-6 alkoxycarbonyl group, a formyloxy group, an unsubstituted or $G^{21}$-substituted C1-6 alkylcarbonyloxy group, a formylamino group, an unsubstituted or $G^{21}$-substituted mono C1-6 alkylcarbonylamino group, an unsubstituted or $G^{21}$-substituted N—(C1-6 alkylcarbonyl)-N—(C1-6 alkyl) amino group, an unsubstituted or $G^{21}$-substituted N—(C1-6 alkylcarbonyl)-N—(C1-6 alkoxycarbonyl) amino group, an unsubstituted or $G^{21}$-substituted C1-6 alkoxycarbonyloxy group, an unsubstituted or $G^{21}$-substituted mono C1-6 alkoxycarbonylamino group, an unsubstituted or $G^{22}$-substituted C3-8 cycloalkyl group, an unsubstituted or $G^{22}$-substituted C3-8 cycloalkenyl group, an unsubstituted or $G^{22}$-substituted C 3-8 cycloalkylcarbonylaminocarbonyl group, an unsubstituted or $G^{22}$-substituted C6-10 aryl group, an unsubstituted or $G^{22}$-substituted C6-10 aryl C2-6 alkynyl group, an unsubstituted or $G^{22}$-substituted C6-10 aryloxy group, an unsubstituted or $G^{22}$-substituted 3- to 10-membered heterocyclyl group, a 13-membered heteroaryl group, an unsubstituted or $G^{22}$-substituted 3- to 10-membered heterocyclyloxy group, a mercapto group, an unsubstituted or $G^{21}$-substituted C1-6 alkylthio group, an unsubstituted or $G^{21}$-substituted C1-6 alkylsulfinyl group, an unsubstituted or $G^{21}$-substituted C1-6 alkylsulfonyl group, a pentafluorosulfanyl group, an unsubstituted or $G^{22}$-substituted unsubstituted C6-10 arylthio group, an unsubstituted or $G^{22}$-substituted C6-10 arylsulfinyl group, an unsubstituted or $G^{22}$-substituted C6-10 arylsulfonyl group, an unsubstituted or $G^{22}$-substituted monovalent C6-10 arylamino group, a dihydroboryl group, a nitro group, a cyano group, a halogeno group, an unsubstituted or $G^{21}$-substituted C1-6 alkylene group, an unsubstituted or $G^{21}$-substituted C1-6 alkylene monooxy group, an unsubstituted or $G^{21}$-substituted C1-6 alkylenedioxy group, or a group represented by —$CR^a$=$NR^b$.

Here, $R^a$ represents a hydrogen atom, a C1-6 alkyl group, an unsubstituted or $G^{21}$-substituted mono C1-6 alkylcarbonylamino group, or an unsubstituted or $G^{22}$-substituted mono C 3-8 cycloalkylcarbonylamino group, $R^b$ represents an unsubstituted or $G^{21}$-substituted C1-6 alkoxy group, an unsubstituted or $G^{22}$-substituted C3-8 cycloalkoxy group, an unsubstituted or $G^{22}$-substituted phenoxy group, an unsubstituted or $G^{21}$-substituted mono C1-6 alkylamino group, or an unsubstituted or $G^{21}$-substituted di C1-6 alkylamino group. When there are two or more $G^2$-substituted groups, such $G^2$s may be the same as or different from each other.

The C1-6 alkoxy group, C1-6 alkoxycarbonyl group, C1-6 alkylcarbonyloxy group, C1-6 alkoxycarbonyloxy group, mono C1-6 alkoxycarbonylamino group and halogeno group for substituent $G^2$ are as described above.

The C1-8 alkyl group may be a straight chain or a branched chain if it has 3 or more carbon atoms. Examples of the C1-6 alkyl group include a methyl group, ethyl group, n-propyl group, i-propyl group, n-butyl group, s-butyl group, i-butyl group, t-butyl group, n-pentyl group, n-hexyl group, i-pentyl group, neopentyl group, 2-methylbutyl group, 2,2-dimethylpropyl group, i-hexyl group, n-heptyl group, n-octyl group and the like.

Examples of the C2-6 alkenyl group include a vinyl group, 1-propenyl group, 2-propenyl group (allyl group), 1-butenyl group, 2-butenyl group, 3-butenyl group, 1-methylvinyl group (isopropenyl group), 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the C2-6 alkynyl group include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

The C1-6 alkylcarbonyl group is the one in which the aforementioned C1-6 alkyl group is bonded to a carbonyl group. Examples of the C1-6 alkylcarbonyl group include an acetyl group, a propionyl group, a butyryl group, isobutyryl group, pivaloyl group and the like.

The mono C1-6 alkylcarbonylamino group is the one in which an amino group is mono substituted with the aforementioned C1-6 alkylcarbonyl group. Examples of the mono C1-6 alkylcarbonylamino group include an acetylamino group, a propanoylamino group, a butyrylamino group, i-propylcarbonylamino group, 2,2-dimethylpropylcarbonylamino group and the like.

The N—(C1-6 alkylcarbonyl)-N—(C1-6 alkyl) amino group is the one in which an amino group is substituted with the aforementioned C1-6 alkyl group and C1-6 alkylcarbonyl group. Examples of the N—(C1-6 alkylcarbonyl)-N—(C1-6 alkyl) amino group include an N-(2,2-dimethylpropylcarbonyl)-N-methylamino group and the like.

The N—(C1-6 alkylcarbonyl)-N—(C1-6 alkoxycarbonyl) amino group is the one in which an amino group is substituted with the aforementioned C1-6 alkoxycarbonyl group and C1-6 alkylcarbonyl group. Examples of the N—(C1-6 alkylcarbonyl)-N—(C1-6 alkoxycarbonyl) amino group include an N-acetyl-N-methoxycarbonylamino group and the like.

Examples of the C3-8 cycloalkyl group include a cyclopropyl group, cyclobutyl group, cyclopentyl group, cyclohexyl group, cycloheptyl group, 2-adamantyl group and the like.

Examples of the C3-8 cycloalkenyl group include a cyclopropenyl group, cyclobutenyl group, cyclopentenyl group, cyclohexenyl group, cycloheptenyl group and the like.

Examples of the C3-8 cycloalkylcarbonylaminocarbonyl group include groups represented by the following formulas and the like. * represents bonding site.

[Chemical formula 9]

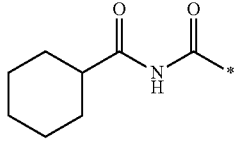

The C6-10 aryl group may be either a monocyclic ring or a polycyclic ring. The polycyclic aryl group may have any of a saturated alicyclic ring, unsaturated alicyclic ring and aromatic ring, provided that at least one ring is an aromatic ring. Examples of the C6-10 aryl group include a phenyl group, naphthyl group, azulenyl group, indenyl group, indanyl group, tetralinyl group and the like.

The C6-10 aryl C2-6 alkynyl group is the one in which the aforementioned C2-6 alkynyl group is substituted with the aforementioned C6-10 aryl group. Examples of the C6-10 aryl C2-6 alkynyl group include a phenylethynyl group and the like.

The C6-10 aryloxy group is the one in which a hydroxyl group is substituted with the aforementioned C6-10 aryl group. Examples of the C6-10 aryloxy group include a phenoxy group, naphthoxy group and the like.

The 3- to 10-membered heterocyclyl group is a cyclic group containing 1 to 4 hetero atoms selected from the group consisting of a nitrogen atom, oxygen atom and a sulfur atom as a constituent atom of the ring. The heterocyclyl group may be either a monocyclic ring or a polycyclic ring. The polycyclic heterocyclyl group may have any of a saturated alicyclic ring, unsaturated alicyclic ring and aromatic ring, provided that at least one ring is a heterocyclic ring. Examples of the 3- to 10-membered heterocyclyl group include a 3- to 10-membered saturated heterocyclyl group, 5- to 10-membered heteroaryl group, partially unsaturated 5- to 6-membered heterocyclyl group and the like.

Examples of the 3- to 10-membered saturated heterocyclyl group include an aziridinyl group, oxiranyl group, azetidinyl group, oxetanyl group, pyrrolidinyl group, tetrahydrofuranyl group, thiazolidinyl group, piperidyl group, piperazinyl group, morpholinyl group, tetrahydropyranyl group, dioxolanyl group, dioxanyl group, isoxazolidinyl group, 3-oxoisoxazolidinyl group, 4,4,5,5-tetramethyl-1,3,2-dioxaborolanyl group and the like.

Examples of the 5-membered heteroaryl group include a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group and the like.

Examples of the 6-membered heteroaryl group include a pyridyl group, pyrazinyl group, pyrimidinyl group, pyridanidyl group, triazinyl group and the like.

Examples of the partially unsaturated 5- to 6-membered heterocyclyl group include a dihydroisoxazolyl group and the like.

Examples of the 9-membered heteroaryl group include an indolyl group, isoindolyl group, benzofuranyl group, dihydrobenzofuranyl group, indazolyl group, benzoxazolyl group, benzoisoxazolyl group, benzothiazolyl group, benzoisothiazolyl group, pyridyl pyrazole group, triazolopyridyl group and the like.

Examples of the partially unsaturated 9-membered heterocyclyl group includes an indolinyl group, isoindolinyl group, 1,3-dioxoisoindolinyl group and the like.

Examples of the 10-membered heteroaryl group include a quinolinyl group, isoquinolinyl group, cinnolinyl group, phthalazinyl group, quinazolinyl group, quinoxalinyl group and the like.

Examples of the 13-membered heteroaryl group include a dibenzo [b, d] furanyl group, dibenzo [b, d] thiophenyl group and the like.

The 3- to 10-membered heterocyclyloxy group is the one in which a hydroxyl group is substituted with the aforementioned 3- to 10-membered heterocyclyl group. Examples of the 3- to 10-membered heterocyclyloxy group include a pyrazolyloxy group, pyridyloxy group and the like. The 3- to 10-membered heterocyclyloxy group is preferably a 5- to 6-membered heterocyclyloxy group.

The C1-6 alkylthio group is the one in which SH group is substituted with the aforementioned C1-6 alkyl group. Examples of the C1-6 alkylthio group include a methylthio group, ethylthio group, n-propylthio group, n-butylthio group, n-pentylthio group, n-hexylthio group, i-propylthio group, i-butylthio group and the like.

The C1-6 alkylsulfinyl group is the one in which a sulfinyl group is substituted with the aforementioned C1-6 alkyl group. Examples of the C1-6 alkylsulfinyl group include a methylsulfinyl group, ethylsulfinyl group, t-butylsulfinyl group and the like.

The C1-6 alkylsulfonyl group is the one in which a sulfonyl group is substituted with the aforementioned C1-6 alkyl group. Examples of the C1-6 alkylsulfonyl group include a methylsulfonyl group, ethylsulfonyl group, t-butylsulfonyl group and the like.

The C6-10 arylthio group is the one in which SH group is substituted with the aforementioned C6-10 aryl group. Examples of the C6-10 arylthio group include a phenylthio group, naphthylthio group and the like.

The C6-10 arylsulfinyl group is the one in which a sulfinyl group is substituted with the aforementioned C6-10 aryl group. Examples of the C6-10 arylsulfinyl group include a phenylsulfinyl group, naphthylsulfinyl group and the like.

The C6-10 arylsulfonyl group is the one in which a sulfonyl group is substituted with the aforementioned C 6-10 aryl group. Examples of the C6-10 arylsulfonyl group include a phenylsulfonyl group, naphthylsulfonyl group and the like.

The C6-10 arylamino group is the one in which an amino group is substituted with the aforementioned C6-10 aryl group. Examples of the C6-10 arylamino group include a phenylamino group and the like.

The C1-6 alkylene group is a divalent group formed by removing two hydrogen atoms in a C1-6 alkane. Examples of the C1-6 alkylene group include a methylene group, ethylene group (dimethylene group), trimethylene group, tetramethylene group, propane-1,2-diyl group (ie, propylene group) and the like. Examples of the C6-10 aryl group substituted with the C1-6 alkylene group represented by $G^2$ include a 2,3-dihydro-1H-indenyl group, 5,6,7,8-tetranaphthalenyl group and the like.

The C1-6 alkylene monooxy group is a divalent group formed by substituting one hydrogen atom in a C1-6 alkane with an oxy group. Examples of the C1-6 alkylene monooxy group include a methylene monooxy group (—CH$_2$O—), ethylene monooxy group (—CH$_2$CH$_2$O—), trimethylenemonooxy group (—CH$_2$CH$_2$CH$_2$O—) and the like. Examples of the C6-10 aryl group substituted with the C1-6 alkylene monooxy group represented by $G^2$ include a 2,3-dihydrobenzofuranyl group, chromanyl group and the like.

The C1-6 alkylenedioxy group is a divalent group formed by substituting two hydrogen atoms in the C1-6 alkane with an oxy group. Examples of the C1-6 alkylenedioxy group include a methylenedioxy group (—OCH$_2$O—), ethylenedioxy group (—OCH$_2$CH$_2$O—), trimethylenedioxy group and the like. Examples of the C6-10 aryl group substituted with the C1-6 alkylenedioxy group represented by $G^2$ include a 2,3-dihydro-benzo [1,4] dioxyl group, benzo [1,3] dioxolyl group and the like.

The C1-6 alkyl group and mono C1-6 alkylcarbonylamino group for $R^a$ in the group represented by formula: —CR$^a$═NR$^b$ are as described above.

Examples of the mono C3-8 cycloalkylcarbonylamino group for $R^a$ include a cyclopropylcarbonylamino group, cyclobutylcarbonylamino group, cyclopentylcarbonylamino group, cyclohexylcarbonylamino group and the like.

The C1-6 alkoxy group and C3-8 cycloalkoxy group for $R^b$ in the group represented by formula: —CR$^a$═NR$^b$ are as described above.

Examples of the mono C1-6 alkylamino group for $R^b$ include a methylamino group, ethylamino group and the like.

Examples of the di C1-6 alkylamino group for $R^b$ include a dimethylamino group, eiethylamino group and the like.

[$G^{21}$]

$G^{21}$ represents a C1-6 alkoxy group, a C1-6 haloalkoxy group, a mono C1-6 alkylamino group, a di C1-6 alkylamino group, a mono (C1-6 alkoxy C1-6 alkylcarbonyl) amino group, an unsubstituted or $G^{211}$-substituted C6-10 aryl group, an unsubstituted or $G^{211}$-substituted C6-10 aryloxy group, an unsubstituted or $G^{211}$-substituted 3- to 10-membered heterocyclyl group, an unsubstituted or $G^{211}$-substituted 3- to 10-membered heterocyclyloxy group or a halogeno group. When there are two or more $G^{21}$-substituted groups, such $G^{21}$s may be the same as or different from each other.

The C1-6 alkoxy group, C6-10 aryl group, mono C1-6 alkylamino group, di C1-6 alkylamino group, C6-10 aryloxy group, 3- to 10-membered heterocyclyl group, 3- to 10-membered heterocyclyloxy group and the halogeno group for substituent $G^{21}$ are as described above.

The C1-6 haloalkoxy group is the one in which the above described C1-6 alkoxy group is substituted with a halogeno group.

Examples of the C1-6 haloalkoxy group include a chloromethoxy group, dichloromethoxy group, difluoromethoxy group, trichloromethoxy group, trifluoromethoxy group, 1-fluoroethoxy group, 1,1-difluoroethoxy group, 2,2,2-trifluoroethoxy group, 1,1,2,2-tetrafluoroethoxy group, pentafluoroethoxy group, 2,2,3,4,4,4-hexafluoro-butoxy group, 1-bromo-1,1,2,2-tetrafluoroethoxy group and the like.

Examples of the mono (C1-6 alkoxy C1-6 alkylcarbonyl) amino group include a methoxymethylcarbonylamino group, ethoxymethylcarbonylamino group, 2-methoxyethylcarbonylamino group, 2-ethoxyethylcarbonylamino group and the like.

$G^{21}$ is preferably a halogeno group.

[$G^{211}$]

$G^{211}$ represents a C1-6 alkyl group, a C1-6 haloalkyl group, a C1-6 alkoxy group, a C1-6 haloalkoxy group or a halogeno group. When there are two or more $G^{211}$-substituted groups, such $G^{211}$s may be the same as or different from each other.

The C1-6 alkyl group, C1-6 alkoxy group, C1-6 haloalkoxy group and halogeno group for $G^{211}$ are as described above.

The C1-6 haloalkyl group is the one in which a C1-6 alkyl group is substituted with a halogeno group as described above. Examples of the C1-6 haloalkyl group include a fluoromethyl group, chloromethyl group, bromomethyl group, difluoromethyl group, dichloromethyl group, dibromomethyl group, trifluoromethyl group, trichloromethyl group, tribromomethyl group, 1-chloroethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, 2,4,6-trichlorohexyl group and the like.

$G^{211}$ is preferably a C1-6 alkyl group, and particularly preferably a methyl group.

[$G^{22}$]

$G^{22}$ represents an unsubstituted or hydroxyl-substituted C1-6 alkyl group, a C1-6 haloalkyl group, a C2-6 alkenyl group, a C2-6 haloalkenyl group, a C2-6 alkynyl group, a C1-6 alkoxy group, a C1-6 haloalkoxy group, a C1-6 alkylcarbonyl group, a mono C1-6 alkylamino group, a di C1-6 alkylamino group, a C1-6 alkylaminocarbonyl group, a C1-6 alkylthio group, a C1-6 haloalkylthio group, a C1-6 alkylsulfinyl group, a C1-6 haloalkylsulfinyl group, a C1-6 alkylsulfonyl group, a C1-6 haloalkylsulfonyl group, an unsubstituted or $G^{221}$-substituted C3-8 cycloalkyl group, an unsubstituted or $G^{221}$-substituted C3-8 cycloalkyl C1-6 alkyl group, an unsubstituted or $G^{221}$-substituted C 6-10 aryl group, an unsubstituted or $G^{221}$-substituted 3- to 10-membered heterocyclyl group, an unsubstituted or $G^{221}$-substituted 3- to 10-membered heterocyclylcarbonyl group, a pentafluorosulfanyl group, a nitro group, a cyano group, a halogeno group, an oxo group, an unsubstituted or $G^{211}$-substituted C1-6 alkylenedioxy group or a group represented by —CR$^c$═NOR$^d$. Here, R$^c$ represents a C1-6 alkyl group, R$^d$ represents an unsubstituted or $G^{221}$-substituted C3-8 cycloalkyl group. When there are two or more $G^{22}$-substituted groups, such $G^{22}$s may be the same as or different from each other.

The C1-6 alkyl group, C1-6 haloalkyl group, C2-6 alkenyl group, C2-6 alkynyl group, C1-6 alkoxy group, C1-6 haloalkoxy group, C1-6 alkylcarbonyl group, mono C1-6 alkylamino group, di C1-6 alkylamino group, C1-6 alkylthio group, C1-6 alkylsulfinyl group, C1-6 alkylsulfonyl group, C3-8 cycloalkyl group, C6-10 aryl group, 3- to 10-membered heterocyclyl group, halogeno group, C1-6 alkylenedioxy group for substituent $G^{22}$ are as described above.

The C2-6 haloalkenyl group is the one in which the above described C1-6 alkenyl group is substituted with a halogeno group. Examples of the C2-6 haloalkenyl group include a 2-chlorovinyl group, 2-bromovinyl group, 2-iodovinyl group, 1-fluoro-2-iodovinyl group, 2-chloro-1-propenyl group, 2-fluoro-1-butenyl group and the like.

Examples of the C3-8 cycloalkyl C1-6 alkyl group include a cyclopropylmethyl group, 2-cyclopropylethyl group, cyclopentylmethyl group, 2-cyclohexylethyl group, 2-cyclooctylethyl group and the like.

Examples of the C1-6 alkylaminocarbonyl group include a methylaminocarbonyl group, dimethylaminocarbonyl group, diethylaminocarbonyl group and the like.

The C1-6 haloalkylthio group is the one in which the above described C1-6 alkylthio group is substituted with a halogeno group. Examples of the C1-6 haloalkylthio group include a trifluoromethylthio group and the like.

The C1-6 haloalkylsulfinyl group is the one in which the above described C1-6 alkylsulfinyl group is substituted with a halogeno group. Examples of the C1-6 haloalkylsulfinyl group include a trifluoromethylsulfinyl group and the like.

The C1-6 haloalkylsulfonyl group is the one in which the above described C1-6 alkylsulfonyl group is substituted with a halogeno group. Examples of the C1-6 haloalkylsulfonyl group include a trifluoromethylsulfonyl group and the like.

The 3- to 10-membered heterocyclylcarbonyl group is the one in which a carbonyl group is substituted with the above described 3- to 10-membered heterocyclyl group. Examples of the 3- to 10-membered heterocyclylcarbonyl group include an azetidinylcarbonyl group, pyrrolidinyl carbonyl group, piperidinylcarbonyl group, morpholinylcarbonyl group, piperazinylcarbonyl group, 1,4-dioxanylcarbonyl group, azepanylcarbonyl group, 1,4-diazepanylcarbonyl group, pyrrolylcarbonyl group, thiazoylcarbonyl group, pyridylcarbonyl group, tetrahydropyridylcarbonyl group, tetrahydropyranylcarbonyl group, tetrahydrofuranylcarbonyl group, tetrahydroisoquinolylcarbonyl group, decahydroisoquinolylcarbonyl group and the like. The 3- to 10-membered heterocyclylcarbonyl group is preferably a 5- to 6-membered heterocyclylcarbonyl group.

The C1-6 alkyl group for $R^c$ in the group represented by formula: $-CR^c=NOR^d$ is as described above.

The C3-8 cycloalkyl group for $R^d$ in the group represented by formula: $-CR^c=NOR^d$ is as described above.

Examples of the C3-8 cycloalkyl group or C3-8 cycloalkenyl group substituted with an oxo group or alkylenedioxy group represented by $G^{22}$ include the following groups. * represents bonding site.

[Chemical formula 10]

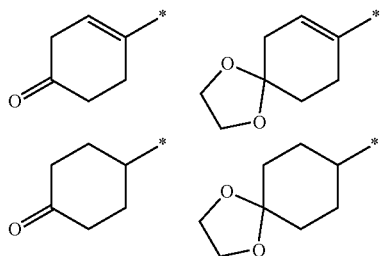

The 3- to 10-membered heterocyclyl group for $G^{22}$ is preferably a 5- to 6-membered heterocyclyl group.

$G^{22}$ is preferably an unsubstituted or hydroxyl-substituted C1-6 alkyl group, C1-6 haloalkyl group, C2-6 alkenyl group, C2-6 alkynyl group, C1-6 alkoxy group, C1-6 haloalkoxy group, di C1-6 alkylamino group, C1-6 alkylaminocarbonyl group, C1-6 alkylthio group, C1-6 haloalkylthio group, C1-6 alkylsulfinyl group, C1-6 haloalkylsulfinyl group, C1-6 alkylsulfonyl group, C1-6 haloalkylsulfonyl group, unsubstituted or $G^{221}$-substituted C3-8 cycloalkyl group, unsubstituted or $G^{221}$-substituted C6-10 aryl group, unsubstituted or $G^{221}$-substituted 3- to 10-membered heterocyclyl group, unsubstituted or $G^{221}$-substituted 3- to 10-membered heterocyclylcarbonyl group, pentafluorosulfanyl group, nitro group, cyano group, halogeno group, oxo group, unsubstituted or $G^{211}$-substituted C1-6 alkylenedioxy group, a group represented by $-CR^c=NOR^d$; and more preferably a C1-6 alkyl group, C1-6 haloalkyl group, C1-6 alkoxy group, C1-6 haloalkoxy group, unsubstituted or $G^{221}$-substituted C3-8 cycloalkyl group, unsubstituted or $G^{221}$-substituted C6-10 aryl group, unsubstituted or $G^{221}$-substituted 3- to 10-membered heterocyclyl group; and particularly preferably a C1-6 alkyl group, C1-6 haloalkyl group, unsubstituted or $G^{221}$-substituted cyclohexyl group, unsubstituted or $G^{221}$-substituted phenyl group, unsubstituted or $G^{221}$-substituted 5- to 6-membered heterocyclyl group (preferably a tetrahydropyranyl group, morpholinyl group, dioxolanyl group, furyl group, thienyl group, pyrazolyl group, pyridyl group).

[$G^{221}$]

$G^{221}$ represents a C1-6 alkyl group, a C1-6 haloalkyl group, a C1-6 alkoxy group, a C1-6 haloalkoxy group, a mono C1-6 alkylamino group, a di C1-6 alkylamino group, a C6-10 aryl group or a halogeno group. When there are two or more $G^{221}$-substituted groups, such $G^{221}$s may be the same as or different from each other.

The C1-6 alkyl group, C1-6 haloalkyl group, C1-6 alkoxy group, C1-6 haloalkoxy group, mono C1-6 alkylamino group, di C1-6 alkylamino group, C6-10 aryl group and halogeno group for substituent $G^{221}$ are as described above.

$G^{221}$ is preferably a C1-6 alkyl group, C1-6 haloalkyl group, C1-6 alkoxy group, C1-6 haloalkoxy group and halogeno group, and particularly preferably a methyl group, trifluoromethyl group or a chloro group.

[$R^1$]

$R^1$ represents a hydrogen atom, an unsubstituted or $G^1$-substituted C1-6 alkyl group, an unsubstituted or $G^1$-substituted C2-6 alkenyl group, an unsubstituted or $G^1$-substituted C1-6 alkoxy group, an unsubstituted or $G^1$-substituted C1-6 alkoxycarbonyl group, an unsubstituted or $G^1$-substituted C1-6 alkylthio group, An unsubstituted or $G^1$-substituted C1-6 alkylaminocarbonyl group, an unsubstituted or $G^2$-substituted C6-10 aryl group, a cyano group or a halogeno group.

The C1-6 alkyl group, C2-6 alkenyl group, C1-6 alkoxy group, C1-6 alkoxycarbonyl group, C1-6 alkylthio group, C1-6 alkylaminocarbonyl group, C6-10 aryl group, halogeno group, substituent $G^1$ and substituent $G^2$ for $R^1$ are as described above.

$R^1$ is preferably an unsubstituted or $G^1$-substituted C1-6 alkyl group (preferably unsubstituted) or a halogeno group, and particularly preferably a methyl group or a halogeno group.

[$R^2$]

$R^2$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, an unsubstituted or $G^1$-substituted C1-6 alkoxy group, a formyloxy group, an unsubstituted or $G^1$-substituted C1-6 alkylcarbonyloxy group, an unsubstituted or $G^2$-substituted C6-10 aryl group, an (unsubstituted or $G^1$-substituted C1-6 alkoxyimino)-C1-6 alkyl group, an unsubstituted or $G^2$-substituted 3- to 10-membered heterocyclyl C1-6 alkyl group, a cyano group or a halogeno group.

The C1-6 alkyl group, C2-6 alkenyl group, C3-8 cycloalkyl group, C1-6 alkoxy group, C1-6 alkylcarbonyloxy group, C6-10 aryl group, halogeno group, substituent $G^1$ and substituent $G^2$ for $R^2$ are as described above.

Examples of the (C1-6 alkoxyimino)-C1-6 alkyl group include a methoxyimino-methyl group, 1-(ethoxyimino)-ethyl group and the like.

The 3- to 10-membered heterocyclyl C1-6 alkyl group is the one in which a C1-6 alkyl group is substituted with the aforementioned 3- to 10-membered heterocyclyl group. Examples of the 3- to 10-membered heterocyclyl C1-6 alkyl group preferably include a tetrahydrofuranylmethyl group, tetrahydropyranylmethyl group, dioxolanylmethyl group, dioxanylmethyl group, pyrazolylmethyl group, pyridylmethyl group and the like. The 3- to 10-membered heterocyclyl C1-6 alkyl group is preferably a 5- to 6-membered heterocyclyl C1-6 alkyl group.

$R^2$ is preferably an unsubstituted or $G^1$-substituted C1-6 alkyl group (preferably unsubstituted) or a halogeno group, more preferably an unsubstituted or $G^1$-substituted C1-C6 alkyl group (preferably unsubstituted), and particularly preferably a methyl group.

[$R^3$]

$R^3$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, an unsubstituted or $G^1$-substituted C1-6 alkoxy group, an unsubstituted or $G^1$-substituted C1-6 alkylcarbonyl group, an unsubstituted or $G^1$-substituted C1-6 alkoxycarbonyl group, a carboxyl group, a formyl group, a formyloxy group, an unsubstituted or $G^1$-substituted C1-6 alkylcarbonyloxy group, an unsubstituted or $G^2$-substituted C6-10 aryl group, an unsubstituted or $G^2$-substituted 3- to 10-membered heterocyclyl group, an (unsubstituted or $G^1$-substituted C1-6 alkoxyimino)-C1-6 alkyl group, an unsubstituted or $G^1$-substituted mono C1-6 alkylamino group, an unsubstituted or $G^1$-substituted di C1-6 alkylamino group, a cyano group or a halogeno group.

The C1-6 alkyl group, C2-6 alkenyl group, C3-8 cycloalkyl group, C1-6 alkoxy group, C1-6 alkylcarbonyl group, C1-6 alkoxycarbonyl group, C1-6 alkylcarbonyloxy group, C6-10 aryl group, 3- to 10-membered heterocyclyl group, (C1-6 alkoxyimino)-C1-6 alkyl group, mono C1-6 alkylamino group, di C1-6 alkylamino group, halogeno group, substituent $G^1$ and substituent $G^2$ for $R^3$ are as described above.

The 3- to 10-membered heterocyclyl group for $R^3$ is preferably a 5- to 6-membered heteroaryl group.

$R^3$ is preferably an unsubstituted or $G^1$-substituted C1-6 alkyl group, unsubstituted or $G^1$-substituted C1-6 alkoxycarbonyl group, carboxyl group, unsubstituted or $G^2$-substituted C3-8 cycloalkyl group, unsubstituted or $G^2$-substituted 3- to 10-membered heterocyclyl group, unsubstituted or $G^1$-substituted di C1-6 alkylamino group; and more preferably an unsubstituted or $G^1$-substituted C1-6 alkyl group, unsubstituted or $G^2$-substituted C3-8 cycloalkyl group (preferably unsubstituted), unsubstituted or $G^2$-substituted 3- to 10-membered heterocyclyl group, unsubstituted or $G^1$-substituted C1-6 alkylamino group (preferably unsubstituted), and particularly preferably an unsubstituted or (preferably halogeno-)substituted C1-6 alkyl group.

[$R^4$]

$R^4$ in formula (I) represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl C1-6 alkyl group, an unsubstituted or $G^2$-substituted 3- to 10-membered heterocyclyl C1-6 alkyl group, a formyl group, an unsubstituted or $G^1$-substituted C1-6 alkylcarbonyl group, an unsubstituted or $G^2$-substituted C3-8 cycloalkylcarbonyl group, an unsubstituted or $G^1$-substituted C2-6 alkenylcarbonyl group, an unsubstituted or $G^2$-substituted C6-10 arylcarbonyl group, an unsubstituted or $G^1$-substituted C1-6 alkoxycarbonyl group, an unsubstituted or $G^1$-substituted C2-6 alkenyloxycarbonyl group, an unsubstituted or $G^1$-substituted C1-6 alkylsulfonyl group, an unsubstituted or $G^1$-substituted C1-6 alkylaminocarbonyl group, an unsubstituted or $G^1$-substituted (C1-6 alkylthio) carbonyl group, an unsubstituted or $G^1$-substituted C1-6 alkylamino (thiocarbonyl) group, or an organic group represented by formula (II).

The C1-6 alkyl group, C2-6 alkenyl group, C2-6 alkynyl group, C3-8 cycloalkyl group, C6-10 aryl C1-6 alkyl group, 3- to 10-membered heterocyclyl C1-6 alkyl group, C1-6 alkylcarbonyl group, C1-6 alkoxycarbonyl group, C1-6 alkylsulfonyl group, C1-6 alkylaminocarbonyl group, substituent $G^1$ and substituent $G^2$ for $R^4$ are as described above.

The C3-8 cycloalkylcarbonyl group is the one in which a carbonyl group is substituted with the above described C3-8 cycloalkyl group. Examples of the C3-8 cycloalkylcarbonyl group include a cyclopropylcarbonyl group, cyclobutylcarbonyl group, cyclopentylcarbonyl group, cyclohexylcarbonyl group and the like.

The C2-6 alkenylcarbonyl group is the one in which a carbonyl group is substituted with the above described C2-6 alkenyl group. Examples of the C2-6 alkenylcarbonyl group include a vinylcarbonyl group, 1-propenylcarbonyl group, 2-propenylcarbonyl group (allylcarbonyl group) and the like.

The C6-10 arylcarbonyl group is the one in which a carbonyl group is substituted with the above described C6-10 aryl group. Examples of the C6-10 arylcarbonyl group include a benzyl group, naphthoyl group and the like.

Examples of the C2-6 alkenyloxycarbonyl group include a vinyloxycarbonyl group, 1-propenyloxycarbonyl group, 2-propenyloxycarbonyl group (allyloxycarbonyl group) and the like.

Examples of the (C1-6 alkylthio) carbonyl group includes a (methylthio) carbonyl group, (ethylthio) carbonyl group and the like.

Examples of the C1-6 alkylamino (thiocarbonyl) group includes a methylamino (thiocarbonyl) group, dimethylamino (thiocarbonyl) group and the like.

[Chemical formula 11]

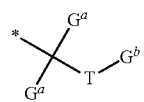

(II)

In formula (II), * represents bonding site.

In formula (II), each $G^a$ independently represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, or an unsubstituted or $G^2$-substituted C6-10 aryl group.

The C1-6 alkyl group, C2-6 alkenyl group, C2-6 alkynyl group, C3-8 cycloalkyl group, C6-10 aryl group, substituent $G^1$ and substituent $G^2$ for $G^a$ are as described above.

$G^a$ is preferably a hydrogen atom, or unsubstituted or $G^1$-substituted C1-6 alkyl group (preferably unsubstituted), more preferably a hydrogen atom or methyl group.

In formula (II), $G^b$ represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl group, or an unsubstituted or $G^2$-substituted 3- to 10-membered heterocyclyl group.

The C1-6 alkyl group, C2-6 alkenyl group, C2-6 alkynyl group, C3-8 cycloalkyl group, C6-10 aryl group, 3- to 10-membered heterocyclyl group, substituent $G^1$ and substituent $G^2$ for $G^b$ are as described above.

$G^b$ is preferably a hydrogen atom or unsubstituted or $G^1$-substituted C1-6 alkyl group (preferably unsubstituted), and particularly preferably a hydrogen atom, methyl group or isopropyl group.

In formula (II), T represents an oxygen atom, an oxycarbonyl group, a carbonyloxy group, an oxycarbonyloxy group, a sulfur atom, a (thio) carbonyl group, a carbonyl (thio) group, a (thio) carbonyloxy group, an oxycarbonyl (thio) group or a divalent group represented by —O—C (=O)—N($G^b$)-.

Examples of the group represented by formula (II) include the following groups.

[Chemical formula 12]

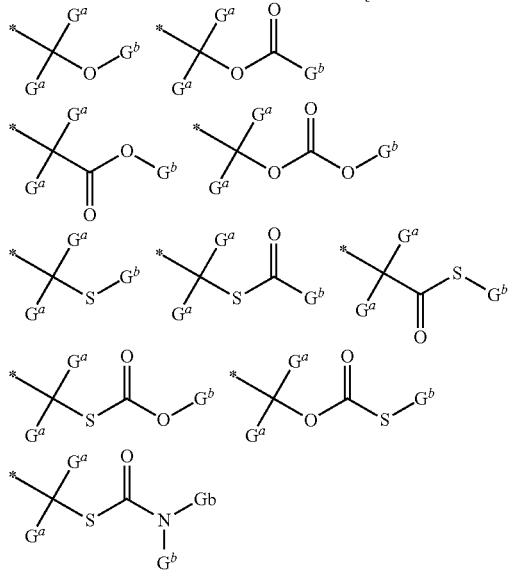

$R^4$ is preferably a hydrogen atom, unsubstituted or $G^1$-substituted C1-6 alkyl group, unsubstituted or $G^1$-substituted C2-6 alkenyl group, unsubstituted or $G^2$-substituted C6-10 aryl C1-6 alkyl group, unsubstituted or $G^2$-substituted 3- to 10-membered heterocyclyl C1-6 alkyl group, unsubstituted or $G^1$-substituted C1-6 alkylcarbonyl group, unsubstituted or $G^2$-substituted C3-8 cycloalkylcarbonyl group, unsubstituted or $G^1$-substituted C1-6 alkoxycarbonyl group or a group represented by the following formulas.

[Chemical formula 13]

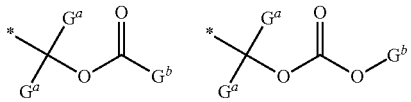

$R^4$ is more preferably a hydrogen atom, unsubstituted or $G^1$-substituted C1-6 alkylcarbonyl group (preferably unsubstituted), unsubstituted or $G^2$-substituted C3-8 cycloalkylcarbonyl group (preferably unsubstituted), unsubstituted or $G^1$-substituted C1-6 alkoxycarbonyl group (preferably unsubstituted) or a group represented by the following formulas.

[Chemical formula 14]

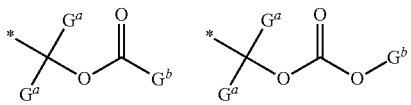

$R^4$ is particularly preferably a hydrogen atom, methoxycarbonyl group, ethoxycarbonyl group, acetyl group, ethylcarbonyl group, cyclopropylcarbonyl group or a group represented by the following formulas.

[Chemical formula 15]

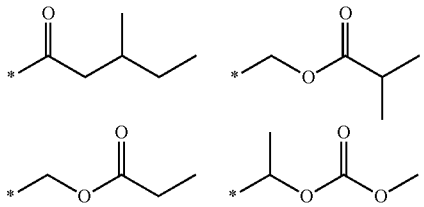

[A]

A in formula (I) represents an oxygen atom or a divalent organic group represented by formula (III).

[Chemical formula 16]

(III)

In formula (III), * represents bonding site.

In formula (III), $R^5$ and $R^6$ each independently represent a hydrogen atom, an unsubstituted or $G^1$-substituted C1-6 alkyl group, an unsubstituted or $G^1$-substituted C1-6 alkoxy group, an unsubstituted or $G^2$-substituted C6-10 aryloxy group, an unsubstituted or $G^1$-substituted alkoxycarbonyloxy group, a halogeno group, a hydroxyl group. $R^5$ and $R^6$ may bond to form a 3- to 6-membered ring together with the carbon atom to which $R^5$ and $R^6$ are bonded.

The C1-6 alkyl group, C1-6 alkoxy group, halogeno group and substituent $G^1$ for $R^5$ and $R^6$ are as described above.

$R^5$ is preferably a hydrogen atom, unsubstituted or $G^1$-substituted C1-6 alkyl group, unsubstituted C1-6 alkoxy group, unsubstituted or $G^2$-substituted C6-10 aryloxy group, unsubstituted alkoxycarbonyloxy group, halogeno group or hydroxyl group; more preferably a hydrogen atom, methyl group, methoxy group, methoxycarbonyloxy group, phenoxy group, benzyloxy group; and particularly preferably a hydrogen atom.

$R^6$ is preferably a hydrogen atom, unsubstituted or $G^1$-substituted C1-6 alkyl group, unsubstituted C1-6 alkoxy group, unsubstituted or $G^2$-substituted C6-10 aryloxy group, unsubstituted alkoxycarbonyloxy group, halogeno group or hydroxyl group; and more preferably a hydrogen atom, methyl group, methoxy group, a methoxycarbonyloxy group, phenoxy group or benzyloxy group; and particularly preferably a hydrogen atom.

[Cy]

In formula (I), Cy represents an unsubstituted or $G^2$-substituted C6-10 aryl group, a $G^2$-substituted C3-8 cycloalkyl group, an unsubstituted or $G^2$-substituted 3- to 10-membered heterocyclyl group or a $G^2$-substituted 13-membered heteroaryl group.

The C6-10 aryl group, C3-8 cycloalkyl group, 3- to 10-membered heterocyclyl group, 13-membered heteroaryl group and substituent $G^2$ for Cy are as described above.

The 3- to 10-membered heterocyclyl group for Cy is preferably a 3- to 6-membered heterocyclyl group, and particularly preferably a 5- to 6-membered heterocyclyl group.

Cy is preferably a $G^2$-substituted C6-10 aryl group, a $G^2$-substituted C5-6 cycloalkyl group, a $G^2$-substituted 3- to 6-membered heterocyclyl group; and more preferably a $G^2$-substituted C6-10 aryl group (preferably a phenyl group), $G^2$-substituted 5- to 6-membered heterocyclyl group (preferably a thienyl group, pyridyl group or pyrimidyl group). When Cy is a phenyl group, the substitution position of $G^2$ is preferably 4-position.

$G^2$ for Cy is preferably an unsubstituted or $G^{21}$-substituted C1-8 alkyl group, unsubstituted or $G^{21}$-substituted C2-6 alkenyl group, unsubstituted or $G^{21}$-substituted C2-6 alkynyl group, hydroxyl group, unsubstituted or $G^{21}$-substituted C1-6 alkoxy group, unsubstituted or $G^{21}$-substituted C1-6 alkylcarbonyl group, unsubstituted or $G^{21}$-substituted C1-6 alkoxycarbonyl group, unsubstituted or $G^{21}$-substituted unsubstituted mono C1-6 alkylcarbonylamino group, unsubstituted or $G^{21}$-substituted N—(C1-6 alkylcarbonyl)-N—(C1-6 alkyl) amino group, unsubstituted or $G^{21}$-substituted N—(C1-6 alkylcarbonyl)-N—(C1-6 alkoxycarbonyl) amino group, unsubstituted or $G^{21}$-substituted C1-6 alkoxycarbonyloxy group, mercapto group, unsubstituted or $G^{21}$-substituted C1-6 alkylthio group, unsubstituted or $G^{21}$-substituted C1-6 alkylsulfinyl group, unsubstituted or $G^{22}$-substituted C3-8 cycloalkyl group, unsubstituted or $G^{22}$-substituted C3-8 cycloalkenyl group, unsubstituted or $G^{22}$-substituted C3-8 cycloalkylcarbonylaminocarbonyl group, unsubstituted or $G^{22}$-substituted C6-10 aryl group, unsubstituted or $G^{22}$-substituted unsubstituted C6-10 aryloxy group, unsubstituted or $G^{22}$-substituted 3- to 10-membered heterocyclyl group, 13-membered heteroaryl group, unsubstituted or $G^{22}$-substituted 3- to 10-membered heterocyclyloxy group, cyano group, halogeno group, unsubstituted or $G^{21}$-substituted C1-6 alkylene group, a group represented by —$CR^a$=$NR^b$; more preferably an unsubstituted or $G^{21}$-substituted C1-8 alkyl group, unsubstituted or $G^{21}$-substituted C2-6 alkynyl group, unsubstituted or $G^{21}$-substituted C1-6 alkoxy group, unsubstituted or $G^{22}$-substituted C6-10 alkylcarbonyl group, unsubstituted or $G^{22}$-substituted C6-10 aryl group, unsubstituted or $G^{22}$-substituted C6-10 aryloxy group, unsubstituted or $G^{22}$-substituted 3- to 10-membered heterocyclyl group, unsubstituted or $G^{22}$-substituted 3- to 10-membered heterocyclyloxy group, cyano group, halogeno group, unsubstituted or $G^{21}$-substituted C1-6 alkylene group, a group represented by —$CR^a$=$NR^b$; and particularly preferably an unsubstituted or $G^{21}$-substituted C1-8 alkyl group, unsubstituted or $G^{21}$-substituted C2-6 alkynyl group, unsubstituted or $G^{21}$-substituted C1-6 alkoxy group, unsubstituted or $G^{21}$-substituted C1-6 alkylcarbonyl group, unsubstituted or $G^{22}$-substituted phenyl group, unsubstituted or $G^{22}$-substituted phenoxy group, unsubstituted or $G^{22}$-substituted 5- to 6-membered heterocyclyl group (preferably a 1,2,4-oxadiazolyl group, oxazolyl group, thiazolyl group, pyrazolyl group, 1,2,4-triazolyl group, pyridyl group, pyrimidyl group), unsubstituted or $G^{22}$-substituted 5- to 6-membered heterocyclyloxy group (preferably a pyridyloxy group), cyano group, halogeno group, unsubstituted or $G^{21}$-substituted C1-6 alkylene group, a group represented by —$CR^a$=$NR^b$; and particularly preferably an unsubstituted or $G^{22}$-substituted phenyl group, unsubstituted or $G^{22}$-substituted 5- to 6-membered heterocyclyl group (preferably a 1,2,4-oxadiazolyl group, oxazolyl group, thiazolyl group, pyrazolyl group, 1,2,4-triazolyl group, pyridyl group, pyrimidyl group).

The pyridine compound according to the present invention also includes a hydrate, various solvates, crystal polymorphism and the like. Furthermore, the pyridine compound according to the present invention includes stereoisomers based on the asymmetric carbon atoms, double bonds or the like, and mixtures and tautomers thereof. In addition, the pyridine compound according to the present invention also includes an N-oxide thereof. Here, N-oxide indicates a compound in which the nitrogen atom of the pyridine ring of formula (I) is oxidized.

[Tautomer]

When $R^4$ is a hydrogen atom, the pyridine compound according to the present invention generates the following tautomers (pyridin-4-one compound). In the formulas, $R^1$, $R^2$, $R^3$, A and Cy are as defined in formula (I). The pyridine compound according to the present invention includes these tautomers.

[Chemical formula 17]

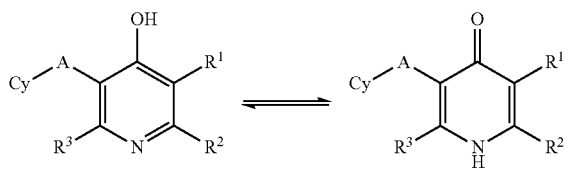

[Stereoisomer]

The present invention includes compounds represented by the same structural formula but having different spatial arrangements of atoms or substituents in the structure, for example, all kinds of stereoisomers such as optical isomers, diastereoisomers, geometric isomers or the like. The pyridine compound according to the present invention may be a single stereoisomer or a mixture of a plurality of stereoisomers.

[Salt]

The salt of compound (I) according to the present invention is not particularly limited as long as it is agriculturally and artificially acceptable. For example, salts of inorganic acids such as a hydrochloric acid, sulfuric acid or the like; salts of organic acids such as an acetic acid, lactic acid or the like; salts of alkali metals such as a lithium, sodium, potassium or the like; salts of alkaline earth metals such as a calcium, magnesium or the like; salts of transition metals such as an iron, copper or the like; salts of organic bases such as an ammonia, triethylamine, tributylamine, pyridine, hydrazine or the like; and the like may be mentioned. The salt of compound (I) can be obtained from compound (I) by a known method.

[Agricultural and Horticultural Fungicide, Harmful Organism Control Agent, and Insecticidal or Acaricidal Agent]

The agricultural and horticultural fungicide, the harmful organism control agent, and the insecticidal or acaricidal agent of the present invention include, as an active ingredient, at least one selected from the group consisting of compound (I), a tautomer of compound (I) or a salt of compound (I) (hereinafter, these may be referred to as "compound of the present invention").

The agricultural and horticultural fungicide of the present invention can be used for controlling plant diseases derived from fungi belonging to a wide variety of filamentous fungi such as oomycetes, ascomycetes, deuteromycetes, basidiomycetes, zygomycetes.

Examples of plant diseases (pathogens) to be controlled include the followings.

Sugar beet: brown spot disease (*Cercospora beticola*), black root disease (*Aphanomyces cochlioides*), root rot disease (*Thanatephorus cucumeris*), leaf rot disease (*Thanatephorus cucumeris*), and the like.

Peanut: brown spot disease (*Mycosphaerella arachidis*), leaf mold (*Ascochyta* sp.), rust disease (*Puccinia arachidis*), damping-off disease (*Pythium debaryanum*), rust spot disease (*Alternaria alternata*), stem rot disease (*Sclerotium rolfsii*), black rust disease (*Mycosphaerella berkeleyi*), and the like.

Cucumber: powdery mildew (*Sphaerotheca fuliginea*), downy mildew (*Pseudoperonospora cubensis*), gummy stem blight (*Mycosphaerella melonis*), wilt disease (*Fusarium oxysporum*), sclerotinia rot (*Sclerotinia sclerotiorum*), gray mold (*Botrytis cinerea*), anthracnose (*Colletotrichum orbiculare*), scab (*Cladosporium cucumerinum*), brown spot disease (*Corynespora cassiicola*), damping-off disease (*Pythium debaryanum, Rhizoctonia solani* Kuhn), *Phomopsis* root rot disease (*Phomopsis* sp.), Bacterial spot (*Pseudomonas syringae* pv. Lechrymans), and the like.

Tomato: gray mold disease (*Botrytis cinerea*), leaf mold disease (*Cladosporium fulvum*), late blight disease (*Phytophthora infestans*), verticillium wilt disease (*Verticillium albo-atrum, Verticillium dahliae*), powdery mildew disease (*Oidium neolycopersici*), early blight disease (*Alternaria solani*), leaf mold disease (*Pseudocercospora fuligena*), and the like.

Eggplant: gray mold disease (*Botrytis cinerea*), black rot disease (*Corynespora melongenae*), powdery mildew disease (*Erysiphe cichoracearum*), leaf mold disease (*Mycovellosiella nattrassii*), sclerotinia rot disease (*Sclerotinia sclerotiorum*), verticillium wilt disease (*Verticillium dahliae*), brown crest disease (*Phomopsis vexans*), and the like.

Strawberry: gray mold disease (*Botrytis cinerea*), powdery mildew disease (*Sphaerotheca humuli*), anthracnose disease (*Colletotrichum acutatum, Colletotrichum fragariae*), phytophthora rot disease (*Phytophthora cactorum*), soft rot disease (*Rhizopus stolonifer*), fsarium wilt disease (*Fusarium oxysporum*), wilt disease (*Verticillium dahliae*), and the like.

Onion: neck rot disease (*Botrytis allii*), gray mold disease (*Botrytis cinerea*), leaf blight disease (*Botrytis squamosa*), downy mildew disease (*Peronospora destructor*), *Phytophthora porri* disease (*Phytophthora porri*), and the like.

Cabbage: clubroot disease (*Plasmodiophora brassicae*), soft rot disease (*Erwinia carotovora*), black rot disease (*Xanthomonas campesrtis* pv. *campestris*), bacterial black spot disease (*Pseudomonas syringae* pv. *Maculicola*, P.s. pv. *alisalensis*), downy mildew disease (*Peronospora parasitica*), sclerotinia rot disease (*Sclerotinia sclerotiorum*), black spot disease (*Alternaria brassicicola*), gray mold disease (*Botrytis cinerea*), and the like.

Common bean: sclerotinia rot disease (*Sclerotinia sclerotiorum*), gray mold disease (*Botrytis cinerea*), anthracnose (*Colletotrichum lindemuthianum*), angular spot disease (*Phaeoisariopsis griseola*), and the like.

Apple: powdery mildew disease (*Podosphaera leucotricha*), scab disease (*Venturia inaequalis*), Monilinia disease (*Monilinia mali*), black spot disease (*Mycosphaerella pomi*), valsa canker disease (*Valsa mali*), alternaria blotch disease (*Alternaria mali*), rust disease (*Gymnosporangium yamadae*), ring rot disease (*Botryosphaeria berengeriana*), anthracnose disease (*Glomerella cingulata, Colletotrichum acutatum*), leaf srot disease (*Diplocarpon mali*), fly speck disease (*Zygophiala jamaicensis*), Sooty blotch (*Gloeodes pomigena*), violet root rot disease (*Helicobasidium mompa*), gray mold disease (*Botrytis cinerea*), and the like.

Japanese apricot: scab disease (*Cladosporium carpophilum*), gray mold disease (*Botrytis cinerea*), brown rot disease (*Monilinia mumecola*), and the like.

Persimmon: powdery mildew disease (*Phyllactinia kakicola*), anthracnose disease (*Gloeosporium kaki*), angular leaf spot (*Cercospora* kaki), and the like.

Peach: brown rot disease (*Monilinia fructicola*), scab disease (*Cladosporium carpophilum*), phomopsis rot disease (*Phomopsis* sp.), bacterial shot hole disease (*Xanthomonas campestris* pv. *pruni*), and the like.

Almond: brown rot disease (*Monilinia laxa*), spot blotch disease (*Stigmina carpophila*), scab disease (*Cladosporium carpophilum*), red leaf spot disease (*Polystigma rubrum*), alternaria blotch disease (*Alternaria alternata*), anthracnose (*Colletotrichum gloeospoides*), and the like.

Yellow peach: brown rot disease (*Monilinia fructicola*), anthracnose disease (*Colletotrichum acutatum*), black spot disease (*Alternaria* sp.), Monilinia Kusanoi disease (*Monilinia kusanoi*), and the like.

Grape: gray mold disease (*Botrytis cinerea*), powdery mildew disease (*Uncinula necator*), ripe rot disease (*Glomerella cingulata, Colletotrichum acutatum*), downy mildew disease (*Plasmopara viticola*), anthracnose disease (*Elsinoe ampelina*), brown spot disease (*Pseudocercospora vitis*), black rot disease (*Guignardia bidwellii*), white rot disease (*Coniella castaneicola*), rust disease (*Phakopsora ampelopsidis*), and the like.

Pear: scab disease (*Venturia nashicola*), rust disease (*Gymnosporangium asiaticum*), black spot disease (*Alternaria kikuchiana*), ring rot disease (*Botryosphaeria berengeriana*), powdery mildew disease (*Phyllactinia mali*), cytospora canker disease (*Phomopsis fukushii*), brown spot blotch disease (*Stemphylium vesicarium*), anthracnose disease (*Glomerella cingulata*), and the like.

Tea: ring spot disease (*Pestalotiopsis longiseta, P. theae*), anthracnose disease (*Colletotrichum theae-sinensis*), rice blast disease (*Exobasidium reticulatum*), and the like.

Citrus fruits: scab disease (*Elsinoe fawcettii*), blue mold disease (*Penicillium italicum*), common green mold disease (*Penicillium digitatum*), gray mold disease (*Botrytis* cinerea), melanose disease (*Diaporthe citri*), canker disease (*Xanthomonas campestris* pv. *Citri*), powdery mildew disease (*Oidium* sp.), and the like.

Wheat: powdery mildew (*Blumeria graminis* f. sp. *tritici*), red mold disease (*Gibberella zeae*), red rust disease (*Puccinia recondita*), brown snow mold disease (*Pythium iwayamai*), pink snow mold disease (*Monographella nivalis*), eye spot disease (*Pseudocercosporella herpotrichoides*), leaf scorch disease (*Septoria tritici*), glume blotch disease (*Leptosphaeria nodorum*), typhulasnow blight disease (*Typhula incarnata*), sclerotinia snow blight disease (*Myrioscleriotinia borealis*), damping-off disease (*Gaeumannomyces graminis*), ergot disease (*Claviceps purpurea*), stinking smut disease (*Tilletia caries*), loose smut disease (*Ustilago nuda*), and the like.

Barley: leaf spot disease (*Pyrenophora graminea*), net blotch disease (*Pyrenophora teres*), leaf blotch disease (*Rhynchosporium secalis*), loose smut disease (*Ustilago tritici, U. nuda*), and the like.

Rice: blast disease (*Pyricularia oryzae*), sheath blight disease (*Rhizoctonia solani*), bakanae disease (*Gibberella fujikuroi*), brown spot disease (*Cochliobolus miyabeanus*), damping-off disease (*Pythium graminicola*), bacterial leaf blight (*Xanthomonas oryzae*), bacterial seedling blight disease (*Burkholderia plantarii*), brown stripe disease (*Acidovorax avenae*), bacterial grain rot disease (*Burkholderia glumae*), *Cercospora* leaf spot disease (*Cercospora oryzae*), false smut disease (*Ustilaginoidea virens*), rice brown spot disease (*Alternaria alternata, Curvularia intermedia*), kernel discoloration of rice (*Alternaria padwickii*), pink coloring of rice grains (*Epicoccum purpurascens*), and the like.

Tobacco: sclerotinia rot disease (*Sclerotinia sclerotiorum*), powdery mildew disease (*Erysiphe cichoracearum*), phytophthora rot disease (*Phytophthora nicotianae*), and the like.

Tulip: gray mold disease (*Botrytis cinerea*), and the like.

Sunflower: downy mildew disease (*Plasmopara halstedii*), sclerotinia rot disease (*Sclerotinia sclerotiorum*), and the like.

Bent grass: *Sclerotinia* snow blight (*Sclerotinia borealis*), large patch (*Rhizoctonia solani*), brown patch (*Rhizoctonia solani*), dollar spot (*Sclerotinia homoeocarpa*), blast disease (*Pyricularia* sp.), *Pythium* red blight disease (*Pythium aphanidermatum*), anthracnose disease (*Colletotrichum graminicola*), and the like.

Orchard grass: powdery mildew disease (*Erysiphe graminis*), and the like.

Soybean: purple stain disease (*Cercospora kikuchii*), downy mildew disease (*Peronospora manshurica*), phytophthora rot disease (*Phytophthora sojae*), rust disease (*Phakopsora pachyrhizi*), sclerotinia rot disease (*Sclerotinia sclerotiorum*), anthracnose disease (*Colletotrichum truncatum*), gray mold disease (*Botrytis cinerea*), black rust disease (*Elsinoe glycines*), black spot disease (*Diaporthe phaseolorum* var. *Sojae*), and the like.

Potato: hytophthora rot disease (*Phytophthora infestans*), early blight disease (*Alternaria solani*), scurf disease (*Thanatephorus cucumeris*), half-body wilt disease (*Verticillium albo-atrum, V. dahliae, V. nigrescens*), and the like.

Banana: Panama disease (*Fusarium oxysporum*), Sigatoka disease (*Mycosphaerella fijiensis, M. musicola*), and the like.

Rape seed: sclerotinia rot disease (*Sclerotinia sclerotiorum*), root rot disease (*Phoma lingam*), black leaf spot disease (*Alternaria brassicae*), and the like.

Coffee: rust disease (*Hemileia vastatrix*), anthracnose (*Colletotrichum coffeanum*), leaf spot disease (*Cercospora coffeicola*), and the like.

Sugarcane: brown rust disease (*Puccinia melanocephala*), and the like.

Corn: zonate spot disease (*Gloeocercospora sorghi*), rust disease (*Puccinia sorghi*), southern rust disease (*Puccinia polysora*), smut disease (*Ustilago maydis*), brown spot disease (*Cochliobolus heterostrophus*), northern leaf blight (*Setosphaeria turcica*), and the like.

Cotton: seedling blight disease (*Pythium* sp), rust disease (*Phakopsora gossypii*), sour rot disease (*Mycosphaerella areola*), anthracnose (*Glomerella gossypii*), and the like.

The insecticidal or acaricidal agent of the present invention is excellent in the control effect of harmful organisms such as various agricultural pests affecting plant growth and acari. The insecticidal or acaricidal agent of the present invention is effective not only for susceptible strains but also for pests of strains in which resistance to conventional drugs such as organophosphate agents and carbamate agents has developed. Representative examples of resistant strains of pests include *Plutella xylostella*, delphacidae, cicadellidae, aphids and the like.

The harmful organism control agent of the present invention is effective for controlling harmful organisms other than agricultural pests and acari. As the harmful organisms, for example, ectoparasites, hygiene pests and the like can be mentioned.

The agricultural and horticultural fungicides, harmful organism control agents, and insecticidal or acaricidal agents of the present invention can be used for cereals, vegetables, root crops, potatoes, trees, grasses, lawn grasses and the like. It is preferable to use it for plants such as cereals; vegetables; root crops; potatoes; trees such as fruit trees, tea, coffee, cacao; grasses; lawn grasses; cotton.

The agricultural and horticultural fungicide, the harmful organism control agent, and the insecticidal or acaricidal agent of the present invention can be applied to various parts of plants such as leaves, stems, stalks, flowers, buds, fruits, seeds, sprouts, roots, tubers, tuberous roots, shoots, cuttings and the like. It is also possible to treat improved varieties/varieties, cultivars, as well as mutants, hybrids and genetically modified organisms (GMO).

The agricultural and horticultural fungicide of the present invention can be used for seed treatment, foliage application, soil application, water surface application, etc., which are carried out to control various diseases occurring in agricultural and horticultural crops including flowers, turf and grass.

The agricultural or horticultural fungicide, the harmful organism control agent, and the insecticidal or acaricidal agent of the present invention can be used in combination with other agricultural and horticultural chemicals having effects such as fungicidal effect, insecticidal/acaricidal effect, nematicidal effect, and soil pests control effect; or plant growth regulators, synergists, fertilizers, soil conditioners, animal feeds and the like. Examples are shown below.

Fungicide:

(1) Nucleic acid biosynthesis inhibitor:

(a) RNA polymerase I inhibitor: benalaxyl, benalaxyl-M, furalaxyl, metalaxyl, metalaxyl-M, oxadixyl, clozylacon, ofurace;

(b) adenosine deaminase inhibitor: bupirimate, dimethirimol, ethirimol;

(c) DNA/RNA synthesis inhibitor: hymexazol, octhilinone;

(d) DNA topoisomerase II inhibitor: oxophosphoric acid;

(2) Karyokinesis inhibitor and cell division inhibitor:

(a) β-tubulin polymerization inhibitor: benomyl, carbendazim, chlorfenazole, fuberidazole, thiabendazole, thiophanate, thiophanate-methyl, diethofencarb, zoxamide, ethaboxam;

(b) cell division inhibitor: pencycuron;

(c) delocalization inhibitor of spectrin-like protein: fluopicolide;

(3) Respiration inhibitor:

(a) complex I NADH oxidation-reduction inhibitor: diflumetorim, tolfenpyrad;

(b) complex II succinic acid dehydrogenase inhibitor: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxan, boscalid, pyraziflumid;

(c) complex III ubiquinol oxidase Qo inhibitor: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoximmethyl, trifloxystrobin, dimoxystrobin, fenaminstrobin, metominostrobin, orysastrobin, famoxadone, fluoxastrobin, fenamidone, pyribencarb, mandestrobin;

(d) complex III ubiquinol reductase Qi inhibitor: cyazofamid, amisulbrom;

(e) oxidative phosphorylation uncoupling agent: binapacryl, meptyldinocap, dinocap, fluazinam, ferimzone;

(f) oxidative phosphorylation inhibitor (ATP synthase inhibitor): fenthin acetate, fentin chloride, fentin hydroxide;

(g) ATP production inhibitor: silthiofam;

(h) complex III cytochrome bc1 (ubiquinone reductase) Qx (unknown) inhibitor: ametoctradin;

(4) Amino acid and protein synthesis inhibitor (a) methionine biosynthesis inhibitor: andoprim, cyprodinil, mepanipyrim, pyrimethanil;

(b) protein synthesis inhibitor: blasticidin-S, kasugamycin, kasugamycin hydrochloride, streptomycin, oxytetracycline;

(5) Signal transfer inhibitor:

(a) quinoxyfen, proquinazid;

(b) MAP/histidine kinase inhibitor in osmotic pressure signal transfer: fenpiconil, fludioxonil, chlozolinate, iprodione, procymidone, vinclozolin;

(6) Lipid and cell membrane synthesis inhibitor:

(a) phospholipid biosynthesis and methyltransferase inhibitor: edifenphos, iprobenfos, pyrazophos, isoprothiolane;

(b) lipid peroxide agent: biphenyl, chloroneb, dichloran, quintozene, tecnazene, tolclofos-methyl, etridiazole;

(c) agents affecting cell membrane: iodocarb, propamocarb, propamocarb hydrochloride, propamocarb-fosetylate, prothiocarb;

(d) microorganisms disturbing virus cell membrane: *Bacillus subtilis, Bacillus Subtilis* strain QST713, *Bacillus subtilis* strain FZB24, *Bacillus subtilis* strain MBI600, *Bacillus subtilis* strain D747;

(e) agents disturbing cell membrane: *melaleuca alternifolia* (tea tree) extract;

(7) Cell membrane sterol biosynthesis inhibitor:

(a) C14 position demethylation inhibitor in sterol biosynthesis: triforine; pyrifenox, pyrisoxazole, fenarimol, flurprimidol, nuarimol, imazalil, imazalil-sulphate, oxpoconazole, pefurazoate, prochloraz, triflumizole, viniconazole, azaconazole, bitertanol, bromconazole, cyproconazole, diclobutrazol, difenoconazole, diniconazole, diniconazole-M, epoxyconazole, etaconazole, fenbuconazole, fluquinconazole, flusilazole, flutriafol, furconazole, furconazole-cis, hexaconazole, imibenconazole, ipuconazole, metconazole, myclobutanil, penconazole, propiconazole, quinconazole, simeconazole, tebuconazole, tetraconazole, triadimefon, triadimenol, triticonazole, prothioconazole, voriconazole, mefentrifluconazole;

(b) Δ14 reductase and Δ8→Δ7-isomerase inhibitor in sterol biosynthesis: aldimorph, dodemorph, dodemorph-acetate, fenpropimorph, tridemorph, fenpropidine, piperalin, spiroxamine;

(c) 3-keto reductase inhibitor in C4 position demethylation in sterol biosynthesis system: fenhexamid, fenpyrazamine;

(d) squalene epoxidase inhibitor in sterol biosynthesis system: pyributicarb, naftifine, terbinafine;

(8) Cell wall synthesis inhibitor (a) trehalase inhibitor: validamycin;

(b) chitin synthetase inhibitor: polyoxins, polyoxorim;

(c) cellulose synthetase inhibitor: dimethomorph, flumorph, pyrimorph; benthiavalicarb, iprovalicarb, tolprocarb, tolprocarb, valifenalate, mandipropamide;

(9) Melanin biosynthesis inhibitor (a) reductase inhibitor in melamin biosynthesis: fthalide, pyroquilon, tricyclazole;

(b) anhydrase inhibitor in melanin biosynthesis: carpropamid, diclocymet, fenoxanil;

(c) others: tolprocarb.

(10) Resistance-inducing agent of host plant:

(a) agents affecting salicylic acid synthetic pathway: acibenzolar-s-methyl;

(b) others: probenazole, tiadinil, isotianil, laminarin, extract liquid of reynoutria *sachalinensis;*

(11) Agents of which the activity is unknown: cymoxanil, osetyl. aluminum, phosphoric acid (phosphate), tecloftalam, triazoxide, flusulfamide, diclomezine, methasulfocarb, cyflufenamid, metrafenone, pyriofenone, dodine, dodine free base, flutianil;

(12) Agent having multy activities: copper (copper salt), bordeaux mixture, copper hydroxide, copper naphthalate, copper oxide, oxychloride copper, copper sulfate, sulfur, sulfur product, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, chinomethionat, fluoroimide;

(13) Other agents: DBEDC, fluor folpet, guazatine acetate, bis (8-quinolinolato) copper (II), propamidine, chloropicrin, cyprofuram, agrobacterium, bethoxazin, diphenylamine, methyl isothiocyanate (MITC), mildew-mycin, capsaicin, curfraneb, cyprosulfamide, dazomet, debacarb, dichlorophen, difenzoquat, difenzoquat.methyl sulfonate, flumetover, fosetyl.calcium, fosetyl.sodium, irmamycin, natamycin, nitrothal isopropyl, oxamocarb, pyrrolnitrin, tebufloquin, tolnifanide, zarilamide, algophase, amicarthiazol, oxathiapiprolin, metiram zinc, benthiazole, trichlaamide, uniconazole, mildew-mycin, oxyfenthiin, picarbutrazox, fenpicoxamid, dichlobentiazox, quinofumelin.

Insecticides/acaricides, Nematocides, Soil pesticides, (1) Acetylcholine esterase inhibitor:

(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylycarb, fenothiocarb, MIPC, MPMC, MTMC, aldoxycarb, allyxycarb, aminocarb, bufencarb, cloethocarb, metam-sodium, promecarb;

(b) Organic phosphorus-based: acephate, azamethiphos, azinphos-ethyl, azinphos-methyl, cadusafos, chlorethoxyfos, chlorfenvinphos, chlormephos, chlorpyriphos, chlorpyriphos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothion, fenthion, fosthiazete, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiomethon, triazophos, trichlorfon, vamidothion, bromophos-ethyl, BRP, carbophenothion, cyanofenphos, CYAP, demeton-S-methyl sulphone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, sulprofos.

(2) GABA-agonistic chloride ion channel antagonist: acetoprole, chlordane, endosulfan, ethiprole, fipronil, pyrafluprole, pyriprole, camphechlore, heptachlor, dienochlor;

(3) Sodium channel modulator: acrinathrin, d-cis-trans-allethrin, d-trans allethrin, bifenthrin, bioallethrin, bioallethrin S-cyclopentyl isomer, bioresmethrin, cycloprotophosphorus, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ξ-cypermethrin, cyphenothrin [(1R)-trans isomer], δ-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin, allethrin, pyrethrin, pyrethrin I, pyrethrin II, profluthrin, dimefluthrin, bioethanomethrin, biopermethrin, transpermethirn, fenfluthrin, fenpirithrin, flubrocythrinate, flufenoprox, metofluthrin, protrifenbute, pyresmethrin, terallethrin;

(4) Nicotinic acetylcholine receptor agonist: acetamiprid, clothianidine, dinotefuran, imidacloprid, nitenpyram, nithiazine, thiacloprid, thiamethoxam, sulfoxaflor, nicotine, flupyradifurone;

(5) Nicotinic acetylcholine receptor allosteric modulator: spinetoram, spinosad;

(7) Juvenile hormone-like substances: hydroprene, kinoprene, methoprene, fenoxycarb, pyriproxyfen, diofenolan, epofeneonane, triprene;

(8) Other nonspecific inhibitor: methyl bromide, chloropicrin, sulfuryl fluoride, borax, tartar emetic;

(9) Homoptera selective feeding inhibitor: flonicamid, pymetrozine, pyrifluquinazon;

(10) Acari growth inhibitor: clofentezine, diflovidazin, hexythiazox, etoxazole;

(11) Microorganism-derived insect midgut inner membrane distrupting agent: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*, Bt crop protein: Cry1Ab, Cry1Ac, Cry1Fa, Cry1A.105, Cry2Ab, Vip3A, mCry3A, Cry3Ab, Cry3Bb, Cry34Ab1/Cry35Ab1;

(12) Mitochondria ATP biosynthesis enzyme inhibitor: diafenthiuron, azocyclotin, cyhexitin, fenbutatin oxide, propargite, tetradifon;

(13) Oxidative phosphorylation uncoupling agent: chlorfenapyr, sulfluramid, DNOC, binapacryl, dinobuton, dinocap;

(14) Nicotinic acetylcholine receptor channel blocker: bensultap, cartap hydrochloride, nereistoxin, thiosultap-sodium, thiocyclarm;

(15) Chitin synthesis inhibitor: bistrifluron, chlorfluazuron, diflubenzuron, flucycloxuron, flufenoxuron, hexaflumuron, lufenuron, novaluron, nobifumuron, teflubenzuron, triflumuron, buprofezin, fluazuron;

(16) Diptera molting disturbing agent: cyromazine;

(17) Molting hormone receptor agonist: chromafenozide, halofenozide, methoxyfenozide, tebufenozide;

(18) Octopamine receptor agonist: amitraz, demiditraz, chlordimeform;

(19) Mitochondria electron transfer chain complex III inhibitor: acequinocyl, fluacrypyrim, hydramethylnon;

(20) Mitochondria electron transfer chain complex I inhibitor: fenazaquin, fenpyroximate, pyrimidifen, pyridaben, tebufenpyrad, tolfenpyrad, rotenone;

(21) Voltage-dependent sodium channel blocker: indoxacarb, metaflumizone;

(22) Acetyl CoA carboxylase inhibitor: spirodiclofen, spiromesifen, spirotetramat;

(23) Mitochondria electron transfer chain complex IV inhibitor: aluminium phosphide, calcium phosphide, phosphine, zinc phosphide, cyanide;

(24) Mitochondria electron transfer chain complex II inhibitor: cyenopyrafen, cyflumetofen, pyflubumide;

(25) Ryanodine receptor modulator: chlorantraniliprole, cyantraniliprole, flubendiamide, cyclaniliprole, tetraniliprole;

(26) Mixed function oxidase inhibitor compound: piperonyl butoxide;

(27) Latrophilin receptor agonist: depsipeptide, cyclodepsipeptide, 24 membered cyclodepsipeptide, emodepside;

(28) Others (action mechanism is unknown): azadirachtin, benzoximate, bifenazate, bromopropylate, quinomethionate, cryolite, dicofol, pyridalyl, benclothiaz, sulfur, amidoflumet, 1,3-dichloropropene, DCIP, phenisobromolate, benzomate, methaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazole-3-yl]-2-(1H-1,2,4-triazole-1-yl) benzonitrile (CAS:943137-49-3), broflanilide, other metadiamide type.

[Ectoparasite Control Agent]

The compound of the present invention is excellent in controlling the ectoparasites that harm human beings. Also, it is a highly safe compound because it has less phytotoxicity and low toxicity to fish and warm-blooded animals. Therefore, it is useful as an active ingredient of an ectoparasite control agent.

Examples of the ectoparasites include acari, lice, fleas and the like.

Examples of host animals to be treated with the ectoparasite control agent of the present invention include pet animals such as dogs and cats; pet birds; livestock such as cattle, horse, pig, sheep; poultry, etc. Besides that, bees can be mentioned.

Ectoparasites parasitate in and on host animals, especially warm-blooded animals. In detail, it parasitizes on the back, armpit, lower abdomen, inner thigh, etc. of the host animal, and obtain nutrients such as blood and dandruff from the animals and inhabit.

The ectoparasite control agent of the present invention can be applied by a known veterinary method (topical, oral, parenteral or subcutaneous administration). Examples of the method therefor, a method of orally administering to an animal by tablet, capsule, feed mixed or the like; a method of administering to an animal by immersion liquid, suppository, injection (intramuscular, subcutaneous, intravenous, intraperitoneal, etc.); a method of locally administering an oily or aqueous liquid formulation by spraying, pour-on, spot-on or the like; a method of kneading an ectoparasite control agent in a resin, shaping the kneaded product into a suitable shape such as a collar, an ear tag or the like, attaching it to an animal and locally administering it; and the like.

[Preparation Formulation]

The agricultural and horticultural fungicide, the harmful organism control agent, and the insecticidal or acaricidal agent of the present invention are not particularly limited depending on the dosage form. For example, formulations such as wettable powders, emulsions, powders, granules, water-soluble agents, suspensions, granular wettable powders, tablets and the like can be mentioned. The method for preparing the formulation is not particularly limited, and a known preparation method can be adopted depending on the dosage form.

Some formulation examples are shown below. The formulation shown below is merely an example, and can be modified within a scope not contrary to the gist of the present invention, and the present invention is not limited by the following formulation examples at all. "Part" means "parts by weight" unless otherwise specified.

(Formulation 1: Wettable Powder)

| Compound of the present invention | 40 parts |
|---|---|
| Diatomaceous earth | 53 parts |
| Higher alcohol sulfate | 4 parts |
| Alkyl naphthalene sulfonate | 3 parts |

The above components are homogeneously mixed and finely pulverized to obtain a wettable powder with an active ingredient of 40%.

(Formulation 2: Emulsion)

| Compound of the present invention | 30 parts |
|---|---|
| Xylene | 33 parts |
| Dimethylformamide | 30 parts |
| Polyoxyethylene alkyl allyl ether | 7 parts |

The above components are mixed to obtain an emulsion having an active ingredient of 30%.

(Formulation 3: Powder)

| Compound of the present invention | 10 parts |
|---|---|
| Clay | 90 parts |

The above components are homogeneously mixed and finely pulverized to obtain a powder with an active ingredient of 10%.

(Formulation 4: Granule)

| Compound of the present invention | 5 parts |
|---|---|
| Clay | 73 parts |
| Bentonite | 20 parts |
| Dioctyl sulfosuccinate sodium salt | 1 part |
| Potassium phosphate | 1 part |

The above components are thoroughly pulverized and mixed, then water is added and kneaded well, followed by granulation and drying to obtain a granule having an active ingredient of 5%.

(Formulation 5: Suspension)

| Compound of the present invention | 10 parts |
|---|---|
| Polyoxyethylene alkyl allyl ether | 4 parts |
| Polycarboxylic acid sodium salt | 2 parts |
| Glycerin | 10 parts |
| Xanthan gum | 0.2 parts |
| Water | 73.8 parts |

The above components are mixed and wet pulverized until the particle size becomes 3 micron or less to obtain a suspension with an active ingredient of 10%.

(Formulation 6: Granular Wettable Powder)

| Compound of the present invention | 40 parts |
|---|---|
| Clay | 36 parts |
| Potassium chloride | 10 parts |
| Alkylbenzene sulfonic acid sodium salt | 1 part |
| Ligninsulfonic acid sodium salt | 8 parts |
| Formaldehyde condensate of alkylbenzene sulfonic acid sodium salt | 5 parts |

The above components are homogeneously mixed and finely pulverized, then an appropriate amount of water is added and the mixture is kneaded into clay. After granulating the clay-like material, it is dried to obtain a water dispersible granule having an active ingredient of 40%.

Next, the examples of the compound will be shown and the present invention will be described in more detail. However, the present invention is not limited by the following compound examples.

Example 1

Preparation of methyl (2,3,6-trimethyl-5-((4-(4-(trifluoromethoxy) phenoxy) phenyl) methyl)-4-pyridyl) carbonate (Compound No. 1-3)

(Step 1) Synthesis of 4-benzyloxy-2,6-dimethyl-3-((4-(4-(trifluoromethoxy) phenoxy) phenyl) methyl) pyridine (Compound No. 1-13)

[Chemical formula 18]

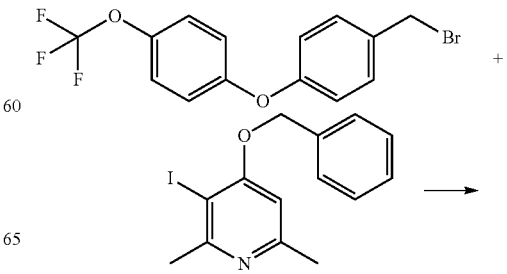

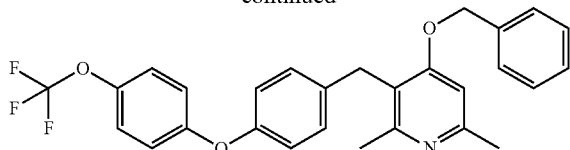

554 mg of zinc was added to a dried flask, and the inside of the reaction system was replaced with nitrogen. 6 ml of tetrahydrofuran and 0.04 ml of 1,2-dibromoethane were added and the mixture was heated to 60° C. After allowing to cool to room temperature, 0.02 ml of chlorotrimethylsilane was added and the mixture was stirred at room temperature for 10 minutes. To this solution, a solution obtained by dissolving 1.80 g of 1-(bromomethyl)-4-(4-(trifluoromethoxy) phenoxy) benzene in 1.1 ml of tetrahydrofuran was added dropwise under ice-cooling. After completion of the dropwise addition, the mixture was stirred under ice-cooling for 10 minutes and further stirred at room temperature for 2 hours to prepare a zinc reagent.

1.55 g of 4-benzyloxy-3-iodo-2,6 dimethylpyridine and 0.16 g of dichlorobis (triphenylphosphine) palladium were added to a dried flask, and the inside of the reaction system was replaced with nitrogen. Thereafter, 10 ml of tetrahydrofuran was added thereto. The above zinc reagent was added to this liquid and heated under reflux for 3 days. The reaction solution was cooled to room temperature. Thereafter, the mixture was poured into a saturated aqueous solution of ammonium chloride, extracted with ethyl acetate, and the organic layer was dried over anhydrous magnesium sulfate. The solvent was distilled off under reduced pressure, and the residue was purified by silica gel column chromatography (developing solvent: n-hexane/ethyl acetate) to obtain 0.56 g of the objective compound. The yield was 26%. The results of NMR analysis of the target compound were as follows.

$^1$H-NMR (CDCl$_3$, δ ppm)

2.48 (s, 3H), 2.49 (s, 3H), 4.02 (s, 2H), 5.09 (s, 2H), 6.63 (s, 1H), 6.87-6.96 (m, 4H), 7.08-7.15 (m, 4H), 7.26-7.33 (m, 5H)

(Step 2) Synthesis of 2,6-dimethyl-3-((4-(4-(trifluoromethoxy) phenoxy) phenyl) methyl) pyridin-4-ol (Compound No. 1-14)

[Chemical formula 19]

0.56 g of 4-benzyloxy-2,6-dimethyl-3-((4-(4-(trifluoromethoxy) phenoxy) phenyl) methyl) pyridine, 10 ml of methanol and 0.10 g of 10% palladium-carbon were mixed, and the mixture was stirred overnight at room temperature under a hydrogen atmosphere. Insolubles were removed by filtration and the solvent was distilled off from the filtrate under reduced pressure to obtain 0.38 g of the target compound. The yield was 85%. The results of NMR analysis of the target compound were as follows.

$^1$H-NMR (CD$_3$OD, δ ppm)

2.28 (s, 3H), 2.30 (s, 3H), 3.90 (s, 2H), 6.25 (s, 1H), 6.89-7.00 (m, 4H), 7.19-7.23 (m, 4H)

(Step 3) Synthesis of 3-iodo-2,6-dimethyl-5-((4-(4-(trifluoromethoxy) phenoxy) phenyl) methyl) pyridin-4-ol (Compound No. 1-15)

[Chemical formula 20]

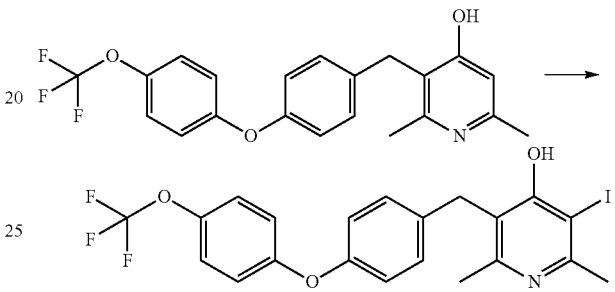

0.38 g of 2,6-dimethyl-3-((4-(4-(trifluoromethoxy) phenoxy) phenyl) methyl) pyridin-4-ol, 7 ml of acetic acid and 225 mg of N-iodosuccinimide were mixed, and the mixture was stirred at room temperature for 2 hours. The precipitated solid was collected by filtration and washed with a small amount of acetic acid and acetonitrile to obtain 0.18 g of the target compound. The yield was 36%. The results of NMR analysis of the target compound were as follows.

$^1$H-NMR (CD$_3$OD, δ ppm)

2.30 (s, 3H), 2.58 (s, 3H), 3.96 (s, 2H), 6.89-7.00 (m, 4H), 7.19-7.23 (m, 4H)

(Step 4) Synthesis of (3-iodo-2,6-dimethyl-5-((4-(4-(trifluoromethoxy) phenoxy) phenyl) methyl) 4-pyridyl) methyl carbonate (Compound No. 1-16)

[Chemical formula 21]

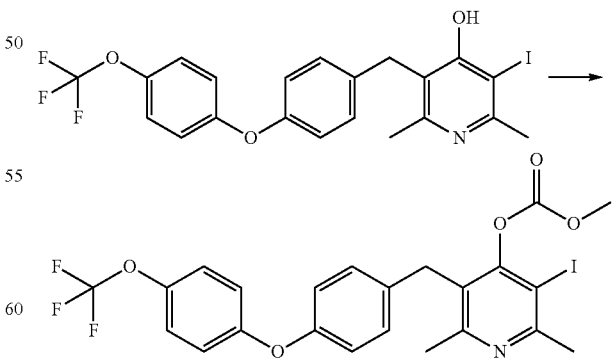

10 ml of chloroform and 0.19 g of triethylamine were added to 0.49 g of 3-iodo-2,6-dimethyl-5-((4-(4-(trifluoromethoxy) phenoxy) phenyl) methyl) pyridin-4-ol. To this reaction solution, 0.14 g of methyl chloroformate was added dropwise under ice-cooling, and the mixture was stirred at room temperature overnight. The reaction solution was poured into a saturated aqueous solution of sodium bicarbonate and extracted with chloroform. The organic layer was dried over anhydrous magnesium sulfate. The solvent was distilled off under reduced pressure, and the residue was purified by silica gel column chromatography (developing solvent: n-hexane/ethyl acetate) to obtain 0.48 g of the target compound. The yield was 88%. The results of NMR analysis of the target compound were as follows.

$^1$H-NMR (CDCl$_3$, δ ppm)

2.49 (s, 3H), 2.77 (s, 3H), 3.84 (s, 3H), 3.97 (s, 2H), 6.90-6.97 (m, 4H), 7.07-7.17 (m, 4H)

(Step 5) Synthesis of methyl (2,3,6-trimethyl-5-((4-(4-(trifluoromethoxy) phenyl) phenyl) methyl)-4-pyridyl) carbonate (Compound No. 1-3)

[Chemical formula 22]

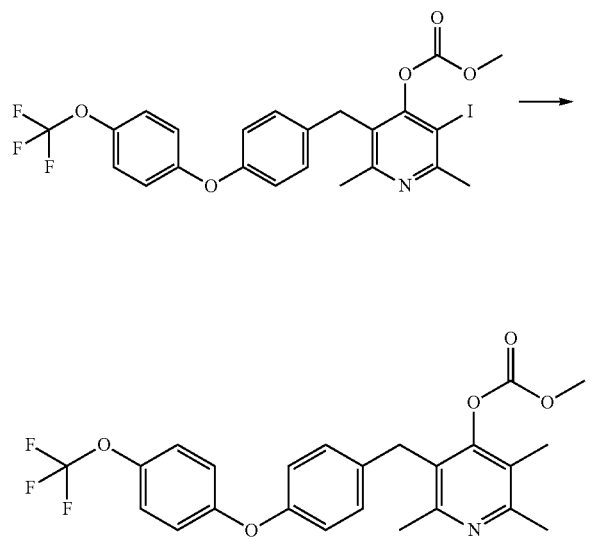

0.48 g of (3-iodo-2,6-dimethyl-5-((4-(4-(trifluoromethoxy) phenyl) phenyl) methyl) 4-pyridyl) methyl carbonate was dissolved in 10 ml of 1,2-dimethoxyethane, and 60 mg of bis (di t-butyl (4-dimethylaminophenyl) phosphine) dichloropalladium, 0.24 g of potassium carbonate and 0.21 g of trimethylboroxine were added to the resulting solution. The reaction system was replaced with nitrogen and heated to reflux for 1 hour. The reaction solution was cooled to room temperature. Thereafter, the solution was poured into a saturated aqueous ammonium chloride solution and extracted with ethyl acetate. The organic layer was dried over anhydrous magnesium sulfate. The solvent was distilled off under reduced pressure, and the residue was purified by silica gel column chromatography (developing solvent: n-hexane/ethyl acetate) to obtain 0.31 g of the target compound. The yield was 80%. The results of NMR analysis of the target compound were as follows.

$^1$H-NMR (CDCl$_3$, δ ppm)

2.10 (s, 3H), 2.48 (s, 3H), 2.51 (s, 3H), 3.79 (s, 3H), 3.92 (s, 2H), 6.89-6.97 (m, 4H), 7.08 (d, 2H), 7.15 (d, 2H)

Example 2

Preparation of (2-isopropyl-5,6-dimethyl-3-((4-(4-(trifluoromethoxy) phenoxy) phenyl) methyl)-4-pyridyl) methyl carbonate (Compound No. 1-9)

(Step 1) Synthesis of methyl 4-hydroxy-2-isopropyl-5,6-dimethyl nicotinate

[Chemical formula 23]

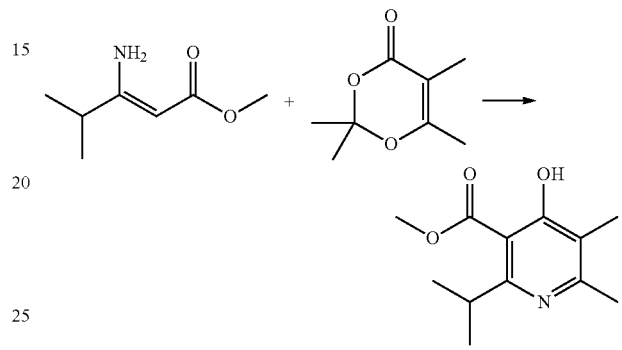

13.0 g of methyl 3-amino-4-methyl-2-pentenoate, 15.6 g of 2,2,5,6-tetramethyl-4H-1,3-dioxin-4-one and 18.2 g of molecular sieves 4 A were mixed, and the mixture was stirred at 170° C. for 20 minutes. Methanol was added to the reaction solution. Thereafter, the reaction solution was filtered, and the solvent was distilled off under reduced pressure from the filtrate. Diethylether was added to the obtained residue, and the precipitated crystals were collected by filtration to obtain 6.98 g of the target compound. The yield was 34%. The results of NMR analysis of the target compound were as follows.

$^1$H-NMR (DMSO-d$_6$, δ ppm) 1.20 (d, 6H), 1.80 (s, 3H), 2.26 (s, 3H), 3.70 (s, 3H), 10.57 (br.s, 1H)

(Step 2) Synthesis of 6-isopropyl-2,3-dimethylpyridin-4-ol

[Chemical formula 24]

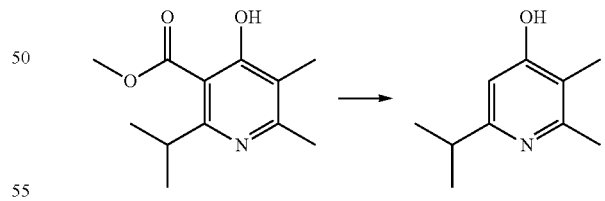

2.56 g of methyl 4-hydroxy-2-isopropyl-5,6-dimethyl nicotinate was dissolved in 11 ml of N-methyl-2-pyrrolidone. 4.86 g of lithium chloride was added to the resulting solution, and the mixture was stirred at 180° C. for 3 hours. The reaction solution was cooled to room temperature. Thereafter, the solution was poured into a saturated aqueous ammonium chloride solution and extracted with chloroform. The organic layer was dried over anhydrous magnesium sulfate. The solvent was distilled off under reduced pressure, and the residue was purified by silica gel column chromatography (developing solvent: chloroform/methanol) to obtain 1.49 g of the target compound. The yield was 79%. The results of NMR analysis of the target compound were as follows.

¹H-NMR (CD₃OD, δ ppm) 1.27 (d, 6H), 1.99 (s, 3H), 2.36 (s, 3H), 2.79-2.85 (m, 1H), 6.23 (s, 1H)

(Step 3) Synthesis of 3-iodo-2-isopropyl-5,6-dimethylpyridin-4-ol

[Chemical formula 25]

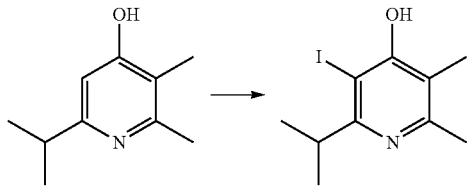

1.60 g of 6-isopropyl-2,3-dimethylpyridin-4-ol was mixed with 32 ml of chloroform, 8 ml of methanol and 2.40 g of N-iodosuccinimide, and stirred at room temperature for 3 hours. The precipitated solid was collected by filtration and washed with a small amount of acetonitrile and diethyl ether to obtain 1.60 g of the target compound. The yield was 57%. The results of NMR analysis of the target compound were as follows.

¹H-NMR (CD₃OD, δ ppm) 1.30 (d, 6H), 2.06 (s, 3H), 2.39 (s, 3H), 3.60-3.69 (m, 1H)

(Step 4) Synthesis of 4,4,5,5-tetramethyl-2-((4-(4-(trifluoromethoxy) phenoxy) phenyl) methyl)-1,3,2-dioxaborolane

[Chemical formula 26]

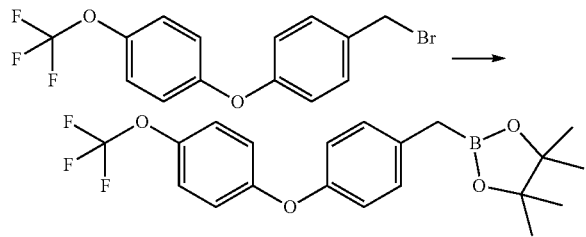

10.5 g of bis (pinacolato) diboron, 2.0 g of tetrakis (triphenylphosphine) palladium and 14.3 g of potassium carbonate were mixed. 100 ml of 1,4-dioxane and 12.0 g of 1-(bromomethyl)-4-(4-(trifluoromethoxy) phenoxy) benzene were added, the inside of the reaction system was replaced with nitrogen and heated and refluxed for 5 hours. The reaction solution was cooled to room temperature. Thereafter, the insoluble matter was removed by filtration, and the solvent was distilled off from the filtrate under reduced pressure. The obtained residue was purified by silica gel column chromatography (developing solvent: n-hexane/ethyl acetate) to obtain 5.46 g of the target compound. The yield was 40%. The results of NMR analysis of the target compound were as follows.

¹H-NMR (CDCl₃, δ ppm) 1.23 (s, 12H), 2.28 (s, 2H), 6.88-6.98 (m, 4H), 7.13-7.18 (m, 4H)

(Step 5) Synthesis of 2-isopropyl-5,6-dimethyl-3-((4-(4-(trifluoromethoxy) phenoxy) phenyl) methyl) pyridin-4-ol (Compound No. 1-8)

[Chemical formula 27]

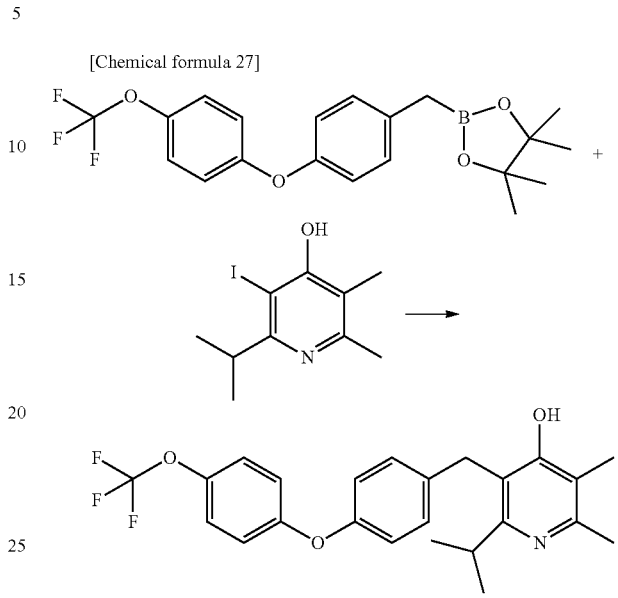

0.30 g of 3-iodo-2-isopropyl-5,6-dimethylpyridin-4-ol, 73 mg of bis (di t-butyl (4-dimethylaminophenyl) phosphine) dichloropalladium and 0.43 g of potassium carbonate were mixed. 5 ml of 1,4-dioxane, 0.49 g of 4,4,5,5-tetramethyl-2-((4-(4-(trifluoromethoxy) phenoxy) phenyl) methyl)-1,3,2-dioxaborolane, and 1 ml of water were added to the resulting mixture, and the atmosphere in the system was replaced with nitrogen, and the mixture was heated under reflux for 2 hours. The reaction solution was cooled to room temperature. Thereafter, the mixture was poured into a saturated aqueous solution of ammonium chloride, extracted with ethyl acetate, and the organic layer was dried over anhydrous magnesium sulfate. The solvent was distilled off under reduced pressure, and the obtained residue was purified by silica gel column chromatography (developing solvent: chloroform/methanol) to obtain 0.08 g of the target compound. The yield was 18%. The results of NMR analysis of the target compound were as follows.

¹H-NMR (CDCl₃, δ ppm)
1.15 (d, 6H), 2.04 (s, 3H), 2.29 (s, 3H), 3.18-3.27 (m, 1H), 3.98 (s, 2H), 6.85-6.94 (m, 4H), 7.11-7.21 (m, 4H), 7.96 (br.s, 1H)

(Step 6) Synthesis of (2-isopropyl-5,6-dimethyl-3-((4-(4-(trifluoromethoxy) phenoxy) phenyl) methyl)-4-pyridyl) methyl carbonate (Compound No. 1-9)

[Chemical formula 28]

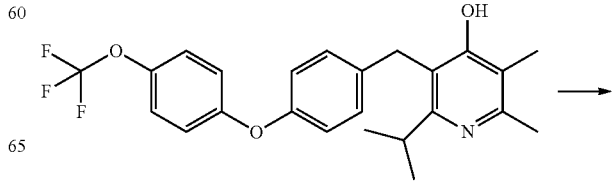

-continued

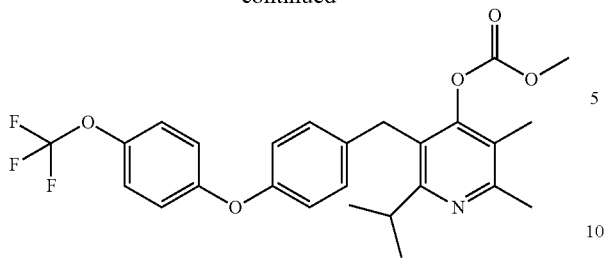

8 ml of chloroform and 71 mg of triethylamine were added to 0.15 g of 2-isopropyl-5,6-dimethyl-3-((4-(4-(trifluoromethoxy) phenoxy) phenyl) methyl) pyridin-4-ol. 50 mg of methyl chloroformate was added dropwise to the reaction solution under ice-cooling, and the mixture was stirred at room temperature for 2 hours. The reaction solution was poured into a saturated aqueous solution of sodium bicarbonate and extracted with chloroform. The organic layer was dried over anhydrous magnesium sulfate. The solvent was distilled off under reduced pressure, and the obtained residue was purified by silica gel column chromatography (eluent: n-hexane/ethyl acetate) to obtain 0.10 g of the target compound. The yield was 59%. The results of NMR analysis of the target compound were as follows.

$^1$H-NMR (CDCl$_3$, δ ppm)

1.17 (d, 6H), 2.08 (s, 3H), 2.51 (s, 3H), 3.19-3.22 (m, 1H), 3.76 (s, 3H), 3.95 (s, 2H), 6.89-6.94 (m, 4H), 7.06-7.15 (m, 4H)

Example 3

Preparation of 2-isopropyl-5,6-dimethyl-3-(4-(5-(trifluoromethyl)-1,2,4-oxadiazole-3-yl) benzyl) pyridine-4-yl methyl carbonate (Step 1) Synthesis of methyl 2-isopropyl-4-methoxy-5,6-dimethyl nicotinate

[Chemical formula 29]

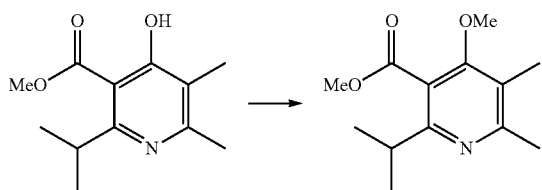

20 g of methyl 4-hydroxy-2-isopropyl-5,6-dimethyl nicotinate, 24.8 g of potassium carbonate, 25.4 g of methyl iodide and 300 ml of acetonitrile were mixed and heated under reflux for 3 hours. The reaction solution was filtered through celite, and the solvent was distilled off under reduced pressure. The obtained residue was diluted with ethyl acetate, washed with water, and then the solvent was distilled off under reduced pressure to obtain 21.3 g of the target compound. The yield was 100%. The results of NMR analysis of the target compound were as follows.

$^1$H-NMR (CDCl$_3$, δ ppm) 1.25 (d, 6H), 2.17 (s, 3H), 2.49 (s, 3H), 2.93 (m, 1H), 3.79 (s, 3H), 3.92 (s, 3H).

(Step 2) Synthesis of (2-isopropyl-4-methoxy-5,6-dimethylpyridin-3-yl) methanol

[Chemical formula 30]

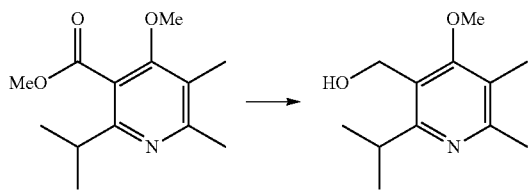

250 ml of tetrahydrofuran and 4.08 g of lithium aluminum hydride hydride were mixed and cooled to −10° C. To this mixed solution, a solution of 21.3 g of methyl 2-isopropyl-4-methoxy-5,6-dimethyl nicotinate in 90 ml of tetrahydrofuran was added dropwise. After completion of the dropwise addition, the temperature was raised to 30° C. and cooled again to 0° C. This operation was repeated by thin layer chromatography until disappearance of methyl 2-isopropyl-4-methoxy-5,6-dimethyl nicotinate was confirmed. The reaction solution was ice-cooled, and 4.08 g of water, 4.08 g of a 15% sodium hydroxide aqueous solution and 12.2 g of water were added successively, followed by filtration through celite, and the solvent was distilled off under reduced pressure to obtain 17.5 g the target compound. The yield was 93%. The results of NMR analysis of the target compound were as follows.

$^1$H-NMR (CDCl$_3$, δ ppm) 1.27 (d, 6H), 1.83 (m, 1H), 2.17 (s, 3H), 2.47 (s, 3H), 3.33 (m, 1H), 3.81 (s, 3H), 4.74 (d, 2H).

(Step 3) Synthesis of 3-(bromomethyl)-2-isopropyl-4-methoxy-5,6-dimethylpyridine

[Chemical formula 31]

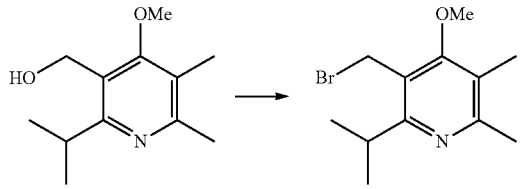

15.7 g of (2-isopropyl-4-methoxy-5,6-dimethylpyridin-3-yl) methanol and 42.5 g of carbon tetrabromide were dissolved in 300 ml of methylene chloride. 25.7 g of triphenylphosphine was added little by little at room temperature, and the mixture was stirred overnight at room temperature. The reaction solution was washed with aqueous sodium bicarbonate solution, the solvent was distilled off under reduced pressure, and the obtained residue was purified by silica gel column chromatography (developing solvent: n-hexane/ethyl acetate) to obtain 18.2 g of the target compound. The yield was 89%. The results of NMR analysis of the target compound were as follows.

$^1$H-NMR (CDCl$_3$, δ ppm) 1.29 (d, 6H), 2.17 (s, 3H), 2.47 (s, 3H), 3.31 (m, 1H), 3.88 (s, 3H), 4.63 (s, 2H).

(Step 4) Synthesis of 4-((2-isopropyl-4-methoxy-5,6-dimethylpyridin-3-yl) methyl) benzonitrile

[Chemical formula 32]

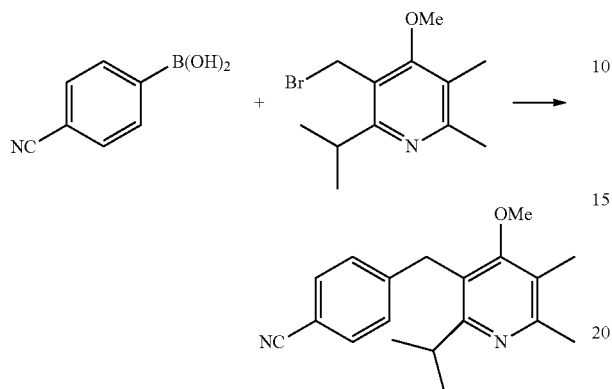

0.8 g of 3-(bromomethyl)-2-isopropyl-4-methoxy-5,6-dimethylpyridine, 0.647 g of 4-cyanophenylboronic acid, 0.608 g of potassium carbonate, 0.27 g of tetrakistriphenylphosphine palladium, 10 ml of 1,2-dimethoxyethane and 2 ml of water were mixed, replaced with argon, and heated under reflux for 1.5 hours under argon atmosphere. The solvent was distilled off under reduced pressure, and the resulting residue was purified by silica gel column chromatography (developing solvent: n-hexane/ethyl acetate) to obtain 0.55 g of the target compound. The yield was 64%. The results of NMR analysis of the target compound were as follows.

$^1$H-NMR (CDCl$_3$, δ ppm) 1.13 (d, 6H), 2.20 (s, 3H), 2.50 (s, 3H), 2.94-3.04 (m, 1H), 3.60 (s, 3H), 4.10 (s, 2H), 7.20 (d, 2H), 7.54 (d, 2H).

(Step 5) Synthesis of N-hydroxy-4-((2-isopropyl-4-methoxy-5,6-dimethylpyridin-3-yl) methyl) benzimidamide

[Chemical formula 33]

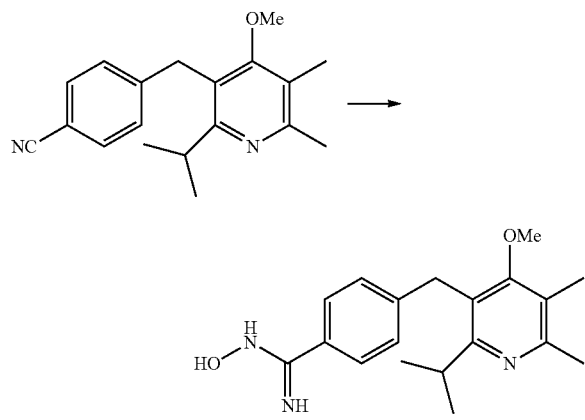

5.50 g of 4-((2-isopropyl-4-methoxy-5,6-dimethylpyridin-3-yl) methyl) benzonitrile, 100 ml of ethanol, 10 ml of water, 2.61 g of hydroxylamine hydrochloride, 5.30 g of sodium carbonate were mixed and heated to reflux for 4 hours. The reaction solution was diluted with water and extracted with ethyl acetate. The obtained organic layer was washed with water and saturated brine, and dried with magnesium sulfate. After filtration, the solvent was distilled off under reduced pressure, and the resulting residue was purified by silica gel column chromatography (developing solvent: n-hexane/ethyl acetate) to obtain 4.20 g of the target compound. The yield was 69%. The results of NMR analysis of the target compound were as follows.

$^1$H-NMR (CDCl$_3$, δ ppm) 1.13 (d, 6H), 2.19 (s, 3H), 2.49 (s, 3H), 2.98-3.08 (m, 1H), 3.60 (s, 3H), 4.10 (s, 2H), 7.10 (d, 2H), 7.50 (d, 2H).

(Step 6) Synthesis of 2-isopropyl-5,6-dimethyl-3-(4-(5-(trifluoromethyl)-1,2,4-oxadiazole-3-yl) benzyl) pyridine-4-ol

[Chemical formula 34]

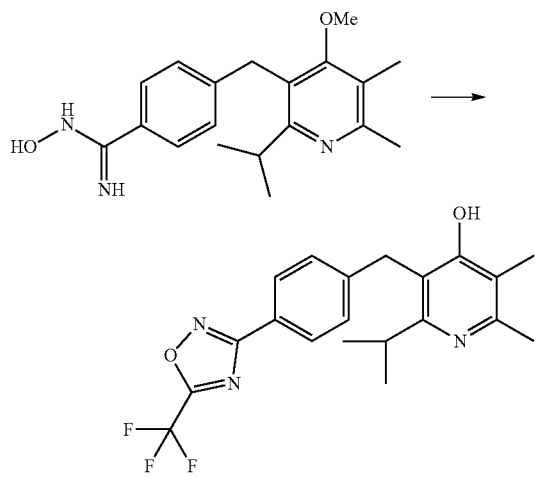

4.20 g of N-hydroxy-4-((2-isopropyl-4-methoxy-5,6-dimethylpyridin-3-yl) methyl) benzimidamide was dissolved in 100 ml of methylene chloride, and 4 ml of trifluoroacetic anhydride was mixed, and the mixture was stirred at room temperature for 6 hours. After distilling off the solvent under reduced pressure, 60 ml of dimethylformamide was added to the obtained residue, and the mixture was stirred at 130° C. for 20 minutes. This reaction solution was mixed with 2.70 g of lithium chloride and 12.4 g of p-toluenesulfonic acid monohydrate and stirred at 130° C. for 15 minutes. 8.2 g of sodium bicarbonate was added to the reaction solution, and the mixture was stirred at room temperature for 5 minutes, then diluted with water and filtered. The obtained crystals were washed successively with water and diethyl ether to obtain 5.20 g of the target compound. The yield was 90%. The results of NMR analysis of the target compound were as follows.

$^1$H-NMR (CDCl$_3$, δ ppm) 1.15 (d, 6H), 2.06 (s, 3H), 2.40 (s, 3H), 3.20-3.30 (m, 1H), 4.11 (s, 2H), 7.35 (d, 2H), 7.97 (d, 2H).

(Step 7) Synthesis of 2-isopropyl-5,6-dimethyl-3-(4-(5-(trifluoromethyl)-1,2,4-oxadiazole-3-yl) benzyl) pyridine-4-yl methyl carbonate

[Chemical formula 35]

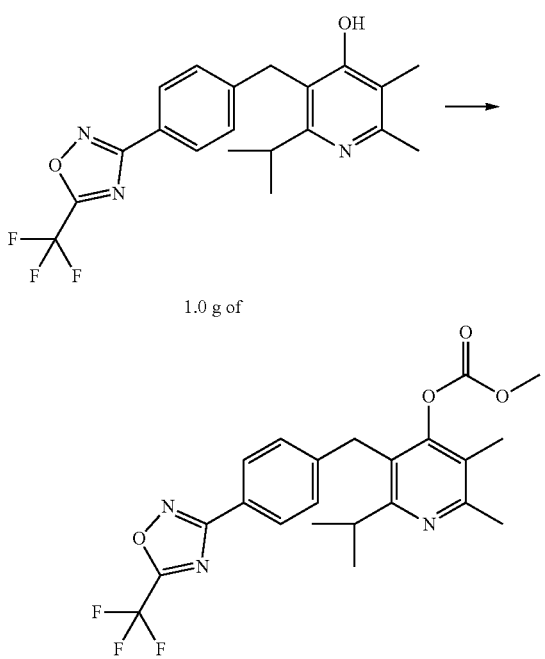

1.0 g of 2-isopropyl-5,6-dimethyl-3-(4-(5-(trifluoromethyl)-1,2,4-oxadiazole-3-yl) benzyl) pyridine-4-ol was dissolved in 30 ml of methylene chloride, and mixed with 2 ml of triethylamine and 1 ml of methyl chloroformate under ice-cooling, and the mixture was stirred at room temperature for 1 hour. After distilling off the solvent under reduced pressure, the obtained residue was purified by silica gel column chromatography (developing solvent: n-hexane/thyl acetate) to obtain 600 mg of the target compound. The yield was 52%. The results of NMR analysis of the target compound were as follows.

$^1$H-NMR (CDCl$_3$, δ ppm) 1.16 (d, 6H), 2.09 (s, 3H), 2.53 (s, 3H), 3.09-3.19 (m, 1H), 3.73 (s, 3H), 4.04 (s, 2H), 7.23 (d, 2H), 7.99 (d, 2H).

Examples of the compounds produced by the same method as in the above examples are shown in TABLES 1 to 7. In addition, physical property data of the compounds is described in the column of "Property". As the physical property data, melting point [mp (° C.)], refractive index or properties thereof are described.

In the table, Me represents methyl group, Et represents ethyl group, nPr represents normal propyl group, iPr represents isopropyl group, cPr represents cyclopropyl group, nBu represents normal butyl group, iBu represents isobutyl group, tBu represents tertiary butyl group, cBu represents cyclobutyl group, cPen represents cyclopentyl group, cHex represents cyclohexyl group, Ac represents acetyl group, Ph represents phenyl group, Bn represents benzyl group, Py represents pyridyl group, PINB represents 4,4,5,5-tetramethyl-1,3,2-dioxaborolanyl group.

Table 1 shows the substituents in the compound represented by formula (1).

[Chemical formula 36]

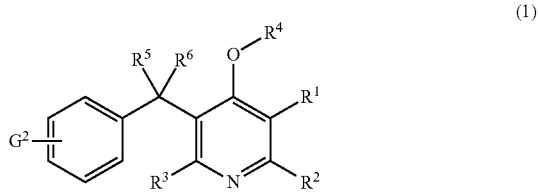

(1)

TABLE 1

| No. | R$^1$ | R$^2$ | R$^3$ | R$^4$ | R$^5$ | R$^6$ | G$^2$ | Physical Property |
|---|---|---|---|---|---|---|---|---|
| 1-1 | Me | (1H-pyrazol-1-yl)CH$_2$ | H | Me | H | H | 4-((4-OCF$_3$Ph)O) | m.p.: 56-58° C. |
| 1-2 | Me | (1H-pyrazol-1-yl)CH$_2$ | H | CO$_2$Me | H | H | 4-((4-OCF$_3$Ph)O) | viscous oil |
| 1-3 | Me | Me | Me | CO$_2$Me | H | H | 4-((4-OCF$_3$Ph)O) | viscous oil |
| 1-4 | Me | Me | N(Me)$_2$ | H | H | H | 4-((4-OCF$_3$Ph)O) | m.p.: 200° C. up |
| 1-5 | Me | Me | N(Me)$_2$ | CO$_2$Me | H | H | 4-((4-OCF$_3$Ph)O) | viscous oil |
| 1-6 | Me | Me | Me | H | H | H | 4-((4-OCF$_3$Ph)O) | m.p.: 200° C. up |
| 1-7 | Me | Me | CN | H | H | H | 4-((4-OCF$_3$Ph)O) | m.p.: 200° C. up |
| 1-8 | Me | Me | $^i$Pr | H | H | H | 4-((4-OCF$_3$Ph)O) | m.p.: 190-192° C. |
| 1-9 | Me | Me | $^i$Pr | CO$_2$Me | H | H | 4-((4-OCF$_3$Ph)O) | viscous oil |
| 1-10 | Me | Me | CH$_2$OMe | Allyl | OH | H | 4-$^t$Bu | viscous oil |
| 1-11 | Me | Me | CO$_2$Me | H | H | H | 4-((4-OCF$_3$Ph)O) | m.p.: 127-131° C. |
| 1-12 | Me | Me | CO$_2$H | H | H | H | 4-((4-OCF$_3$Ph)O) | m.p.: 200° C. up |
| 1-13 | H | Me | Me | Bn | H | H | 4-((4-OCF$_3$Ph)O) | viscous oil |
| 1-14 | H | Me | Me | H | H | H | 4-((4-OCF$_3$Ph)O) | (NMR) |
| 1-15 | I | Me | Me | H | H | H | 4-((4-OCF$_3$Ph)O) | (NMR) |
| 1-16 | I | Me | Me | CO$_2$Me | H | H | 4-((4-OCF$_3$Ph)O) | viscous oil |
| 1-17 | Me | Me | C(Me)$_2$OH | H | H | H | 4-((4-OCF$_3$Ph)O) | m.p.: 186-188° C. |

TABLE 1-continued

| No. | $R^1$ | $R^2$ | $R^3$ | $R^4$ | $R^5$ | $R^6$ | $G^2$ | Physical Property |
|---|---|---|---|---|---|---|---|---|
| 1-18 | Me | Me | C(Me)$_2$OH | CO$_2$Me | H | H | 4-((4-OCF$_3$Ph)O) | viscous oil |
| 1-19 | Me | Me | $^i$Pr | H | OH | H | 4-OCF$_3$ | m.p.: 85-88° C. |
| 1-20 | Me | Me | 1-Me-1H-2-pyrazol-3-yl | H | H | H | 4-((4-OCF$_3$Ph)O) | m.p.: 206-207° C. |
| 1-21 | Me | Me | 1-Me-1H-pyrazol-2-3-yl | CO$_2$Me | H | H | 4-((4-OCF$_3$Ph)O) | viscous oil |
| 1-22 | Me | Me | 5-Me-1,2,4-oxadiazol-3-yl | H | H | H | 4-((4-OCF$_3$Ph)O) | m.p.: 163-164° C. |
| 1-23 | Me | Me | 5-Me-1,2,4-oxadiazol-3-yl | CO$_2$Me | H | H | 4-((4-OCF$_3$Ph)O) | amorphous |
| 1-24 | Me | Me | $^i$Pr | H | H | H | 4-OCF$_3$ | m.p.: 209-210° C. |
| 1-25 | Me | Me | $^i$Pr | CO$_2$Me | H | H | 4-OCF$_3$ | m.p.: 60-61° C. |
| 1-26 | Me | Me | $^i$Pr | H | H | H | 4-(4-OCF$_3$Ph) | m.p.: 240° C. up |
| 1-27 | Me | Me | $^i$Pr | CO$_2$Me | H | H | 4-(4-OCF$_3$Ph) | viscous oil |
| 1-28 | Me | Me | $^i$Pr | H | H | H | 4-Cl | m.p.: 240° C. up |
| 1-29 | Me | Me | $^i$Pr | CO$_2$Me | H | H | 4-Cl | m.p.: 105-106° C. |
| 1-30 | Me | Me | CHF$_2$ | H | H | H | 4-((4-OCF$_3$Ph)O) | m.p.: 201-202° C. |
| 1-31 | Me | Me | CHF$_2$ | CO$_2$Me | H | H | 4-((4-OCF$_3$Ph)O) | m.p.: 92-93° C. |
| 1-32 | Me | Me | $^i$Pr | H | H | H | 4-(3-CF$_3$Ph) | m.p.: 219-220° C. |
| 1-33 | Me | Me | $^i$Pr | CO$_2$Me | H | H | 4-(3-CF$_3$Ph) | viscous oil |
| 1-34 | Br | Me | CHF$_2$ | H | H | H | 4-((4-OCF$_3$Ph)O) | m.p.: 176-177° C. |
| 1-35 | Br | Me | CHF$_2$ | CO$_2$Me | H | H | 4-((4-OCF$_3$Ph)O) | m.p.: 115-117° C. |
| 1-36 | Me | Me | $^i$Pr | H | H | H | 4-(4-MePh) | m.p.: 260° C. up |
| 1-37 | Me | Me | $^i$Pr | CO$_2$Me | H | H | 4-(4-MePh) | viscous oil |
| 1-38 | Br | Me | CHF$_2$ | H | H | H | 4-(4-OCF$_3$Ph) | m.p.: 247-249° C. |
| 1-39 | Br | Me | CHF$_2$ | CO$_2$Me | H | H | 4-(4-OCF$_3$Ph) | viscous oil |
| 1-40 | Me | Me | CHF$_2$ | CO$_2$Me | H | H | 4-(4-OCF$_3$Ph) | viscous oil |
| 1-41 | Me | Me | $^i$Pr | H | H | H | 4-(5-$^i$Pr-1,2,4-oxadiazol-3-yl) | m.p.: 234-235° C. |
| 1-42 | Me | Me | $^i$Pr | CO$_2$Me | H | H | 4-(5-$^i$Pr-1,2,4-oxadiazol-3-yl) | viscous oil |
| 1-43 | Me | Me | $^i$Pr | H | H | H | 4-(5-CF$_3$-1,2,4-oxadiazol-3-yl) | m.p.: 251-252° C. |
| 1-44 | Me | Me | $^i$Pr | CO$_2$Me | H | H | 4-(5-CF$_3$-1,2,4-oxadiazol-3-yl) | viscous oil |
| 1-45 | Me | Me | $^i$Pr | H | H | H | 4-(4-$^i$PrPh) | m.p.: 250° C. up |
| 1-46 | Me | Me | $^i$Pr | CO$_2$Me | H | H | 4-(4-$^i$PrPh) | viscous oil |
| 1-47 | Me | Me | $^i$Pr | H | H | H | 4-(4-EtPh) | m.p.: 250° C. up |
| 1-48 | Me | Me | $^i$Pr | CO$_2$Me | H | H | 4-(4-EtPh) | m.p.: 83-84° C. |
| 1-49 | Br | Me | $^i$Pr | CO$_2$Me | H | H | 4-(4-OCF$_3$Ph) | viscous oil |
| 1-50 | Br | Me | $^i$Pr | CO$_2$Me | H | H | 3-(4-OCF$_3$Ph) | viscous oil |
| 1-51 | Me | Me | $^i$Pr | CO$_2$Me | H | H | 3-(4-OCF$_3$Ph) | m.p.: 107-109° C. |
| 1-52 | Me | Me | $^i$Pr | H | H | H | 3-(4-OCF$_3$Ph) | m.p.: 227-229° C. |
| 1-53 | Me | Me | $^i$Pr | H | H | H | 3-Me-4-(perfluoropropan-4-2-yl) | m.p.: 250° C. up |
| 1-54 | Me | Me | $^i$Pr | CO$_2$Me | H | H | 3-Me-4-(perfluoropropan-4-2-yl) | viscous oil |
| 1-55 | Me | Me | $^i$Pr | H | H | H | 3-Me-5-(perfluoropropan-2-yl) | m.p.: 220-222° C. |
| 1-56 | Me | Me | $^i$Pr | CO$_2$Me | H | H | 3-Me-5-(perfluoropropan-2-yl) | viscous oil |
| 1-57 | Me | Me | CHF$_2$ | H | H | H | 4-(4-OCF$_3$Ph) | m.p.: 215-220° C. |
| 1-58 | Br | Me | $^i$Pr | H | H | H | 4-(4-OCF$_3$Ph) | m.p.: 250° C. up |
| 1-59 | Br | Me | $^i$Pr | H | H | H | 3-(4-OCF$_3$Ph) | m.p.: 192-196° C. |
| 1-60 | Me | Me | $^i$Pr | H | H | H | 4-(5-CF$_2$CF$_3$-1,2,4-oxadiazol-3-yl) | amorphous |

TABLE 1-continued

| No. | R$^1$ | R$^2$ | R$^3$ | R$^4$ | R$^5$ | R$^6$ | G$^2$ | Physical Property |
|---|---|---|---|---|---|---|---|---|
| 1-61 | Me | Me | $^i$Pr | CO$_2$Me | H | H | 4-(5-CF$_2$CF$_3$-1,2,4-oxadiazol-3-yl) | viscous oil |
| 1-62 | Me | Me | $^i$Pr | H | H | H | 4-(6-CF$_3$-pyridin-3-yl) | m.p.: 251-252° C. |
| 1-63 | Me | Me | $^i$Pr | CO$_2$Me | H | H | 4-(6-CF$_3$-pyridin-3-yl) | m.p.: 103-104° C. |
| 1-64 | Me | Me | $^i$Pr | H | H | H | 4-(5-CF$_3$-1,3,4-oxadiazol-2-yl) | amorphous |
| 1-65 | Me | Me | $^i$Pr | CO$_2$Me | H | H | 4-(5-CF$_3$-1,3,4-oxadiazol-2-yl) | viscous oil |
| 1-66 | Me | Me | $^i$Pr | H | H | H | 3-(5-CF$_3$-1,2,4-oxadiazol-3-yl) | viscous oil |
| 1-67 | Me | Me | $^i$Pr | CO$_2$Me | H | H | 3-(5-CF$_3$-1,2,4-oxadiazol-3-yl) | viscous oil |
| 1-68 | Me | Me | $^i$Pr | CO$_2$Me | H | H | 3-(5-CF$_2$CF$_3$-1,2,4-oxadiazol-3-yl) | m.p.: 62-63° C. |
| 1-69 | Me | Me | $^i$Pr | H | H | H | 3-F-4-(5-CF$_3$-1,2,4-oxadiazol-3-yl) | amorphous |
| 1-70 | Me | Me | $^i$Pr | CO$_2$Me | H | H | 3-F-4-(5-CF$_3$-1,2,4-oxadiazol-3-yl) | viscous oil |
| 1-71 | Me | Me | $^i$Pr | H | H | H | 3-F-4-(5-CF$_2$CF$_3$-1,2,4-oxadiazol-3-yl) | m.p.: 108-115° C. |
| 1-72 | Me | Me | $^i$Pr | CO$_2$Me | H | H | 3-F-4-(5-CF$_2$CF$_3$-1,2,4-oxadiazol-3-yl) | m.p.: 104-105° C. |
| 1-73 | Me | Me | $^i$Pr | CO$_2$Me | H | H | 3-F-4-(5-$^i$Pr-1,2,4-oxadiazol-3-yl) | viscous oil |
| 1-74 | Me | Me | $^i$Pr | H | H | H | 3-F-4-CN | m.p.: 230° C. up |
| 1-75 | Me | Me | $^i$Pr | CO$_2$Me | H | H | 3-F-4-CN | m.p.: 80-81° C. |
| 1-76 | Me | Me | $^i$Pr | H | H | H | 3-NHCOCF$_3$-4-OH | m.p.: 286-288° C. |
| 1-77 | Me | Me | $^i$Pr | CO$_2$Me | H | H | 3-N(COCF$_3$)(CO$_2$Me)-4-O—CO$_2$Me | m.p.: 40-42° C. |
| 1-78 | Me | Me | $^i$Pr | H | H | H | 3-(3-CF$_3$Ph) | m.p.: 215-217° C. |
| 1-79 | Me | Me | $^i$Pr | CO$_2$Me | H | H | 3-(3-CF$_3$Ph) | viscous oil |
| 1-80 | Me | Me | $^i$Pr | H | H | H | 3-(2-CF$_3$Ph) | m.p.: 248-251° C. |
| 1-81 | Me | Me | $^i$Pr | CO$_2$Me | H | H | 3-(2-CF$_3$Ph) | viscous oil |
| 1-82 | Me | Me | $^i$Pr | H | H | H | 2-(4-CF$_3$Ph) | m.p.: 300° C. up |
| 1-83 | Me | Me | $^i$Pr | CO$_2$Me | H | H | 2-(4-CF$_3$Ph) | viscous oil |
| 1-84 | Me | Me | $^i$Pr | CO$_2$Et | H | H | 2-(4-CF$_3$Ph) | n$_D$(22.6° C.) 1.525 |
| 1-85 | Me | Me | $^i$Pr | H | H | H | 2-(3-CF$_3$Ph) | m.p.: 274-276° C. |
| 1-86 | Me | Me | $^i$Pr | CO$_2$Me | H | H | 2-(3-CF$_3$Ph) | viscous oil |
| 1-87 | Me | Me | $^i$Pr | H | H | H | 2-(2-CF$_3$Ph) | m.p.: 300° C. up |
| 1-88 | Me | Me | $^i$Pr | CO$_2$Me | H | H | 2-(2-CF$_3$Ph) | viscous oil |
| 1-89 | Me | Me | $^i$Pr | H | H | H | 4-(4-CF$_3$Ph) | m.p.: 296-298° C. |
| 1-90 | Me | Me | $^i$Pr | CO$_2$Me | H | H | 4-(4-CF$_3$Ph) | viscous oil |
| 1-91 | Me | Me | $^i$Pr | H | H | H | 4-(2-CF$_3$Ph) | m.p.: 276-277° C. |
| 1-92 | Me | Me | $^i$Pr | CO$_2$Me | H | H | 4-(2-CF$_3$Ph) | n$_D$(22.2° C.) 1.534 |
| 1-93 | Me | Me | $^i$Pr | H | H | H | 4-(C≡C-(4-MePh)) | m.p.: 158-159° C. |
| 1-94 | Me | Me | $^i$Pr | CO$_2$Me | H | H | 4-(C≡C-(4-MePh)) | m.p.: 37-39° C. |
| 1-95 | Me | Me | $^i$Pr | Me | H | H | 4-(1-((Z)-1-F-2-I-vinyl)-1H-pyrazol-3-yl) | m.p.: 102-103° C. |
| 1-96 | Me | Me | $^i$Pr | H | H | H | 3-SMe-4-CN | m.p.: 245-246° C. |
| 1-97 | Me | Me | $^i$Pr | CO$_2$Me | H | H | 3-SMe-4-CN | m.p.: 147-148° C. |
| 1-98 | Me | Me | $^i$Pr | CO$_2$Me | H | H | 4-(1-CH$_2$CF$_3$-1H-pyrazol-3-yl) | m.p.: 114-115° C. |
| 1-99 | Me | Me | $^i$Pr | H | H | H | 3-(4-CF$_3$Ph) | m.p.: 230-232° C. |
| 1-100 | Me | Me | $^i$Pr | CO$_2$Me | H | H | 3-(4-CF$_3$Ph) | viscous oil |
| 1-101 | Me | Me | $^i$Pr | Ac | H | H | 4-(5-CF$_3$-1,2,4-oxadiazol-3-yl) | m.p.: 114-115° C. |
| 1-102 | Br | Me | $^i$Pr | H | H | H | 4-(5-CF$_3$-1,2,4-oxadiazol-3-yl) | m.p.: 293-297° C. |

TABLE 1-continued

| No. | R$^1$ | R$^2$ | R$^3$ | R$^4$ | R$^5$ | R$^6$ | G$^2$ | Physical Property |
|---|---|---|---|---|---|---|---|---|
| 1-103 | Br | Me | $^i$Pr | CO$_2$Me | H | H | 4-(5-CF$_3$-1,2,4-oxadiazol-3-yl) | n$_D$(22.3° C.) 1.529 |
| 1-104 | Br | Me | $^i$Pr | H | H | H | 4-(5-CF$_2$CF$_3$-1,2,4-oxadiazol-3-yl) | m.p.: 297-300° C. |
| 1-105 | Br | Me | $^i$Pr | CO$_2$Me | H | H | 4-(5-CF$_2$CF$_3$-1,2,4-oxadiazol-3-yl) | n$_D$(22.5° C.) 1.496 |
| 1-106 | I | Me | $^i$Pr | H | H | H | 4-(5-CF$_2$CF$_3$-1,2,4-oxadiazol-3-yl) | m.p.: 281-283° C. |
| 1-107 | I | Me | $^i$Pr | CO$_2$Me | H | H | 4-(5-CF$_2$CF$_3$-1,2,4-oxadiazol-3-yl) | n$_D$(21.8° C.) 1.525 |
| 1-108 | Me | Me | $^i$Pr | H | H | H | 4-(2-Me-thiazol-4-yl) | m.p.: 243-246° C. |
| 1-109 | Me | Me | $^i$Pr | CO$_2$Me | H | H | 4-(2-Me-thiazol-4-yl) | viscous oil |
| 1-110 | Me | Me | $^i$Pr | H | H | H | 4-(5-CF$_3$-pyridin-2-yl) | m.p.: 300° C. up |
| 1-111 | Me | Me | $^i$Pr | CO$_2$Me | H | H | 4-(5-CF$_3$-pyridin-2-yl) | m.p.: 96-97° C. |
| 1-112 | Me | Me | $^i$Pr | H | H | H | 4-(5-Me-1,2,4-oxadiazol-3-yl) | m.p.: 261-262° C. |
| 1-113 | Me | Me | $^i$Pr | CO$_2$Me | H | H | 4-(5-Me-1,2,4-oxadiazol-3-yl) | viscous oil |
| 1-114 | Me | Me | $^i$Pr | H | H | H | 4-(5-Et-1,2,4-oxadiazol-3-yl) | m.p.: 214-215° C. |
| 1-115 | Me | Me | $^i$Pr | CO$_2$Me | H | H | 4-(5-Et-1,2,4-oxadiazol-3-yl) | viscous oil |
| 1-116 | Me | Me | $^i$Pr | H | H | H | 4-(5-$^t$Bu-1,2,4-oxadiazol-3-yl) | m.p.: 243-244° C. |
| 1-117 | Me | Me | $^i$Pr | CO$_2$Me | H | H | 4-(5-$^t$Bu-1,2,4-oxadiazol-3-yl) | viscous oil |
| 1-118 | Me | Me | $^i$Pr | H | H | H | 2-Me-4-(5-CF$_3$-1,2,4-oxadiazol-3-yl) | m.p.: 267-268° C. |
| 1-119 | Me | Me | $^i$Pr | CO$_2$Me | H | H | 2-Me-4-(5-CF$_3$-1,2,4-oxadiazol-3-yl) | viscous oil |
| 1-120 | Me | Me | $^i$Pr | H | H | H | 4-(4-CF$_3$-thiazol-2-yl) | m.p.: 231-235° C. |
| 1-121 | Me | Me | $^i$Pr | CO$_2$Me | H | H | 4-(4-CF$_3$-thiazol-2-yl) | m.p.: 117-119° C. |
| 1-122 | Me | Me | $^i$Pr | H | H | H | 4-(2-CF$_3$-thiazol-4-yl) | m.p.: 236-238° C. |
| 1-123 | Me | Me | $^i$Pr | CO$_2$Me | H | H | 4-(2-CF$_3$-thiazol-4-yl) | m.p.: 113-116° C. |
| 1-124 | Me | Me | $^i$Pr | H | H | H | 3-(5-Me-1,2,4-oxadiazol-3-yl) | m.p.: 264-265° C. |
| 1-125 | Me | Me | $^i$Pr | CO$_2$Me | H | H | 3-(5-Me-1,2,4-oxadiazol-3-yl) | m.p.: 82-85° C. |
| 1-126 | Me | Me | $^i$Pr | H | H | H | 3-(5-Et-1,2,4-oxadiazol-3-yl) | m.p.: 208-211° C. |
| 1-127 | Me | Me | $^i$Pr | CO$_2$Me | H | H | 3-(5-Et-1,2,4-oxadiazol-3-yl) | n$_D$(22.0° C.) 1.544 |
| 1-128 | Me | Me | $^i$Pr | H | H | H | 3-(5-$^i$Pr-1,2,4-oxadiazol-3-yl) | m.p.: 212-216° C. |
| 1-129 | Me | Me | $^i$Pr | CO$_2$Me | H | H | 3-(5-$^i$Pr-1,2,4-oxadiazol-3-yl) | n$_D$(21.8° C.) 1.532 |
| 1-130 | Me | Me | $^i$Pr | H | H | H | 4-(oxazol-5-yl) | m.p.: 254-258° C. |
| 1-131 | Me | Me | $^i$Pr | CO$_2$Me | H | H | 4-(oxazol-5-yl) | viscous oil |
| 1-132 | Me | Me | $^i$Pr | H | H | H | B(OH)$_2$ | m.p.: 298-301° C. |
| 1-133 | Me | Me | $^i$Pr | CO$_2$Me | H | H | 4-PINB | viscous oil |
| 1-134 | Me | Me | $^i$Pr | H | H | H | 4-Ph | m.p.: 272-273° C. |
| 1-135 | Me | Me | $^i$Pr | CO$_2$Me | H | H | 4-Ph | m.p.: 75-77° C. |
| 1-136 | Me | Me | $^i$Pr | H | H | H | 4-(4-F—Ph) | m.p.: 272-274° C. |
| 1-137 | Me | Me | $^i$Pr | CO$_2$Me | H | H | 4-(4-F—Ph) | n$_D$(22.7° C.) 1.561 |
| 1-138 | Me | Me | $^i$Pr | H | H | H | 4-(5-CHF$_2$-1,2,4-oxadiazol-3-yl) | m.p.: 186-187° C. |
| 1-139 | Me | Me | $^i$Pr | CO$_2$Me | H | H | 4-(5-CHF$_2$-1,2,4-oxadiazol-3-yl) | viscous oil |
| 1-140 | Me | Me | $^i$Pr | H | H | H | 2-Me-4-(5-CF$_2$CF$_3$-1,2,4-oxadiazol-3-yl) | m.p.: 241-242° C. |
| 1-141 | Me | Me | $^i$Pr | CO$_2$Me | H | H | 2-Me-4-(5-CF$_2$CF$_3$-1,2,4-oxadiazol-3-yl) | viscous oil |
| 1-142 | Me | Me | $^i$Pr | H | H | H | 2-Me-4-(5-$^i$Pr-1,2,4-oxadiazol-3-yl) | m.p.: 250° C. up |

TABLE 1-continued

| No. | R¹ | R² | R³ | R⁴ | R⁵ | R⁶ | G² | Physical Property |
|---|---|---|---|---|---|---|---|---|
| 1-143 | Me | Me | $^i$Pr | CO₂Me | H | H | 2-Me-4-(5-$^i$Pr-1,2,4-oxadiazol-3-yl) | viscous oil |
| 1-144 | Me | Me | $^i$Pr | CH₂O—CO$^i$Pr | H | H | 4-(5-CF₃-1,2,4-oxadiazol-3-yl) | m.p.: 54-57° C. |
| 1-145 | Me | Me | $^i$Pr | H | H | H | 4-CN | m.p.: 250° C. up |
| 1-146 | Me | Me | $^i$Pr | CO₂Me | H | H | 4-CN | m.p.: 110-111° C. |
| 1-147 | Me | Me | $^i$Pr | CH₂OAc | H | H | 4-(5-CF₃-1,2,4-oxadiazol-3-yl) | m.p.: 89-90° C. |
| 1-148 | Me | Me | $^i$Pr | Bn | H | H | 4-(1,2,4-oxadiazol-3-yl) | viscous oil |
| 1-149 | Me | Me | $^i$Pr | CO₂Me | H | H | 4-(1,2,4-oxadiazol-3-yl) | m.p.: 101-105° C. |
| 1-150 | Me | Me | $^i$Pr | Ac | H | H | 4-(5-CF₂CF₃-1,2,4-oxadiazol-3-yl) | m.p.: 86-87° C. |
| 1-151 | Me | Me | $^i$Pr | H | H | H | 3-(3-MePh) | m.p.: 208-210° C. |
| 1-152 | Me | Me | $^i$Pr | CO₂Me | H | H | 3-(3-MePh) | viscous oil |
| 1-153 | Me | Me | $^i$Pr | Ac | H | H | 3-(3-MePh) | m.p.: 83-85° C. |
| 1-154 | Me | Me | $^i$Pr | H | H | H | 4-(6-CF₃-pyridazin-3-yl) | m.p.: 224-227° C. |
| 1-155 | Me | Me | $^i$Pr | CO₂Me | H | H | 4-(6-CF₃-pyridazin-3-yl) | m.p.: 174-177° C. |
| 1-156 | Me | Me | $^i$Pr | H | H | H | 4-(3-CF₃-1,2,4-oxadiazol-5-yl) | m.p.: 250-251° C. |
| 1-157 | Me | Me | $^i$Pr | CO₂Me | H | H | 4-(3-CF₃-1,2,4-oxadiazol-5-yl) | viscous oil |
| 1-158 | Me | Me | $^i$Pr | H | H | H | 4-(3-CF₂CF₃-1,2,4-oxadiazol-5-yl) | m.p.: 244-247° C. |
| 1-159 | Me | Me | $^i$Pr | CO₂Me | H | H | 4-(3-CF₂CF₃-1,2,4-oxadiazol-5-yl) | viscous oil |
| 1-160 | Me | Me | $^i$Pr | H | H | H | 4-(1-Me-5-CF₃-1H-1,2,4-triazol-3-yl) | m.p.: 280-282° C. |
| 1-161 | Me | Me | $^i$Pr | CO₂Me | H | H | 4-(1-Me-5-CF₃-1H-1,2,4-triazol-3-yl) | viscous oil |
| 1-162 | Me | Me | $^i$Pr | H | H | H | 4-(1-Me-5-CF₂CF₃-1H-1,2,4-triazol-3-yl) | m.p.: 292-293° C. |
| 1-163 | Me | Me | $^i$Pr | CO₂Me | H | H | 4-(1-Me-5-CF₂CF₃-1H-1,2,4-triazol-3-yl) | viscous oil |
| 1-164 | Me | Me | $^i$Pr | H | H | H | 4-(1,2,4-oxadiazol-3-yl) | m.p.: 250° C. up |
| 1-165 | Me | Me | $^i$Pr | CH₂OAc | H | H | 4-(5-CF₂CF₃-1,2,4-oxadiazol-3-yl) | m.p.: 87-88° C. |
| 1-166 | Me | Me | $^i$Pr | CH₂O—CO$^i$Pr | H | H | 4-(5-CF₂CF₃-1,2,4-oxadiazol-3-yl) | viscous oil |
| 1-167 | Me | Me | $^i$Pr | H | H | H | 3-(3-OCF₃Ph) | m.p.: 206-209° C. |
| 1-168 | Me | Me | $^i$Pr | CO₂Me | H | H | 3-(3-OCF₃Ph) | $n_D$(27.7° C.) 1.528 |
| 1-169 | Br | Me | $^i$Pr | H | H | H | 4-(4-MePh) | m.p.: 300° C. up |
| 1-170 | Br | Me | $^i$Pr | CO₂Me | H | H | 4-(4-MePh) | viscous oil |
| 1-171 | Me | Me | $^i$Pr | CH₂O—CO$^i$Pr | H | H | 3-(3-OCF₃Ph) | $n_D$(22.3° C.) 1.528 |
| 1-172 | Br | Me | $^i$Pr | Ac | H | H | 4-(4-OCF₃Ph) | m.p.: 105-106° C. |
| 1-173 | Br | Me | $^i$Pr | COEt | H | H | 4-(4-OCF₃Ph) | m.p.: 89-90° C. |
| 1-174 | Br | Me | $^i$Pr | CO$^c$Pr | H | H | 4-(4-OCF₃Ph) | m.p.: 104-105° C. |
| 1-175 | Br | Me | $^i$Pr | CO(2-Me$^n$Bu) | H | H | 4-(4-OCF₃Ph) | viscous oil |
| 1-176 | Br | Me | $^i$Pr | CO₂Et | H | H | 4-(4-OCF₃Ph) | viscous oil |
| 1-177 | Br | Me | $^i$Pr | CH₂O—CO$^i$Pr | H | H | 4-(4-MePh) | viscous oil |
| 1-178 | Me | Me | $^i$Pr | H | H | H | 4-(6-Me-pyridin-3-yl) | m.p.: 237-239° C. |
| 1-179 | Me | Me | $^i$Pr | CO₂Me | H | H | 4-(6-Me-pyridin-3-yl) | viscous oil |
| 1-180 | Br | Me | $^i$Pr | CH₂OAc | H | H | 4-(4-OCF₃Ph) | m.p.: 75-76° C. |
| 1-181 | Br | Me | $^i$Pr | CH(Me)O—CO₂Me | H | H | 4-(4-OCF₃Ph) | viscous oil |
| 1-182 | Cl | Me | $^i$Pr | CO₂Me | H | H | 4-(4-OCF₃Ph) | viscous oil |
| 1-183 | Me | Me | $^i$Pr | H | H | H | 3-(3-OCF₃Ph)-4-F | m.p.: 212-213° C. |
| 1-184 | Me | Me | $^i$Pr | CO₂Me | H | H | 3-(3-OCF₃Ph)-4-F | m.p.: 78-80° C. |

TABLE 1-continued

| No. | R¹ | R² | R³ | R⁴ | R⁵ | R⁶ | G² | Physical Property |
|---|---|---|---|---|---|---|---|---|
| 1-185 | Me | Me | $^i$Pr | H | H | H | 2-F-5-(3-OCF₃Ph) | m.p.: 238-240° C. |
| 1-186 | Me | Me | $^i$Pr | CO₂Me | H | H | 2-F-5-(3-OCF₃Ph) | viscous oil |
| 1-187 | Me | Me | $^i$Pr | H | H | H | 4-(6-F-pyridin-3-yl) | m.p.: 271-273° C. |
| 1-188 | Me | Me | $^i$Pr | CO₂Me | H | H | 4-(6-F-pyridin-3-yl) | viscous oil |
| 1-189 | Me | Me | $^i$Pr | H | H | H | 4-(6-O$^i$Pr-pyridin-3-yl) | m.p.: 227-229° C. |
| 1-190 | Me | Me | $^i$Pr | CO₂Me | H | H | 4-(6-O$^i$Pr-pyridin-3-yl) | viscous oil |
| 1-191 | Me | Me | $^i$Pr | H | H | H | 3-(5-CF₂CF₃-1,2,4-oxadiazol-3-yl) | m.p.: 207-210° C. |
| 1-192 | Me | Me | $^i$Pr | H | H | H | 3-(3-CF₂CF₃-1,2,4-oxadiazol-5-yl) | m.p.: 231-233° C. |
| 1-193 | Me | Me | $^i$Pr | CO₂Me | H | H | 3-(3-CF₂CF₃-1,2,4-oxadiazol-5-yl) | m.p.: 93-94° C. |
| 1-194 | Br | Me | $^i$Pr | CH₂O—CO$^i$Pr | H | H | 4-(4-OCF₃Ph) | viscous oil |
| 1-195 | Cl | Me | $^i$Pr | H | H | H | 4-(4-OCF₃Ph) | m.p.: 249-251° C. |
| 1-196 | Cl | Me | $^i$Pr | CH₂O—CO$^i$Pr | H | H | 4-(4-OCF₃Ph) | viscous oil |
| 1-197 | Me | Me | $^i$Pr | H | H | H | 2-F-4-(5-CF₃-1,2,4-oxadiazol-3-yl) | m.p.: 235-236° C. |
| 1-198 | Me | Me | $^i$Pr | CO₂Me | H | H | 2-F-4-(5-CF₃-1,2,4-oxadiazol-3-yl) | viscous oil |
| 1-199 | Me | Me | $^i$Pr | Ac | H | H | 2-F-4-(5-CF₃-1,2,4-oxadiazol-3-yl) | m.p.: 84-85° C. |
| 1-200 | Me | Me | $^i$Pr | Ac | H | H | 4-(3-CF₃-1,2,4-oxadiazol-5-yl) | m.p.: 143-147° C. |
| 1-201 | Me | Me | $^i$Pr | CH₂O—CO$^i$Pr | H | H | 4-(3-CF₃-1,2,4-oxadiazol-5-yl) | viscous oil |
| 1-202 | Me | Me | $^i$Pr | Ac | H | H | 4-(3-CF₂CF₃-1,2,4-oxadiazol-5-yl) | m.p.: 106-109° C. |
| 1-203 | Me | Me | $^i$Pr | H | H | H | 4-(2-$^i$Pr-oxazol-4-yl) | m.p.: 251-254° C. |
| 1-204 | Me | Me | $^i$Pr | CO₂Me | H | H | 4-(2-$^i$Pr-oxazol-4-yl) | viscous oil |
| 1-205 | Me | Me | $^i$Pr | H | H | H | 4-(2-$^t$Bu-oxazol-4-yl) | m.p.: 266-270° C. |
| 1-206 | Me | Me | $^i$Pr | CO₂Me | H | H | 4-(2-$^t$Bu-oxazol-4-yl) | viscous oil |
| 1-207 | Me | Me | $^i$Pr | H | H | H | 3-(3-OCF₃-4-Cl—Ph) | m.p.: 225-226° C. |
| 1-208 | Me | Me | $^i$Pr | CO₂Me | H | H | 3-(3-OCF₃-4-Cl—Ph) | viscous oil |
| 1-209 | Me | Me | $^i$Pr | H | H | H | 2-F-4-(5-CF₂CF₃-1,2,4-oxadiazol-3-yl) | m.p.: 243-246° C. |
| 1-210 | Me | Me | $^i$Pr | CO₂Me | H | H | 2-F-4-(5-CF₂CF₃-1,2,4-oxadiazol-3-yl) | viscous oil |
| 1-211 | Me | Me | $^i$Pr | Ac | H | H | 2-F-4-(5-CF₂CF₃-1,2,4-oxadiazol-3-yl) | m.p.: 78-79° C. |
| 1-212 | Me | Me | $^i$Pr | CO₂Me | H | H | 2-F-4-(5-$^i$Pr-1,2,4-oxadiazol-3-yl) | viscous oil |
| 1-213 | Me | Me | $^i$Pr | Ac | H | H | 2-F-4-(5-$^i$Pr-1,2,4-oxadiazol-3-yl) | viscous oil |
| 1-214 | Me | Me | $^i$Pr | H | H | H | 2-F-4-(5-$^t$Bu-1,2,4-oxadiazol-3-yl) | 250° C. up |
| 1-215 | Me | Me | $^i$Pr | CO₂Me | H | H | 2-F-4-(5-$^t$Bu-1,2,4-oxadiazol-3-yl) | viscous oil |
| 1-216 | Me | Me | $^i$Pr | Ac | H | H | 2-F-4-(5-$^t$Bu-1,2,4-oxadiazol-3-yl) | viscous oil |
| 1-217 | Me | Me | $^i$Pr | CO₂Me | H | H | 2-F-4-(5-Me-1,2,4-oxadiazol-3-yl) | viscous oil |
| 1-218 | Me | Me | $^i$Pr | CO₂Me | H | H | 3-SMe-4-(5-$^t$Bu-1,2,4-oxadiazol-3-yl) | m.p.: 96-97° C. |
| 1-219 | Me | Me | $^i$Pr | CO₂Me | H | H | 3-SH-4-(5-$^t$Bu-1,2,4-oxadiazol-3-yl) |  |
| 1-220 | Me | Me | $^i$Pr | CO₂Me | H | H | 3-SOMe-4-(5-$^t$Bu-1,2,4-oxadiazol-3-yl) | viscous oil |
| 1-221 | Me | Me | $^i$Pr | H | H | H | 4-(5-$^t$Pen-1,2,4-oxadiazol-3-yl) | m.p.: 245-246° C. |
| 1-222 | Me | Me | $^i$Pr | CO₂Me | H | H | 4-(5-$^t$Pen-1,2,4-oxadiazol-3-yl) | viscous oil |
| 1-223 | Me | Me | $^i$Pr | Ac | H | H | 4-(5-$^t$Bu-1,2,4-oxadiazol-3-yl) | m.p.: 118-119° C. |
| 1-224 | Me | Me | $^i$Pr | CO₂Me | H | H | 4-(5-CF₂CF₂H-1,2,4-oxadiazol-3-yl) | viscous oil |
| 1-225 | Me | Me | $^i$Pr | H | H | H | 3-F-4-(5-$^t$Bu-1,2,4-oxadiazol-3-yl) | amorphous |
| 1-226 | Me | Me | $^i$Pr | CO₂Me | H | H | 3-F-4-(5-$^t$Bu-1,2,4-oxadiazol-3-yl) | viscous oil |

TABLE 1-continued

| No. | R¹ | R² | R³ | R⁴ | R⁵ | R⁶ | G² | Physical Property |
|---|---|---|---|---|---|---|---|---|
| 1-227 | Me | Me | $^i$Pr | COEt | H | H | 4-(5-CF$_3$-1,2,4-oxadiazol-3-yl) | m.p.: 86-88° C. |
| 1-228 | Me | Me | $^i$Pr | CO$^c$Pr | H | H | 4-(5-CF$_3$-1,2,4-oxadiazol-3-yl) | m.p.: 102-103° C. |
| 1-229 | Me | Me | $^i$Pr | CO$_2$Me | H | H | 5-Cl-3-(5-CF$_3$-1,2,4-6-oxadiazol-3-yl) | m.p.: 105-106° C. |
| 1-230 | Me | Me | $^i$Pr | H | H | H | 5-Cl-3-(5-CF$_3$-1,2,4-6-oxadiazol-3-yl) | m.p.: 162-166° C. |
| 1-231 | Me | Me | $^i$Pr | COEt | H | H | 4-(3-CF$_3$-1,2,4-oxadiazol-5-yl) | m.p.: 100-102° C. |
| 1-232 | Me | Me | $^i$Pr | CO$^c$Pr | H | H | 4-(3-CF$_3$-1,2,4-oxadiazol-5-yl) | m.p.: 103-104° C. |
| 1-233 | Me | Me | $^i$Pr | CH$_2$OAc | H | H | 4-(3-CF$_3$-1,2,4-oxadiazol-5-yl) | m.p.: 97-98° C. |
| 1-234 | Me | Me | $^i$Pr | H | H | H | 3-F-4-(5-Me-1,2,4-oxadiazol-3-yl) | m.p.: 251-252° C. |
| 1-235 | Me | Me | $^i$Pr | CO$_2$Me | H | H | 3-F-4-(5-Me-1,2,4-oxadiazol-3-yl) | m.p.: 105-106° C. |
| 1-236 | Me | Me | $^i$Pr | H | H | H | 3-F-4-(5-Et-1,2,4-oxadiazol-3-yl) | m.p.: 222-223° C. |
| 1-237 | Me | Me | $^i$Pr | CO$_2$Me | H | H | 3-F-4-(5-Et-1,2,4-oxadiazol-3-yl) | m.p.: 92-93° C. |
| 1-238 | Me | Me | $^i$Pr | CO$_2$Me | H | H | 3-F-4-(5-$^n$Pr-1,2,4-oxadiazol-3-yl) | viscous oil |
| 1-239 | Me | Me | $^i$Pr | H | H | H | 4-(5-Me-pyrimidin-2-yl) | m.p.: 300° C. up |
| 1-240 | Me | Me | $^i$Pr | CO$_2$Me | H | H | 4-(5-Me-pyrimidin-2-yl) | m.p.: 132-134° C. |
| 1-241 | Me | Me | $^i$Pr | H | H | H | 4-(5-$^c$Bu-1,2,4-oxadiazol-3-yl) | m.p.: 213-214° C. |
| 1-242 | Me | Me | $^i$Pr | CO$_2$Me | H | H | 4-(5-$^c$Bu-1,2,4-oxadiazol-3-yl) | viscous oil |
| 1-243 | Me | Me | $^i$Pr | H | H | H | 4-(5-(tetrahydropyran-4-yl)-1,2,4-oxadiazol-3-yl) | m.p.: 207-208° C. |
| 1-244 | Me | Me | $^i$Pr | CO$_2$Me | H | H | 4-(5-(tetrahydropyran-4-yl)-1,2,4-oxadiazol-3-yl) | m.p.: 81-82° C. |
| 1-245 | Me | Me | $^i$Pr | CO$_2$Me | H | H | 3-CN-4-Cl | viscous oil |
| 1-246 | Me | Me | $^i$Pr | COCH$_2$CH(Me)Et | H | H | 4-(3-CF$_3$-1,2,4-oxadiazol-5-yl) | m.p.: 87-90° C. |
| 1-247 | Me | Me | $^i$Pr | CH(Me)O—CO$_2$Me | H | H | 4-(3-CF$_3$-1,2,4-oxadiazol-5-yl) | viscous oil |
| 1-248 | Cl | Me | $^i$Pr | CO$_2$Me | H | H | 4-(5-CF$_3$-1,2,4-oxadiazol-3-yl) | viscous oil |
| 1-249 | Cl | Me | $^i$Pr | CO$_2$Me | H | H | 4-(5-CF$_2$CF$_3$-1,2,4-oxadiazol-3-yl) | viscous oil |
| 1-250 | Cl | Me | $^i$Pr | H | H | H | 4-(3-CF$_3$-1,2,4-oxadiazol-5-yl) | m.p.: 287-289° C. |
| 1-251 | Cl | Me | $^i$Pr | CO$_2$Me | H | H | 4-(3-CF$_3$-1,2,4-oxadiazol-5-yl) | viscous oil |
| 1-252 | Cl | Me | $^i$Pr | H | H | H | 4-(3-CF$_2$CF$_3$-1,2,4-oxadiazol-5-yl) | m.p.: 294-296° C. |
| 1-253 | Cl | Me | $^i$Pr | CO$_2$Me | H | H | 4-(3-CF$_2$CF$_3$-1,2,4-oxadiazol-5-yl) | viscous oil |
| 1-254 | Br | Me | $^i$Pr | H | H | H | 4-(3-CF$_2$CF$_3$-1,2,4-oxadiazol-5-yl) | m.p.: 300° C. up |
| 1-255 | Br | Me | $^i$Pr | CO$_2$Me | H | H | 4-(3-CF$_2$CF$_3$-1,2,4-oxadiazol-5-yl) | viscous oil |
| 1-256 | Me | Me | $^i$Pr | H | H | H | 4-(5-Ph-1,2,4-oxadiazol-3-yl) | m.p.: 248-249° C. |
| 1-257 | Me | Me | $^i$Pr | CO$_2$Me | H | H | 4-(5-Ph-1,2,4-oxadiazol-3-yl) | m.p.: 100-101° C. |
| 1-258 | Me | Me | $^i$Pr | CO$_2$Me | H | H | 4-(5-morpholino-1,2,4-oxadiazol-3-yl) | m.p.: 135-136° C. |
| 1-259 | Me | Me | $^i$Pr | H | H | H | 3-(4-OCF$_3$Ph)-4-F | m.p.: 250-251° C. |
| 1-260 | Me | Me | $^i$Pr | CO$_2$Me | H | H | 3-(4-OCF$_3$Ph)-4-F | m.p.: 91-92° C. |
| 1-261 | Me | Me | $^i$Pr | H | H | H | 4-(3-$^t$Bu-1,2,4-oxadiazol-5-yl) | m.p.: 269-271° C. |
| 1-262 | Me | Me | $^i$Pr | CO$_2$Me | H | H | 4-(3-$^t$Bu-1,2,4-oxadiazol-5-yl) | m.p.: 128-130° C. |
| 1-263 | Me | Me | $^i$Pr | H | H | H | 4-(5-(pyridin-3-yl)-1,2,4-oxadiazol-3-yl) | m.p.: 249-250° C. |
| 1-264 | Me | Me | $^i$Pr | CO$_2$Me | H | H | 4-(5-(pyridin-3-yl)-1,2,4-oxadiazol-3-yl) | viscous oil |
| 1-265 | Me | Me | $^i$Pr | H | H | H | 4-(5-$^c$Hex-1,2,4-oxadiazol-3-yl) | m.p.: 170-171° C. |

TABLE 1-continued

| No. | R¹ | R² | R³ | R⁴ | R⁵ | R⁶ | G² | Physical Property |
|---|---|---|---|---|---|---|---|---|
| 1-266 | Me | Me | $^i$Pr | CO$_2$Me | H | H | 4-(5-$^c$Hex-1,2,4-oxadiazol-3-yl) | viscous oil |
| 1-267 | Me | Me | $^i$Pr | H | H | H | 4-(5-$^c$Pen-1,2,4-oxadiazol-3-yl) | m.p.: 215-216° C. |
| 1-268 | Me | Me | $^i$Pr | CO$_2$Me | H | H | 4-(5-$^c$Pen-1,2,4-oxadiazol-3-yl) | m.p.: 99-100° C. |
| 1-269 | Me | Me | $^i$Pr | H | H | H | 4-(5-(thiophen-3-yl)-1,2,4-oxadiazol-3-yl) | m.p.: 250° C. up |
| 1-270 | Me | Me | $^i$Pr | CO$_2$Me | H | H | 4-(5-(thiophen-3-yl)-1,2,4-oxadiazol-3-yl) | viscous oil |
| 1-271 | Me | Me | $^i$Pr | H | H | H | 4-(5-(furan-3-yl)-1,2,4-oxadiazol-3-yl) | m.p.: 251-252° C. |
| 1-272 | Me | Me | $^i$Pr | CO$_2$Me | H | H | 4-(5-(furan-3-yl)-1,2,4-oxadiazol-3-yl) | m.p.: 103-104° C. |
| 1-273 | Me | Me | $^i$Pr | H | H | H | 4-(5-(4-Me-$^c$Hex)-1,2,4-oxadiazol-3-yl) | m.p.: 196-197° C. |
| 1-274 | Me | Me | $^i$Pr | CO$_2$Me | H | H | 4-(5-(4-Me-$^c$Hex)-1,2,4-oxadiazol-3-yl) | viscous oil |
| 1-275 | Me | Me | $^i$Pr | H | H | H | 4-(5-(4-OMe—Ph)-1,2,4-oxadiazol-3-yl) | m.p.: 252-253° C. |
| 1-276 | Me | Me | $^i$Pr | CO$_2$Me | H | H | 4-(5-(4-OMe—Ph)-1,2,4-oxadiazol-3-yl) | m.p.: 124-125° C. |
| 1-277 | Me | Me | $^i$Pr | H | H | H | 4-(5-(1-Me-1H-pyrazol-4-yl)-1,2,4-oxadiazol-3-yl) | m.p.: 145-146° C. |
| 1-278 | Me | Me | $^i$Pr | CO$_2$Me | H | H | 4-(5-(1-Me-1H-pyrazol-4-yl)-1,2,4-oxadiazol-3-yl) | m.p.: 135-136° C. |
| 1-279 | Br | Me | $^i$Pr | H | H | H | 4-(3-CF$_3$-1,2,4-oxadiazol-5-yl) | m.p.: 300° C. up |
| 1-280 | Br | Me | $^i$Pr | CO$_2$Me | H | H | 4-(3-CF$_3$-1,2,4-oxadiazol-5-yl) | viscous oil |
| 1-281 | Me | Me | $^i$Pr | H | H | H | 4-(3-$^i$Pr-1,2,4-oxadiazol-5-yl) | m.p.: 225-226° C. |
| 1-282 | Me | Me | $^i$Pr | CO$_2$Me | H | H | 4-(3-$^i$Pr-1,2,4-oxadiazol-5-yl) | viscous oil |
| 1-283 | Me | Me | $^i$Pr | H | H | H | 4-(1-$^n$Bu-5-CF$_2$CF$_3$-1H-1,2,4-triazol-3-yl) | m.p.: 201-203° C. |
| 1-284 | Me | Me | $^i$Pr | CO$_2$Me | H | H | 4-(1-$^n$Bu-5-CF$_2$CF$_3$-1H-1,2,4-triazol-3-yl) | viscous oil |
| 1-285 | Me | Me | $^i$Pr | Ac | H | H | 4-(1-$^n$Bu-5-CF$_2$CF$_3$-1H-1,2,4-triazol-3-yl) | m.p.: 77-81° C. |
| 1-286 | Me | Me | $^i$Pr | H | H | H | 4-(1-$^n$Bu-3-CF$_2$CF$_3$-1H-1,2,4-triazol-5-yl) | m.p.: 201-203° C. |
| 1-287 | Me | Me | $^i$Pr | CO$_2$Me | H | H | 4-(1-$^n$Bu-3-CF$_2$CF$_3$-1H-1,2,4-triazol-5-yl) | m.p.: 105-108° C. |
| 1-288 | Me | Me | $^i$Pr | Ac | H | H | 4-(1-$^n$Bu-3-CF$_2$CF$_3$-1H-1,2,4-triazol-5-yl) | viscous oil |
| 1-289 | Me | Me | $^i$Pr | H | H | H | 4-(5-$^n$Pr-1,2,4-oxadiazol-3-yl) | m.p.: 157-158° C. |
| 1-290 | Me | Me | $^i$Pr | CO$_2$Me | H | H | 4-(5-$^n$Pr-1,2,4-oxadiazol-3-yl) | viscous oil |
| 1-291 | Me | Me | $^i$Pr | H | H | H | 4-(5-$^n$Bu-1,2,4-oxadiazol-3-yl) | m.p.: 185-186° C. |
| 1-292 | Me | Me | $^i$Pr | CO$_2$Me | H | H | 4-(5-$^n$Bu-1,2,4-oxadiazol-3-yl) | viscous oil |
| 1-293 | Me | Me | $^i$Pr | CO$_2$Me | H | H | 4-(5-N(Me)$_2$-1,2,4-oxadiazol-3-yl) | viscous oil |
| 1-294 | Me | Me | $^i$Pr | H | H | H | 3-Cl-4-(5-CF$_3$-1,2,4-oxadiazol-3-yl) | m.p.: 228-229° C. |
| 1-295 | Me | Me | $^i$Pr | CO$_2$Me | H | H | 3-Cl-4-(5-CF$_3$-1,2,4-oxadiazol-3-yl) | m.p.: 67-68° C. |
| 1-296 | Me | Me | $^i$Pr | Ac | H | H | 4-(3-$^t$Bu-1,2,4-oxadiazol-5-yl) | m.p.: 128-130° C. |
| 1-297 | Me | Me | $^i$Pr | Ac | H | H | 4-(5-CF$_3$-pyridin-2-yl) | m.p.: 162-164° C. |
| 1-298 | Me | Me | $^i$Pr | CH$_2$OAc | H | H | 4-(5-CF$_3$-pyridin-2-yl) | m.p.: 125-127° C. |
| 1-299 | Me | Me | $^i$Pr | H | H | H | 4-(5-$^i$Bu-1,2,4-oxadiazol-3-yl) | m.p.: 205-206° C. |
| 1-300 | Me | Me | $^i$Pr | CO$_2$Me | H | H | 4-(5-$^i$Bu-1,2,4-oxadiazol-3-yl) | viscous oil |
| 1-301 | Me | Me | $^i$Pr | CH$_2$O—CO$^i$Pr | H | H | 4-(5-$^t$Bu-1,2,4-oxadiazol-3-yl) | viscous oil |
| 1-302 | Me | Me | $^i$Pr | CH$_2$OAc | H | H | 4-(5-$^t$Bu-1,2,4-oxadiazol-3-yl) | viscous oil |
| 1-303 | Me | Me | $^i$Pr | H | H | H | 3-Me-4-(5-CF$_3$-1,2,4-oxadiazol-3-yl) | m.p.: 218-219° C. |

TABLE 1-continued

| No. | R¹ | R² | R³ | R⁴ | R⁵ | R⁶ | G² | Physical Property |
|---|---|---|---|---|---|---|---|---|
| 1-304 | Me | Me | $^i$Pr | CO$_2$Me | H | H | 3-Me-4-(5-CF$_3$-1,2,4-oxadiazol-3-yl) | m.p.: 52-53° C. |
| 1-305 | Me | Me | $^i$Pr | H | H | H | 3-Me-4-(5-$^t$Bu-1,2,4-oxadiazol-3-yl) | m.p.: 250° C. up |
| 1-306 | Me | Me | $^i$Pr | CO$_2$Me | H | H | 3-Me-4-(5-$^t$Bu-1,2,4-oxadiazol-3-yl) | m.p.: 108-109° C. |
| 1-307 | Me | Me | $^i$Pr | H | H | H | 3-Cl-4-(5-$^t$Bu-1,2,4-oxadiazol-3-yl) | m.p.: 250° C. up |
| 1-308 | Me | Me | $^i$Pr | CO$_2$Me | H | H | 3-Cl-4-(5-$^t$Bu-1,2,4-oxadiazol-3-yl) | m.p.: 100-101° C. |
| 1-309 | Me | Me | $^i$Pr | Ac | H | H | 3-F-4-(5-CF$_3$-1,2,4-oxadiazol-3-yl) | m.p.: 128-129° C. |
| 1-310 | Me | Me | $^i$Pr | CH$_2$O—CO$^i$Pr | H | H | 3-F-4-(5-CF$_3$-1,2,4-oxadiazol-3-yl) | viscous oil |
| 1-311 | Me | Me | $^i$Pr | CO$_2$Me | H | H | 4-(5-(CMe$_2$OH)-1,2,4-oxadiazol-3-yl) | viscous oil |
| 1-312 | Me | Me | $^i$Pr | H | H | H | 4-(5-$^c$Pr-1,2,4-oxadiazol-3-yl) | m.p.: 230-231° C. |
| 1-313 | Me | Me | $^i$Pr | CO$_2$Me | H | H | 4-(5-$^c$Pr-1,2,4-oxadiazol-3-yl) | viscous oil |
| 1-314 | Me | Me | $^i$Pr | CO$_2$Me | H | H | 4-(5-(morpholine-4-carbonyl)-1,2,4-oxadiazol-3-yl) | viscous oil |
| 1-315 | Me | Me | $^i$Pr | CO$_2$Me | H | H | 4-(5-(CON(Me)$_2$)-1,2,4-oxadiazol-3-yl) | viscous oil |
| 1-316 | Me | Me | $^i$Pr | CH$_2$OAc | H | H | 4-(3-$^t$Bu-1,2,4-oxadiazol-5-yl) | viscous oil |
| 1-317 | Me | Me | $^i$Pr | H | H | H | 4-(1-$^n$Bu-5-CF$_3$-1H-1,2,4-triazol-3-yl) | m.p.: 220-223° C. |
| 1-318 | Me | Me | $^i$Pr | CO$_2$Me | H | H | 4-(1-$^n$Bu-5-CF$_3$-1H-1,2,4-triazol-3-yl) | viscous oil |
| 1-319 | Me | Me | $^i$Pr | Ac | H | H | 4-(1-$^n$Bu-5-CF$_3$-1H-1,2,4-triazol-3-yl) | m.p.: 89-91° C. |
| 1-320 | Me | Me | $^i$Pr | H | H | H | 4-(1-$^n$Bu-3-CF$_3$-1H-1,2,4-triazol-5-yl) | m.p.: 247-248° C. |
| 1-321 | Me | Me | $^i$Pr | CO$_2$Me | H | H | 4-(1-$^n$Bu-3-CF$_3$-1H-1,2,4-triazol-5-yl) | viscous oil |
| 1-322 | Me | Me | $^i$Pr | Ac | H | H | 4-(1-$^n$Bu-3-CF$_3$-1H-1,2,4-triazol-5-yl) | viscous oil |
| 1-323 | Me | Me | $^i$Pr | H | H | H | 4-(1-$^n$Pr-5-CF$_3$-1H-1,2,4-triazol-3-yl) | m.p.: 243-244° C. |
| 1-324 | Me | Me | $^i$Pr | CO$_2$Me | H | H | 4-(1-$^n$Pr-5-CF$_3$-1H-1,2,4-triazol-3-yl) | viscous oil |
| 1-325 | Me | Me | $^i$Pr | Ac | H | H | 4-(1-$^n$Pr-5-CF$_3$-1H-1,2,4-triazol-3-yl) | m.p.: 115-116° C. |
| 1-326 | Me | Me | $^i$Pr | H | H | H | 4-(1-$^n$Pr-3-CF$_3$-1H-1,2,4-triazol-5-yl) | m.p.: 254-256° C. |
| 1-327 | Me | Me | $^i$Pr | CO$_2$Me | H | H | 4-(1-$^n$Pr-3-CF$_3$-1H-1,2,4-triazol-5-yl) | viscous oil |
| 1-328 | Me | Me | $^i$Pr | Ac | H | H | 4-(1-$^n$Pr-3-CF$_3$-1H-1,2,4-triazol-5-yl) | m.p.: 113-115° C. |
| 1-329 | Me | Me | $^i$Pr | H | H | H | 4-(1-(CH$_2$$^c$Pr)-5-CF$_3$-1H-1,2,4-triazol-3-yl) | m.p.: 237-239° C. |
| 1-330 | Me | Me | $^i$Pr | CO$_2$Me | H | H | 4-(1-(CH$_2$$^c$Pr)-5-CF$_3$-1H-1,2,4-triazol-3-yl) | viscous oil |
| 1-331 | Me | Me | $^i$Pr | H | H | H | 4-(1-(CH$_2$$^c$Pr)-3-CF$_3$-1H-1,2,4-triazol-5-yl) | m.p.: 252-256° C. |
| 1-332 | Me | Me | $^i$Pr | CO$_2$Me | H | H | 4-(1-(CH$_2$$^c$Pr)-3-CF$_3$-1H-1,2,4-triazol-5-yl) | viscous oil |
| 1-333 | Me | Me | $^i$Pr | CH$_2$O—CO$^i$Pr | H | H | 4-(5-CF$_3$-pyridin-2-yl) | m.p.: 92-94° C. |
| 1-334 | Me | Me | $^i$Pr | CH$_2$O—CO$^i$Pr | H | H | 4-(3-$^t$Bu-1,2,4-oxadiazol-5-yl) | viscous oil |
| 1-335 | Me | Me | $^i$Pr | CO$_2$Me | H | H | 4-([1,2,4]triazolo[4,3-a]pyridin-3-yl) | viscous oil |
| 1-336 | Me | Me | $^i$Pr | H | H | H | 4-(7-$^t$Bu-[1,2,4]triazolo[4,3-a]pyridin-3-yl) | m.p.: 300° C. up |
| 1-337 | Me | Me | $^i$Pr | CO$_2$Me | H | H | 4-(7-$^t$Bu-[1,2,4]triazolo[4,3-a]pyridin-3-yl) | m.p.: 167-170° C. |
| 1-338 | Br | Me | CHF$_2$ | H | H | H | 4-(5-CF$_3$-1,2,4-oxadiazol-3-yl) | m.p.: 260-263° C. |
| 1-339 | Br | Me | CHF$_2$ | CO$_2$Me | H | H | 4-(5-CF$_3$-1,2,4-oxadiazol-3-yl) | m.p.: 104-106° C. |
| 1-340 | Me | Me | $^i$Pr | H | H | H | 4-((3,5-Cl$_2$-pyridin-2-yl)O) | m.p.: 116-119° C. |
| 1-341 | Me | Me | $^i$Pr | CO$_2$Me | H | H | 4-((3,5-Cl$_2$-pyridin-2-yl)O) | viscous oil |

TABLE 1-continued

| No. | R$^1$ | R$^2$ | R$^3$ | R$^4$ | R$^5$ | R$^6$ | G$^2$ | Physical Property |
|---|---|---|---|---|---|---|---|---|
| 1-342 | Me | Me | $^i$Pr | H | H | H | 4-((4-CF$_3$—Bn)O) | m.p.: 190-191° C. |
| 1-343 | Me | Me | $^i$Pr | CO$_2$Me | H | H | 4-((4-CF$_3$—Bn)O) | viscous oil |
| 1-344 | Me | Me | $^i$Pr | CO$_2$Me | H | H | 4-(5-vinyl-1,2,4-oxadiazol-3-yl) | viscous oil |
| 1-345 | Me | Me | Et | H | H | H | 4-(5-CF$_3$-1,2,4-oxadiazol-3-yl) | m.p.: 196-197° C. |
| 1-346 | Me | Me | Et | CO$_2$Me | H | H | 4-(5-CF$_3$-1,2,4-oxadiazol-3-yl) | viscous oil |
| 1-347 | Me | Me | Et | H | H | H | 4-(5-CF$_2$CF$_3$-1,2,4-oxadiazol-3-yl) | m.p.: 206-207° C. |
| 1-348 | Me | Me | Et | CO$_2$Me | H | H | 4-(5-CF$_2$CF$_3$-1,2,4-oxadiazol-3-yl) | viscous oil |
| 1-349 | Me | Me | CHF$_2$ | H | H | H | 4-(5-CF$_3$-1,2,4-oxadiazol-3-yl) | m.p.: 265-267° C. |
| 1-350 | Me | Me | CHF$_2$ | CO$_2$Me | H | H | 4-(5-CF$_3$-1,2,4-oxadiazol-3-yl) | m.p.: 99-100° C. |
| 1-351 | Me | Me | Et | H | H | H | 4-(5-$^t$Bu-1,2,4-oxadiazol-3-yl) | m.p.: 250° C. up |
| 1-352 | Me | Me | Et | CO$_2$Me | H | H | 4-(5-$^t$Bu-1,2,4-oxadiazol-3-yl) | viscous oil |
| 1-353 | Me | Me | $^i$Pr | CO$_2$Me | H | H | 3-Bn-4-(O—CO$^t$Bu) | viscous oil |
| 1-354 | Me | Me | $^i$Pr | H | H | H | 3-Bn | m.p.: 223-225° C. |
| 1-355 | Me | Me | $^i$Pr | CO$_2$Me | H | H | 3-Bn | viscous oil |
| 1-356 | Me | Me | $^i$Pr | CO$_2$Me | H | H | 4-(5-$^t$Bu-1-$^n$Pr-1H-1,2,4-triazol-3-yl) | viscous oil |
| 1-357 | Me | Me | $^i$Pr | H | H | H | 4-Ac | m.p.: 196-197° C. |
| 1-358 | Me | Me | $^i$Pr | CO$_2$Me | H | H | 4-Ac | m.p.: 114-115° C. |
| 1-359 | Me | Me | Me | H | H | H | 4-(5-CF$_3$-1,2,4-oxadiazol-3-yl) | m.p.: 250° C. up |
| 1-360 | Me | Me | Me | CO$_2$Me | H | H | 4-(5-CF$_3$-1,2,4-oxadiazol-3-yl) | m.p.: 109-110° C. |
| 1-361 | Me | Me | Me | Ac | H | H | 4-(5-CF$_3$-1,2,4-oxadiazol-3-yl) | m.p.: 136-137° C. |
| 1-362 | Me | Me | $^i$Pr | CO$_2$Me | OMe | H | 4-OCF$_3$ | viscous oil |
| 1-363 | Me | Me | $^i$Pr | CO$_2$Me | OCO$_2$Me | H | 4-OCF$_3$ | viscous oil |
| 1-364 | Me | Me | $^i$Pr | H | H | H | 4-(5-$^t$Bu-1-Me-1H-1,2,4-triazol-3-yl) | m.p.: 300° C. up |
| 1-365 | Me | Me | $^i$Pr | CO$_2$Me | H | H | 4-(5-$^t$Bu-1-Me-1H-1,2,4-triazol-3-yl) | viscous oil |
| 1-366 | Me | Me | Me | H | H | H | 4-(5-CF$_2$CF$_3$-1,2,4-oxadiazol-3-yl) | m.p.: 250° C. up |
| 1-367 | Me | Me | Me | CO$_2$Me | H | H | 4-(5-CF$_2$CF$_3$-1,2,4-oxadiazol-3-yl) | m.p.: 115-116° C. |
| 1-368 | Me | Me | Me | H | H | H | 4-(5-$^t$Bu-1,2,4-oxadiazol-3-yl) | m.p.: 250° C. up |
| 1-369 | Me | Me | Me | CO$_2$Me | H | H | 4-(5-$^t$Bu-1,2,4-oxadiazol-3-yl) | viscous oil |
| 1-370 | Me | Me | $^i$Pr | CO$_2$Me | F | H | 4-OCF$_3$ | viscous oil |
| 1-371 | Me | Me | $^i$Pr | H | H | H | 4-(4-NO$_2$Ph) | m.p.: 235-236° C. |
| 1-372 | Me | Me | $^i$Pr | CO$_2$Me | H | H | 4-(4-NO$_2$Ph) | m.p.: 123-124° C. |
| 1-373 | Me | Me | $^i$Pr | H | H | H | 4-(4-CNPh) | m.p.: 249-250° C. |
| 1-374 | Me | Me | $^i$Pr | CO$_2$Me | H | H | 4-(4-CNPh) | viscous oil |
| 1-375 | Me | Me | $^i$Pr | H | H | H | 4-(4-SF$_5$Ph) | m.p.: 133-134° C. |
| 1-376 | Me | Me | $^i$Pr | CO$_2$Me | H | H | 4-(4-SF$_5$Ph) | viscous oil |
| 1-377 | Me | Me | $^i$Pr | CO$_2$Me | H | H | 4-(4-SCF$_3$Ph) | viscous oil |
| 1-378 | Me | Me | $^i$Pr | CO$_2$Me | H | H | 4-(4-SOCF$_3$Ph) | viscous oil |
| 1-379 | Me | Me | $^i$Pr | CO$_2$Me | H | H | 4-Br | viscous oil |
| 1-380 | Me | Me | $^i$Pr | CO$_2$Me | H | H | 4-(4-SCH$_3$Ph) | m.p.: 105-106° C. |
| 1-381 | Me | Me | $^i$Pr | CO$_2$Me | H | H | 4-(4-SOCH$_3$Ph) | amorphous |
| 1-382 | Me | Me | $^i$Pr | CO$_2$Me | H | H | 4-(4-SO$_2$CH$_3$Ph) | m.p.: 166-167° C. |
| 1-383 | Me | Me | $^i$Pr | H | H | H | 4-(3,4,5-F$_3$Ph) | m.p.: 242-243° C. |
| 1-384 | Me | Me | $^i$Pr | CO$_2$Me | H | H | 4-(3,4,5-F$_3$Ph) | viscous oil |
| 1-385 | Me | Me | $^i$Pr | H | H | H | 4-(4-AcPh) | m.p.: 220-221° C. |
| 1-386 | Me | Me | $^i$Pr | CO$_2$Me | H | H | 4-(4-AcPh) | m.p.: 125-126° C. |

TABLE 1-continued

| No. | $R^1$ | $R^2$ | $R^3$ | $R^4$ | $R^5$ | $R^6$ | $G^2$ | Physical Property |
|---|---|---|---|---|---|---|---|---|
| 1-387 | Me | Me | $^i$Pr | H | H | H | 4-(5-(4-Me$^c$Hex)-1-Me-1H-1,2,4-triazol-3-yl) | m.p.: 142-149° C. |
| 1-388 | Me | Me | $^i$Pr | CO$_2$Me | H | H | 4-(5-(4-Me$^c$Hex)-1-Me-1H-1,2,4-triazol-3-yl) | amorphous |
| 1-389 | Me | Me | $^i$Pr | CO$_2$Me | H | H | 4-CO$_2$Et | m.p.: 108-109° C. |
| 1-390 | Me | Me | $^i$Pr | CO$_2$Me | H | H | 4-(prop-1-en-2-yl) | viscous oil |
| 1-391 | Me | Me | $^i$Pr | H | H | H | 4-(2,4-Cl$_2$Ph) | m.p.: 250° C. up |
| 1-392 | Me | Me | $^i$Pr | CO$_2$Me | H | H | 4-(2,4-Cl$_2$Ph) | viscous oil |
| 1-393 | Me | Me | $^i$Pr | CO$_2$Me | H | H | 4-(4-SO$_2$CF$_3$Ph) | viscous oil |
| 1-394 | Me | Me | $^i$Pr | CO$_2$Me | H | H | 4-(4-(2-Me-1,3-dioxolan-2-yl)Ph) | viscous oil |
| 1-395 | Me | Me | $^i$Pr | CO$_2$Me | H | H | 4-(NHCOCH$_2$$^t$Bu) | viscous oil |
| 1-396 | Me | Me | $^i$Pr | CO$_2$Me | H | H | 4-(N(Me)COCH$_2$$^t$Bu) | viscous oil |
| 1-397 | Me | Me | $^i$Pr | Me | H | H | 4-(4-(C≡CH)Ph) | viscous oil |
| 1-398 | Me | Me | $^i$Pr | CO2Me | H | H | 4-(4-(C≡CH)Ph) | m.p.: 78-79° C. |
| 1-399 | Me | Me | CH(OH)CH$_3$ | CO2Me | H | H | 4-((4-OCF3Ph)O) | viscous oil |
| 1-400 | Me | Me | CH(OH)CH$_3$ | H | H | H | 4-((4-OCF3Ph)O) | m.p.: 197-198° C. |
| 1-401 | Me | Me | CH(O—CO$_2$CH$_3$)CH$_3$ | CO2Me | H | H | 4-((4-OCF3Ph)O) | viscous oil |
| 1-402 | Me | Me | Ac | CO2Me | H | H | 4-((4-OCF3Ph)O) | viscous oil |

TABLE 2 shows the substituents in the compound represented by formula (2).

[Chemical formula 37]

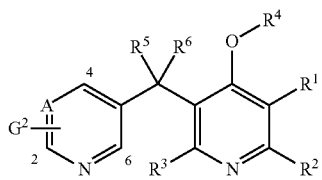

(2)

TABLE 2

| No. | $R^1$ | $R^2$ | $R^3$ | $R^4$ | $R^5$ | $R^6$ | A | $G^2$ | Physical Property |
|---|---|---|---|---|---|---|---|---|---|
| 2-1 | Me | Me | $^i$Pr | H | H | H | N | 2-(4-OCF$_3$Ph) | m.p.: 250° C. up |
| 2-2 | Me | Me | $^i$Pr | CO$_2$Me | H | H | N | 2-(4-OCF$_3$Ph) | m.p.: 129-130° C. |
| 2-3 | Me | Me | $^i$Pr | H | H | H | CH | 2-(5-CF$_3$-1,2,4-oxadiazol-3-yl) | m.p.: 222-224° C. |
| 2-4 | Me | Me | $^i$Pr | CO$_2$Me | H | H | CH | 2-(5-CF$_3$-1,2,4-oxadiazol-3-yl) | viscous oil |
| 2-5 | Me | Me | $^i$Pr | H | H | H | CH | 2-(3-CF$_2$CF$_3$-1,2,4-oxadiazol-5-yl) | m.p.: 201-203° C. |
| 2-6 | Me | Me | $^i$Pr | CO$_2$Me | H | H | CH | 2-(3-CF$_2$CF$_3$-1,2,4-oxadiazol-5-yl) | viscous oil |
| 2-7 | Br | Me | $^i$Pr | H | H | H | CH | 2-(3-CF$_2$CF$_3$-1,2,4-oxadiazol-5-yl) | m.p.: 270° C. up |
| 2-8 | Br | Me | $^i$Pr | CO$_2$Me | H | H | CH | 2-(3-CF$_2$CF$_3$-1,2,4-oxadiazol-5-yl) | viscous oil |
| 2-9 | Me | Me | $^i$Pr | H | H | H | CH | 2-(5-$^t$Bu-1,2,4-oxadiazol-3-yl) | m.p.: 145-153° C. |
| 2-10 | Me | Me | $^i$Pr | CO$_2$Me | H | H | CH | 2-(5-$^t$Bu-1,2,4-oxadiazol-3-yl) | viscous oil |
| 2-11 | Me | Me | $^i$Pr | Ac | H | H | CH | 2-(3-CF$_2$CF$_3$-1,2,4-oxadiazol-5-yl) | m.p.: 113-115° C. |
| 2-12 | Me | Me | $^i$Pr | H | H | H | CH | 2-(5-CF$_2$CF$_3$-1,2,4-oxadiazol-3-yl) | m.p.: 223-226° C. |
| 2-13 | Me | Me | $^i$Pr | CO$_2$Me | H | H | CH | 2-(5-CF$_2$CF$_3$-1,2,4-oxadiazol-3-yl) | viscous oil |
| 2-14 | Me | Me | $^i$Pr | Ac | H | H | CH | 2-(5-CF$_2$CF$_3$-1,2,4-oxadiazol-3-yl) | m.p.: 115-117° C. |
| 2-15 | Me | Me | $^i$Pr | CH$_2$OAc | H | H | CH | 2-(3-CF$_2$CF$_3$-1,2,4-oxadiazol-5-yl) | viscous oil |
| 2-16 | Me | Me | $^i$Pr | H | H | H | CH | 2-(3-CF$_3$-1,2,4-oxadiazol-5-yl) | m.p.: 218-220° C. |

TABLE 2-continued

| No. | R¹ | R² | R³ | R⁴ | R⁵ | R⁶ | A | G² | Physical Property |
|---|---|---|---|---|---|---|---|---|---|
| 2-17 | Me | Me | $^i$Pr | CO₂Me | H | H | CH | 2-(3-CF₃-1,2,4-oxadiazol-5-yl) | viscous oil |
| 2-18 | Me | Me | $^i$Pr | Ac | H | H | CH | 2-(3-CF₃-1,2,4-oxadiazol-5-yl) | m.p.: 128-130° C. |
| 2-19 | Me | Me | $^i$Pr | CO₂Me | H | H | CH | 2-(3-$^t$Bu-1,2,4-oxadiazol-5-yl) | viscous oil |
| 2-20 | Me | Me | $^i$Pr | Ac | H | H | CH | 2-(3-$^t$Bu-1,2,4-oxadiazol-5-yl) | viscous oil |
| 2-21 | Me | Me | $^i$Pr | H | H | H | CH | 2-(5-$^c$Hex-1,2,4-oxadiazol-3-yl) | m.p.: 195-196° C. |
| 2-22 | Me | Me | $^i$Pr | CO₂Me | H | H | CH | 2-(5-$^c$Hex-1,2,4-oxadiazol-3-yl) | m.p.: 123-124° C. |
| 2-23 | Me | Me | $^i$Pr | Me | H | H | CH | 2-Cl | viscous oil |
| 2-24 | Me | Me | $^i$Pr | H | H | H | CH | 2-(5-(4-Me-$^c$Hex)-1,2,4-oxadiazol-3-yl) | m.p.: 135-140° C. |
| 2-25 | Me | Me | $^i$Pr | CO₂Me | H | H | CH | 2-(5-(4-Me-$^c$Hex)-1,2,4-oxadiazol-3-yl) | viscous oil |
| 2-26 | Me | Me | $^i$Pr | H | H | H | N | 2-(5-$^t$Bu-1,2,4-oxadiazol-3-yl) | m.p.: 144-147° C. |
| 2-27 | Me | Me | $^i$Pr | CO₂Me | H | H | N | 2-(5-$^t$Bu-1,2,4-oxadiazol-3-yl) | m.p.: 37-43° C. |
| 2-28 | Me | Me | $^i$Pr | H | H | H | CH | 2-(naphthalen-2-yl) | m.p.: 209-211° C. |
| 2-29 | Me | Me | $^i$Pr | CO₂Me | H | H | CH | 2-(naphthalen-2-yl) | m.p.: 140-142° C. |
| 2-30 | Me | Me | $^i$Pr | H | H | H | CH | 4-(2-CF₃-quinolin-7-yl) | m.p.: 259-262° C. |
| 2-31 | Me | Me | $^i$Pr | CO₂Me | H | H | CH | 4-(2-CF₃-quinolin-7-yl) | m.p.: 165-167° C. |
| 2-32 | Me | Me | $^i$Pr | H | H | H | CH | 4-(dibenzo[b,d]thiophen-2-yl) | m.p.: 173-175° C. |
| 2-33 | Me | Me | $^i$Pr | CO₂Me | H | H | CH | 4-(dibenzo[b,d]thiophen-2-yl) | m.p.: 74-76° C. |
| 2-34 | Me | Me | $^i$Pr | CO2Me | H | H | CH | 2-(4-CF3—1H-imidazol-1-yl) | m.p.: 119-121° C. |
| 2-35 | Me | Me | $^i$Pr | CO2Me | H | H | CH | 2-(3-CF3—1H-pyrazol-1-yl) | m.p.: 107-110° C. |
| 2-36 | Me | Me | $^i$Pr | H | H | H | CH | 2-(5-CF2CF2CF3-1,2,4-oxadiazol-3-yl) | m.p.: 237-239° C. |
| 2-37 | Me | Me | $^i$Pr | CO2Me | H | H | CH | 2-(5-CF2CF2CF3-1,2,4-oxadiazol-3-yl) | viscous oil |

TABLE 3 shows the substituents in the compound represented by formula (3).

[Chemical formula 38]

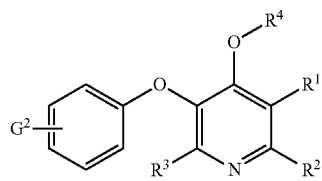

(3)

[Chemical formula 39]

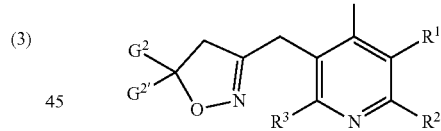

(4)

TABLE 3

| No. | R¹ | R² | R³ | R⁴ | G² | Physical Property |
|---|---|---|---|---|---|---|
| 3-1 | Br | Me | Me | H | 3-((4-OCF₃Ph)O) | m.p.: 236-239° C. |
| 3-2 | Me | Me | Me | Ac | 4-OCF₃ | viscous oil |
| 3-3 | Me | Me | Me | H | 4-OCF₃ | m.p.: 220° C. up |
| 3-4 | Br | Me | Me | Ac | 4-OCF₃ | viscous oil |
| 3-5 | Me | Me | Me | Ac | 4-((4-OCF₃Ph)O) | viscous oil |
| 3-6 | Me | Me | Me | H | 4-((4-OCF₃Ph)O) | m.p.: 200° C. up |
| 3-7 | Br | Me | Me | Ac | 4-((4-OCF₃Ph)O) | viscous oil |
| 3-8 | Me | Me | Me | Ac | 3-((4-OCF₃Ph)O) | viscous oil |
| 3-9 | Me | Me | Me | H | 3-((4-OCF₃Ph)O) | m.p.: 200° C. up |
| 3-10 | Br | Me | Me | Ac | 3-((4-OCF₃Ph)O) | viscous oil |

TABLE 4 shows the substituents in the compound represented by formula (4).

TABLE 4

| No. | R¹ | R² | R³ | R⁴ | G² | G²' | Physical Property |
|---|---|---|---|---|---|---|---|
| 4-1 | Me | Me | Me | Bn | 4-CF₃Ph | H | m.p.: 120-125° C. |
| 4-2 | Me | Me | Me | H | 4-CF₃Ph | H | m.p.: 200° C. up |
| 4-3 | Me | Me | Me | Ac | 4-CF₃Ph | H | viscous oil |
| 4-4 | Me | Me | Me | Bn | 4-CF₃Bn | H | m.p.: 84-88° C. |
| 4-5 | Me | Me | Me | H | 4-CF₃Bn | H | m.p.: 200° C. up |
| 4-6 | Me | Me | Me | Ac | 4-CF₃Bn | H | m.p.: 114-118° C. |
| 4-7 | Me | Me | Me | Bn | 3-CF₃Ph | CF₃ | m.p.: 40-45° C. |
| 4-8 | Me | Me | Me | H | 3-CF₃Ph | CF₃ | m.p.: 200° C. up |
| 4-9 | Me | Me | Me | Ac | 3-CF₃Ph | CF₃ | viscous oil |
| 4-10 | Me | Me | Me | Bn | 4-CF₃Ph | Me | m.p.: 88-92° C. |
| 4-11 | Me | Me | Me | H | 4-CF₃Ph | Me | m.p.: 200° C. up |
| 4-12 | Me | Me | Me | Ac | 4-CF₃Ph | Me | m.p.: 119-122° C. |
| 4-13 | Me | Me | Me | Bn | (3-Cl-5-CF₃-Py-2-yl)OCH₂CH₂ | H | m.p.: 65-69° C. |
| 4-14 | Me | Me | Me | H | (3-Cl-5-CF₃-Py-2-yl)OCH₂CH₂ | H | m.p.: 200° C. up |
| 4-15 | Me | Me | Me | Ac | (3-Cl-5-CF₃-Py-2-yl)OCH₂CH₂ | H | viscous oil |

TABLE 4-continued

| No. | R¹ | R² | R³ | R⁴ | G² | G²' | Physical Property |
|---|---|---|---|---|---|---|---|
| 4-16 | Me | Me | Me | Bn | (3-Cl-5-CF₃-Py-2-yl)OCH₂ | H | m.p.: 105-110° C. |
| 4-17 | Me | Me | Me | H | (3-Cl-5-CF₃-Py-2-yl)OCH₂ | H | m.p.: 200° C. up |
| 4-18 | Me | Me | Me | Ac | (3-Cl-5-CF₃-Py-2-yl)OCH₂ | H | m.p.: 120-124° C. |
| 4-19 | Me | Me | Me | Bn | CH₃(CH₂)₆CH₂ | H | viscous oil |
| 4-20 | Me | Me | Me | H | CH₃(CH₂)₆CH₂ | H | m.p.: 200° C. up |
| 4-21 | Me | Me | Me | Ac | CH₃(CH₂)₆CH₂ | H | m.p.: 39-41° C. |

TABLE 5 shows the substituents in the compound represented by formula (5).

[Chemical formula 40]

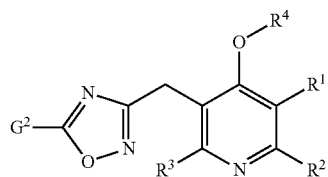

(5)

TABLE 5

| No. | R¹ | R² | R³ | R⁴ | G² | Physical Property |
|---|---|---|---|---|---|---|
| 5-1 | Me | Me | Me | H | 4-OCF₃Ph | m.p.: 200° C. up |
| 5-2 | Me | Me | Me | Ac | 4-OCF₃Ph | m.p.: 170-173° C. |
| 5-3 | Me | Me | Me | Ac | 4-CF₃Bn | m.p.: 95-98° C. |
| 5-4 | Me | Me | Me | H | (4-CF₃Ph)CH₂CH₂ | m.p.: 200° C. up |
| 5-5 | Me | Me | Me | Ac | (4-CF₃Ph)CH₂CH₂ | amorphous |

TABLE 6 shows the substituents in the compound represented by formula (6).

[Chemical formula 41]

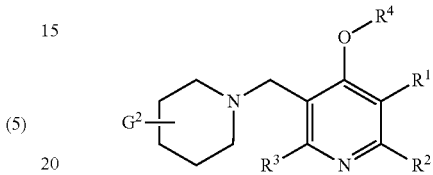

(6)

TABLE 6

| No. | R¹ | R² | R³ | R⁴ | G² | Physical Property |
|---|---|---|---|---|---|---|
| 6-1 | Me | Me | Me | Ac | 4-((3-CF₃Ph)O) | viscous oil |
| 6-2 | Me | Me | Me | H | 4-((3-CF₃Ph)O) | amorphous |
| 6-3 | Me | Me | Me | Allyl | 4-((3-CF₃Ph)O) | viscous oil |
| 6-4 | Me | Me | Me | Ac | 4-((4-OCF₃Ph)O) | viscous oil |
| 6-5 | Me | Me | Me | H | 4-((4-OCF₃Ph)O) | amorphous |
| 6-6 | Me | Me | Me | Ac | 4-(4-OCF₃Ph) | viscous oil |
| 6-7 | Me | Me | Me | H | 4-(4-OCF₃Ph) | m.p.: 200° C. up |

TABLE 7

| No. | Structure | Physical Property |
|---|---|---|
| 7-1 | 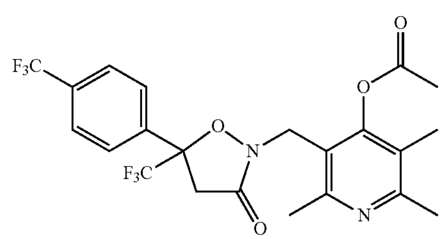 [SMILES: CC(=O)Oc1c(C)c(C)nc(C)c1CN1OC(c2ccc(C(F)(F)F)cc2)(C(F)(F)F)CC1=O] | viscous oil |
| 7-2 | 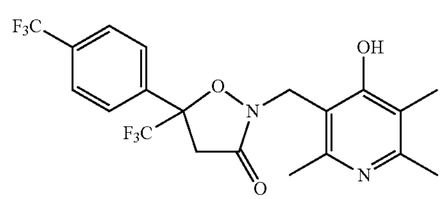 [SMILES: Cc1nc(C)c(CN2OC(c3ccc(C(F)(F)F)cc3)(C(F)(F)F)CC2=O)c(O)c1C] | viscous oil |
| 7-3 | 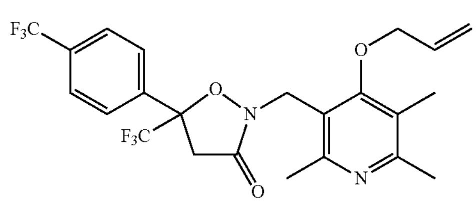 [SMILES: C=CCOc1c(C)c(C)nc(C)c1CN1OC(c2ccc(C(F)(F)F)cc2)(C(F)(F)F)CC1=O] | viscous oil |

TABLE 7-continued

| No. | Structure | Physical Property |
|---|---|---|
| 7-4 | 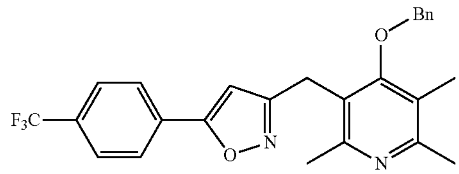 [SMILES: Cc1nc(C)c(Cc2cc(-c3ccc(C(F)(F)F)cc3)on2)c(OCc2ccccc2)c1C] | m.p.: 118-121° C. |
| 7-5 | 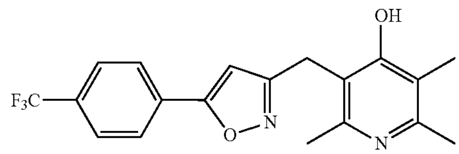 [SMILES: Cc1nc(C)c(Cc2cc(-c3ccc(C(F)(F)F)cc3)on2)c(O)c1C] | m.p.: 200° C. up |
| 7-6 | 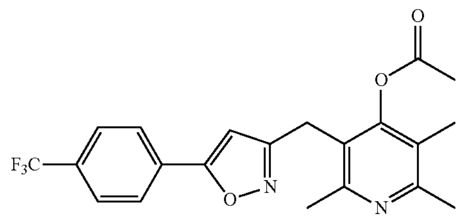 [SMILES: CC(=O)Oc1c(C)c(C)nc(C)c1Cc1cc(-c2ccc(C(F)(F)F)cc2)on1] | m.p.: 170-173° C. |
| 7-7 | 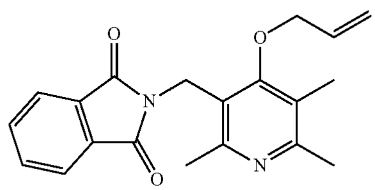 [SMILES: C=CCOc1c(C)c(C)nc(C)c1CN1C(=O)c2ccccc2C1=O] | m.p.: 145-147° C. |
| 7-8 | 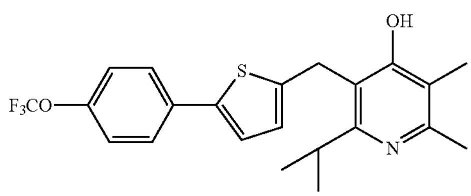 [SMILES: Cc1nc(C(C)C)c(Cc2ccc(-c3ccc(OC(F)(F)F)cc3)s2)c(O)c1C] | m.p.: 250° C. up |
| 7-9 | 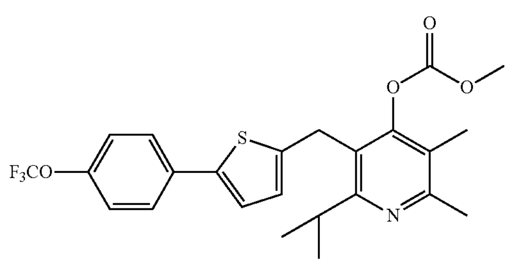 [SMILES: COC(=O)Oc1c(C)c(C)nc(C(C)C)c1Cc1ccc(-c2ccc(OC(F)(F)F)cc2)s1] | m.p.: 91-94° C. |
| 7-10 | 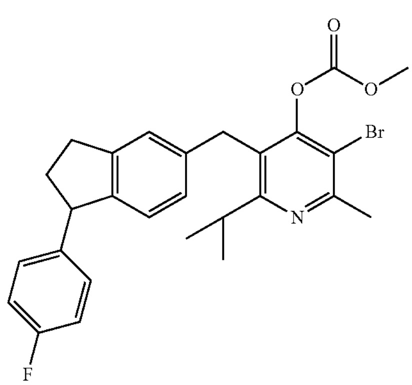 [SMILES: COC(=O)Oc1c(Br)c(C)nc(C(C)C)c1Cc1ccc2c(c1)CCC2c1ccc(F)cc1] | amorphous |

TABLE 7-continued

| No. | Structure | Physical Property |
|---|---|---|
| 7-11 | 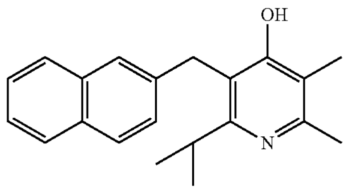 [SMILES: Cc1nc(C(C)C)c(Cc2ccc3ccccc3c2)c(O)c1C] | m.p.: 268-270° C. |
| 7-12 | 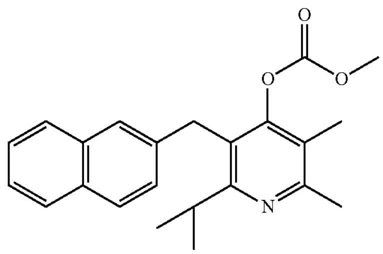 [SMILES: COC(=O)Oc1c(C)c(C)nc(C(C)C)c1Cc1ccc2ccccc2c1] | amorphous |
| 7-13 | 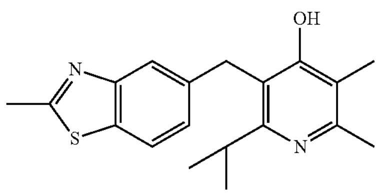 | m.p.: 284-286° C. |
| 7-14 | 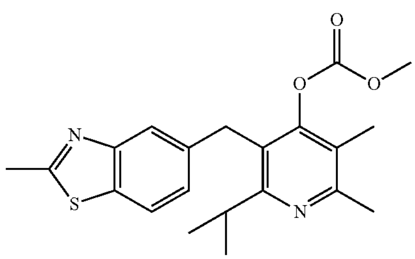 | $n_D(22.1° C.)$ 1.554 |
| 7-15 | 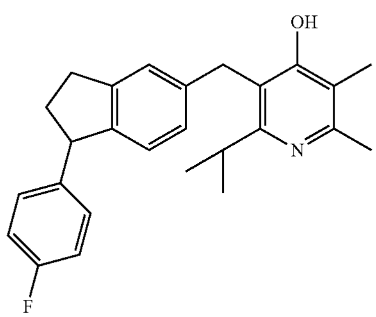 [SMILES: Cc1nc(C(C)C)c(Cc2ccc3c(c2)CCC3c2ccc(F)cc2)c(O)c1C] | m.p.: 260-262° C. |
| 7-16 | 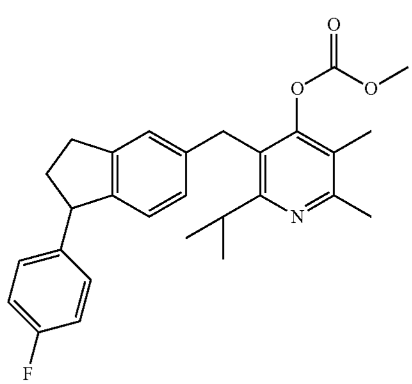 [SMILES: COC(=O)Oc1c(C)c(C)nc(C(C)C)c1Cc1ccc2c(c1)CCC2c1ccc(F)cc1] | $n_D(22.0° C.)$ 1.551 |

TABLE 7-continued

| No. | Structure | Physical Property |
|---|---|---|
| 7-17 | 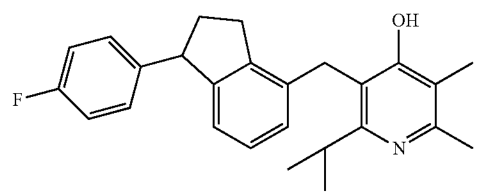 [SMILES: Cc1nc(C(C)C)c(Cc2cccc3c2CCC3c2ccc(F)cc2)c(O)c1C] | m.p.: 296-298° C. |
| 7-18 | 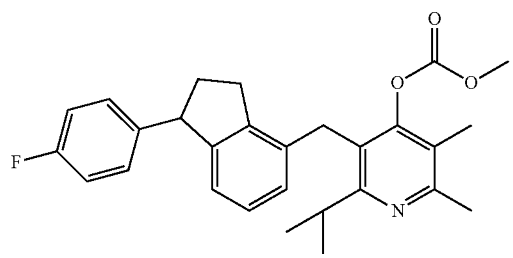 [SMILES: COC(=O)Oc1c(C)c(C)nc(C(C)C)c1Cc1cccc2c1CCC2c1ccc(F)cc1] | viscous oil |
| 7-19 | 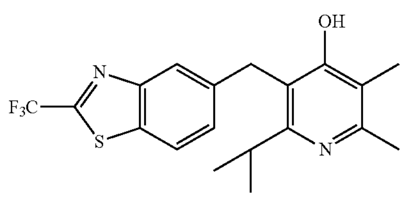 [SMILES: Cc1nc(C(C)C)c(Cc2ccc3sc(C(F)(F)F)nc3c2)c(O)c1C] | m.p.: 273-274° C. |
| 7-20 | 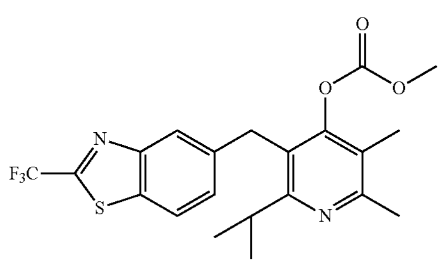 [SMILES: COC(=O)Oc1c(C)c(C)nc(C(C)C)c1Cc1ccc2sc(C(F)(F)F)nc2c1] | amorphous |
| 7-21 | 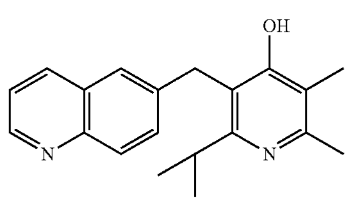 [SMILES: Cc1nc(C(C)C)c(Cc2ccc3ncccc3c2)c(O)c1C] | m.p.: 254-256° C. |
| 7-22 | 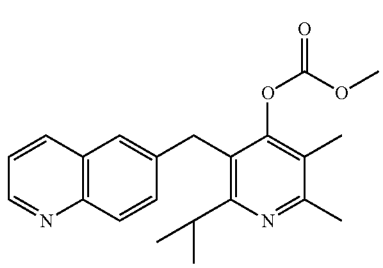 [SMILES: COC(=O)Oc1c(C)c(C)nc(C(C)C)c1Cc1ccc2ncccc2c1] | m.p.: 127-128° C. |

TABLE 7-continued

| No. | Structure | Physical Property |
|---|---|---|
| 7-23 | 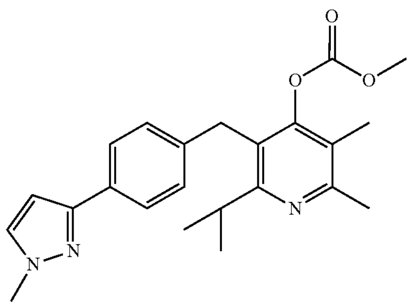 [SMILES: COC(=O)Oc1c(C)c(C)nc(C(C)C)c1Cc1ccc(-c2ccn(C)n2)cc1] | viscous oil |
| | | |
| 7-24 | 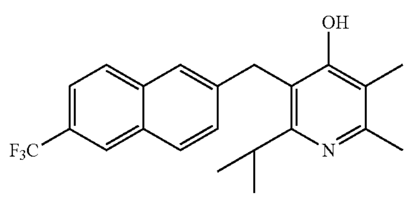 [SMILES: Cc1nc(C(C)C)c(Cc2ccc3cc(C(F)(F)F)ccc3c2)c(O)c1C] | m.p.: 268-269° C. |
| 7-25 | 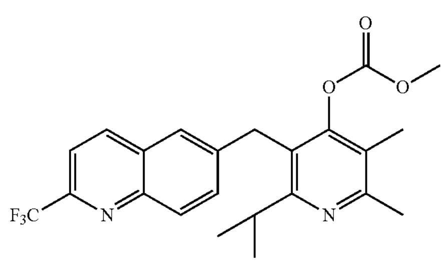 [SMILES: COC(=O)Oc1c(C)c(C)nc(C(C)C)c1Cc1ccc2nc(C(F)(F)F)ccc2c1] | m.p.: 139-140° C. |
| 7-26 | 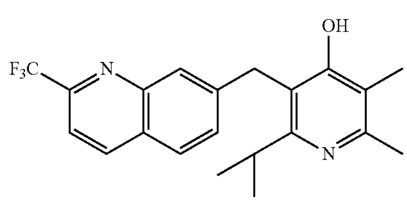 [SMILES: Cc1nc(C(C)C)c(Cc2ccc3ccc(C(F)(F)F)nc3c2)c(O)c1C] | m.p.: 290-292° C. |
| 7-27 | 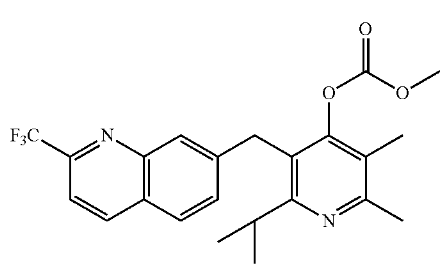 [SMILES: COC(=O)Oc1c(C)c(C)nc(C(C)C)c1Cc1ccc2ccc(C(F)(F)F)nc2c1] | m.p.: 125-126° C. |

TABLE 7-continued

| No. | Structure | Physical Property |
|---|---|---|
| 7-28 | 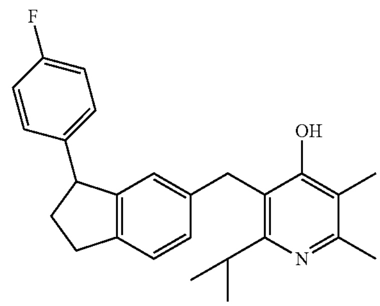 [SMILES: Cc1nc(C(C)C)c(Cc2ccc3c(c2)C(c2ccc(F)cc2)CC3)c(O)c1C] | m.p.: 221-224° C. |
| 7-29 | 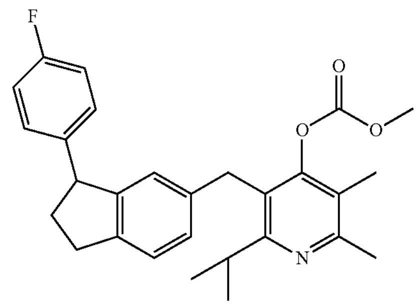 [SMILES: COC(=O)Oc1c(C)c(C)nc(C(C)C)c1Cc1ccc2c(c1)C(c1ccc(F)cc1)CC2] | viscous oil |
| 7-30 | 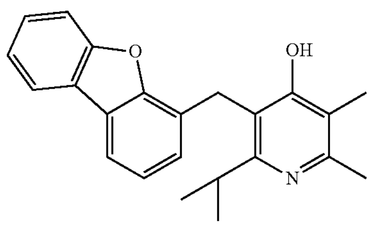 [SMILES: Cc1nc(C(C)C)c(Cc2cccc3c2oc2ccccc23)c(O)c1C] | m.p.: 300° C. up |
| 7-31 | 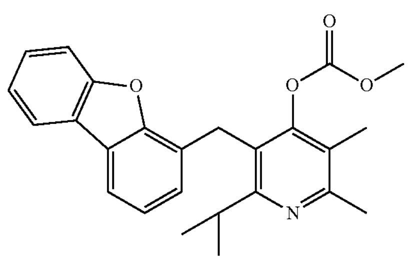 [SMILES: COC(=O)Oc1c(C)c(C)nc(C(C)C)c1Cc1cccc2c1oc1ccccc12] | m.p.: 114-116° C. |
| 7-32 | 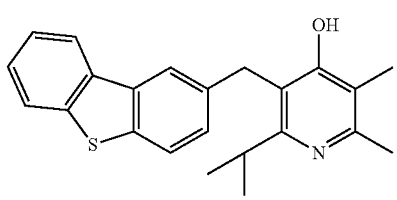 [SMILES: Cc1nc(C(C)C)c(Cc2ccc3sc4ccccc4c3c2)c(O)c1C] | m.p.: 300° C. up |
| 7-33 | 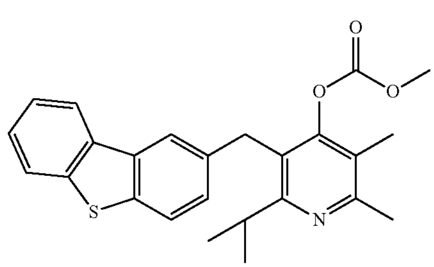 [SMILES: COC(=O)Oc1c(C)c(C)nc(C(C)C)c1Cc1ccc2sc3ccccc3c2c1] | m.p.: 154-155° C. |

TABLE 7-continued

| No. | Structure | Physical Property |
|---|---|---|
| 7-34 | 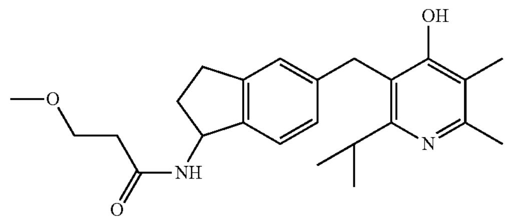 | m.p.: 115-120° C. |
| 7-35 | 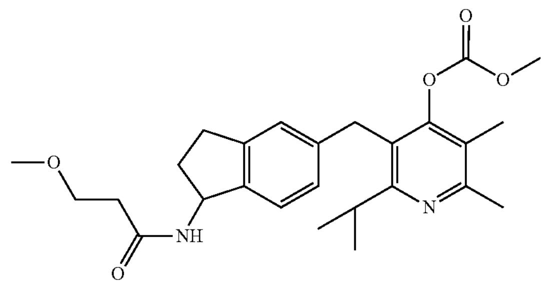 | amorphous |
| 7-36 | 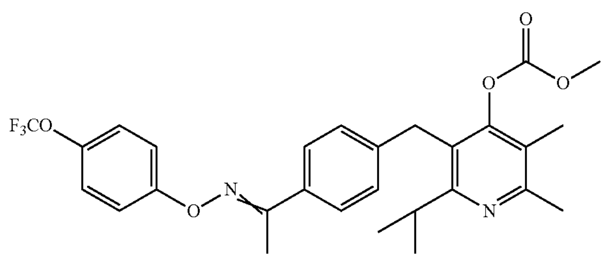 [SMILES: COC(=O)Oc1c(C)c(C)nc(C(C)C)c1Cc1ccc(C(C)=NOc2ccc(OC(F)(F)F)cc2)cc1] | $n_D$(19.5° C.) 1.539 |
| 7-37 | 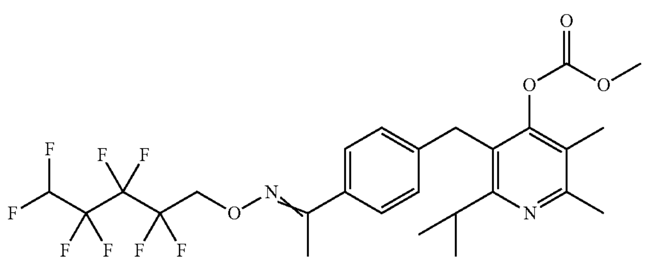 [SMILES: COC(=O)Oc1c(C)c(C)nc(C(C)C)c1Cc1ccc(C(C)=NOCC(F)(F)C(F)(F)C(F)(F)C(F)F)cc1] | $n_D$(19.6° C.) 1.486 |
| 7-38 | 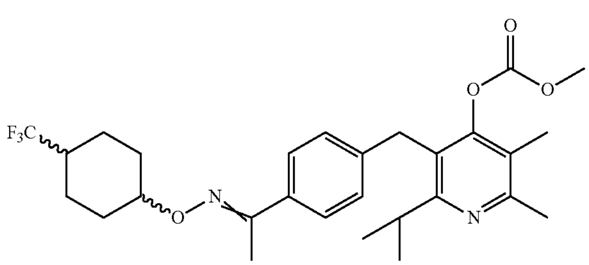 [SMILES: COC(=O)Oc1c(C)c(C)nc(C(C)C)c1Cc1ccc(C(C)=NOC2CCC(C(F)(F)F)CC2)cc1] | $n_D$(20.5° C.) 1.480 |
| 7-39 | 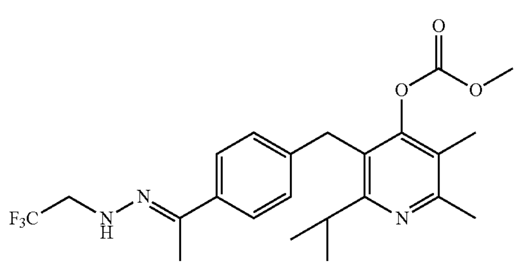 [SMILES: COC(=O)Oc1c(C)c(C)nc(C(C)C)c1Cc1ccc(/C(C)=N/NCC(F)(F)F)cc1] | $n_D$(20.7° C.) 1.522 |

TABLE 7-continued

| No. | Structure | Physical Property |
|---|---|---|
| 7-40 | 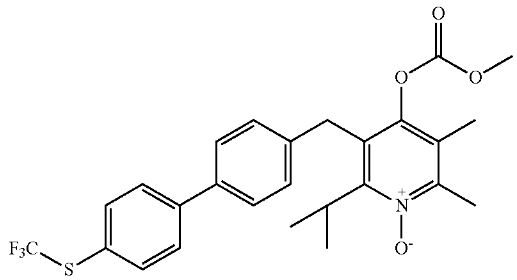 | viscous oil |
| 7-41 | 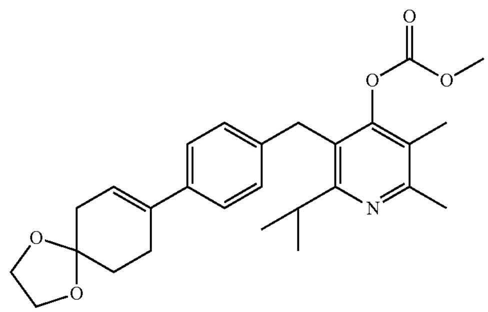 [SMILES: COC(=O)Oc1c(C)c(C)nc(C(C)C)c1Cc1ccc(C2=CCC3(CC2)OCCO3)cc1] | viscous oil |
| 7-42 | 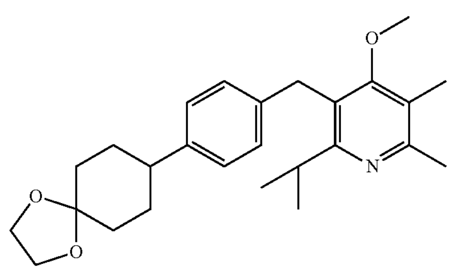 [SMILES: COc1c(C)c(C)nc(C(C)C)c1Cc1ccc(C2CCC3(CC2)OCCO3)cc1] | m.p.: 107-108° C. |
| 7-43 | 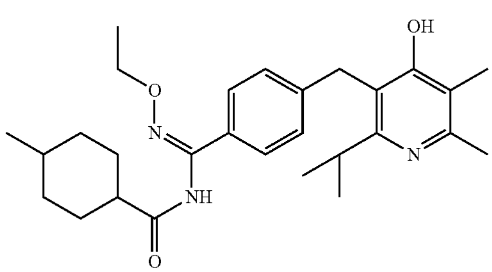 | m.p.: 101-115° C. |

TABLE 7-continued

| No. | Structure | Physical Property |
|---|---|---|
| 7-44 | 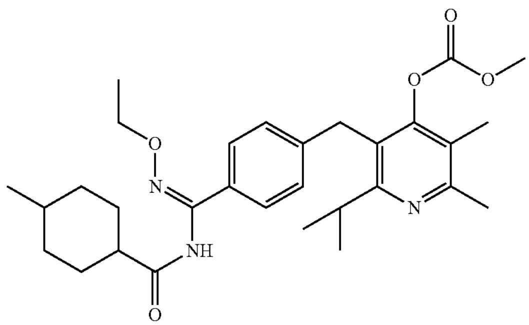 | viscous oil |
| 7-45 | 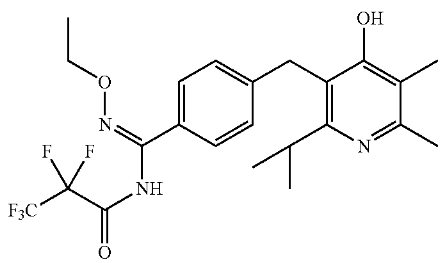 [SMILES: CCO/N=C(/NC(=O)C(F)(F)C(F)(F)F)c1ccc(Cc2c(C(C)C)nc(C)c(C)c2O)cc1] | m.p.: 210-212° C. |
| 7-46 | 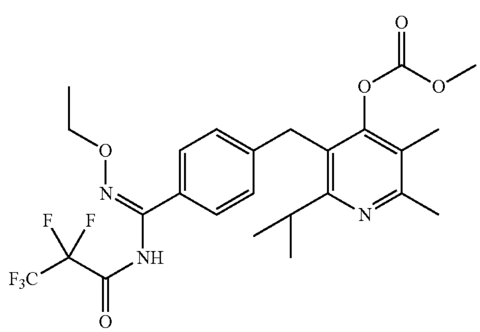 [SMILES: CCO/N=C(/NC(=O)C(F)(F)C(F)(F)F)c1ccc(Cc2c(C(C)C)nc(C)c(C)c2OC(=O)OC)cc1] | m.p.: 98-100° C. |
| 7-47 | 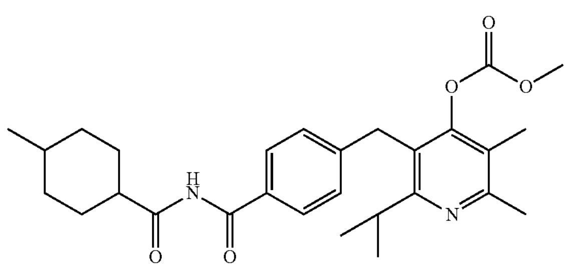 | m.p.: 169-171° C. |
| 7-48 | 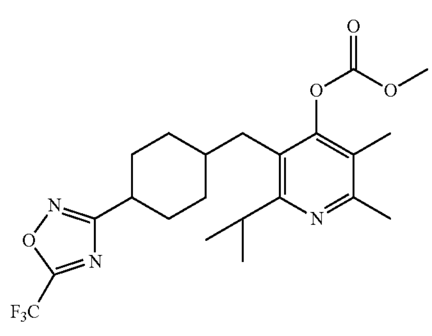 [SMILES: COC(=O)Oc1c(C)c(C)nc(C(C)C)c1CC1CCC(c2noc(C(F)(F)F)n2)CC1] | viscous oil |

TABLE 7-continued

| No. | Structure | Physical Property |
|---|---|---|
| 7-49 | 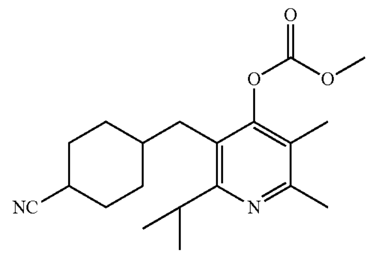 [SMILES: COC(=O)Oc1c(C)c(C)nc(C(C)C)c1CC1CCC(C#N)CC1] | viscous oil |
| 7-50 | 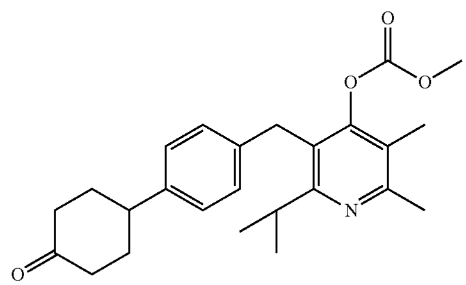 [SMILES: COC(=O)Oc1c(C)c(C)nc(C(C)C)c1Cc1ccc(C2CCC(=O)CC2)cc1] | viscous oil |
| 7-51 | 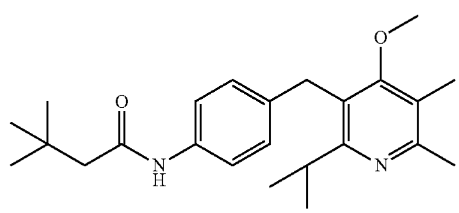 [SMILES: COc1c(C)c(C)nc(C(C)C)c1Cc1ccc(NC(=O)CC(C)(C)C)cc1] | m.p.: 154-155° C. |
| 7-52 | 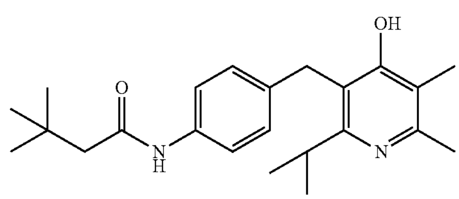 [SMILES: Cc1nc(C(C)C)c(Cc2ccc(NC(=O)CC(C)(C)C)cc2)c(O)c1C] | m.p.: 300° C. up |
| 7-53 | 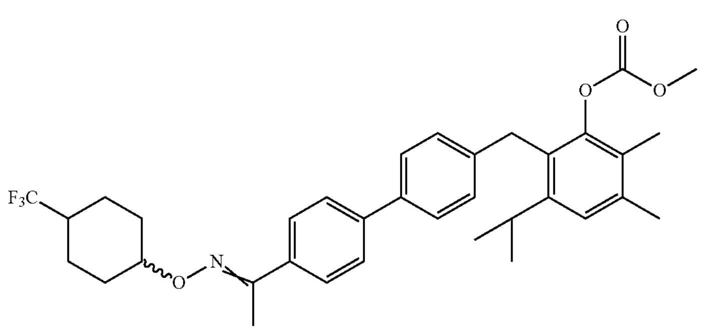 [SMILES: COC(=O)Oc1c(C)c(C)cc(C(C)C)c1Cc1ccc(-c2ccc(C(C)=NOC3CCC(C(F)(F)F)CC3)cc2)cc1] | m.p.: 58-59° C. |

The ¹H-NMR data of some of the compounds listed in the above TABLES 1 to 7 are shown in TABLE 8.

TABLE 8

| No. | 1H-NMR data (δppm) |
|---|---|
| 1-2 | 2.19 (s, 3H), 3.81 (s, 3H), 3.88 (s, 2H), 5.47 (s, 2H), 6.26 (d, 1H), 6.92-7.51 (m, 9H), 8.31 (d, 1H) |
| 1-3 | 2.10 (s, 3H), 2.48 (s, 3H), 2.51 (s, 3H), 3.79 (s, 3H), 3.92 (s, 2H), 6.89-6.97 (m, 4H), 7.08 (d, 2H), 7.15 (d, 2H) |
| 1-4 | (CD$_3$OD) 2.05 (s, 3H), 2.39 (s, 3H), 2.79 (s, 6H), 3.97 (s, 2H), 6.90-7.26 (m, 8H) |
| 1-5 | 2.00 (s, 3H), 2.44 (s, 3H), 2.76 (s, 6H), 3.71 (s, 3H), 3.97 (s, 2H), 6.87-7.15 (m, 8H) |
| 1-6 | (DMSO-d$_6$): 1.85 (s, 3H), 2.18 (s, 3H), 2.19 (s, 3H), 3.74 (s, 2H), 6.92-7.04 (m, 4H), 7.22 (d, 2H), 7.34 (d, 2H), 10.85 (br.s, 1H) |
| 1-7 | (CD$_3$OD): 2.08 (s, 3H), 2.37 (s, 3H), 4.03 (s, 2H), 6.89-6.99 (m, 4H), 7.20 (d, 2H), 7.30 (d, 2H) |
| 1-9 | 1.17 (d, 6H), 2.08 (s, 3H), 2.51 (s, 3H), 3.19-3.22 (m, 1H), 3.76 (s, 3H), 3.95 (s, 2H), 6.89-6.94 (m, 4H), 7.06-7.15 (m, 4H) |
| 1-10 | 1.30 (s, 9H), 2.25 (s, 3H), 2.50 (s, 3H), 3.28 (s, 3H), 4.10-4.35 (m, 4H), 4.72 (d, 1H), 5.22-5.37 (m, 2H), 5.95-6.02 (m, 1H), 6.28 (d, 1H), 7.22 (d, 2H), 7.32 (d, 2H) |
| 1-12 | (DMSO-d$_6$): 1.97 (s, 3H), 2.39 (s, 3H), 4.16 (s, 2H), 6.92-7.04 (m, 4H), 7.21-7.36 (m, 4H) |
| 1-13 | 2.48 (s, 3H), 2.49 (s, 3H), 4.02 (s, 2H), 5.09 (s, 2H), 6.63 (s, 1H), 6.87-6.96 (m, 4H), 7.08-7.15 (m, 4H), 7.26-7.33 (m, 5H) |
| 1-14 | (CD$_3$OD) 2.28 (s, 3H), 2.30 (s, 3H), 3.90 (s, 2H), 6.25 (s, 1H), 6.89-7.00 (m, 4H), 7.19-7.23 (m, 4H) |
| 1-15 | (CD$_3$OD) 2.30 (s, 3H), 2.58 (s, 3H), 3.96 (s, 2H), 6.89-7.00 (m, 4H), 7.19-7.23 (m, 4H) |
| 1-16 | 2.49 (s, 3H), 2.77 (s, 3H), 3.84 (s, 3H), 3.97 (s, 2H), 6.90-6.97 (m, 4H), 7.07-7.17 (m, 4H) |
| 1-18 | 1.58 (s, 6H), 2.08 (s, 3H), 2.56 (s, 3H), 3.63 (s, 3H), 4.13 (s, 2H), 6.89-6.98 (m, 4H), 7.02-7.16 (m, 4H) |
| 1-21 | 2.10 (s, 3H), 2.57 (s, 3H), 3.71 (s, 3H), 3.93 (s, 3H), 4.34 (s, 2H), 6.62 (d, 1H), 6.84-7.37 (m, 9H) |
| 1-23 | 2.05 (s, 3H), 2.63 (s, 3H), 2.69 (s, 3H), 3.74 (s, 3H), 4.31 (s, 2H), 6.87 (d, 2H), 6.93 (d, 2H)., 7.13-7.17 (m, 4H) |
| 1-26 | (CD$_3$OD) 1.16 (d, 6H), 2.05 (s, 3H), 2.40 (s, 3H), 3.25-3.32 (m, 1H), 4.07 (s, 2H), 7.23 (d, 2H), 7.30 (d, 2H), 7.49 (d, 2H), 7.65 (d, 2H) |
| 1-27 | 1.16 (d, 6H), 2.05 (s, 3H), 2.52 (s, 3H), 3.18-3.28 (m, 1H), 3.72 (s, 3H), 4.01 (s, 2H), 7.18 (d, 2H), 7.25 (d, 2H), 7.43 (d, 2H), 7.53 (d, 2H) |
| 1-28 | (CD$_3$OD) 1.14 (d, 6H), 2.05 (s, 3H), 2.39 (s, 3H), 3.18-3.26 (m, 1H), 3.99 (s, 2H), 7.11 (d, 2H), 7.20 (d, 2H) |
| 1-33 | 1.16 (d, 6H), 2.05 (s, 3H), 2.52 (s, 3H), 3.18-3.28 (m, 1H), 3.72 (s, 3H), 4.01 (s, 2H), 7.18-7.79 (m, 8H) |
| 1-36 | (CD$_3$OD) 1.16 (d, 6H), 2.06 (s, 3H), 2.35 (s, 3H), 2.40 (s, 3H), 3.25-3.35 (m, 1H) 4.05 (s, 2H), 7.17-7.45 (m, 8H) |
| 1-37 | 1.16 (d, 6H), 2.05 (s, 3H), 2.37 (s, 3H), 2.52 (s, 3H), 3.18-3.28 (m, 1H), 3.69 (s, 3H), 4.00 (s, 2H), 7.13 (d, 2H), 7.22 (d, 2H), 7.44-7.47 (m, 4H) |
| 1-39 | 2.72 (s, 3H), 3.66 (s, 3H), 4.24 (s, 2H), 6.75 (t, 1H), 7.22-7.26 (m, 4H) 7.45 (d, 2H), 7.54 (d, 2H) |
| 1-40 | 2.10 (s, 3H), 2.56 (s, 3H), 3.60 (s, 3H), 4.09 (s, 2H), 6.77 (t, 1H), 7.22-7.26 (m, 4H) 7.42 (d, 2H), 7.54 (d, 2H) |
| 1-42 | 1.16 (d, 6H), 1.44 (d, 6H), 2.10 (s, 3H), 2.54 (s, 3H), 3.12-3.22 (m, 1H), 3.25 (m, 1H), 3.69 (s, 3H), 4.02 (s, 2H), 7.19 (d, 2H), 7.95 (d, 2H) |
| 1-44 | 1.16 (d, 6H), 2.09 (s, 3H), 2.53 (s, 3H), 3.09-3.19 (m, 1H), 3.73 (s, 3H), 4.04 (s, 2H), 7.23 (d, 2H), 7.99 (d, 2H) |
| 1-45 | (CD$_3$OD): 1.16 (d, 6H), 1.26 (d, 6H), 2.06 (s, 3H), 2.41 (s, 3H), 2.87-2.97 (m, 1H), 3.20-3.30 (m, 1H), 4.01 (s, 2H), 7.19 (d, 2H), 7.26 (d, 2H), 7.44-7.48 (m, 4H) |
| 1-46 | 1.18 (d, 6H), 1.26 (d, 6H), 2.09 (s, 3H), 2.53 (s, 3H), 2.87-2.97 (m, 1H), 3.18-3.27 (m, 1H), 3.69 (s, 3H), 4.05 (s, 2H), 7.13 (d, 2H), 7.28 (d, 2H), 7.46 (d, 2H), 7.51 (d, 2H) |
| 1-47 | (CD$_3$OD): 1.16 (d, 6H), 1.24 (t, 3H), 2.01 (s, 3H), 2.40 (s, 3H), 2.65 (q, 2H), 3.25 (m, 1H), 4.05 (s, 2H), 7.18-7.48 (m, 8H) |
| 1-49 | 1.17 (d, 6H), 2.70 (s, 3H), 3.17-3.27 (m, 1H), 3.80 (s, 3H), 4.05 (s, 2H), 7.17 (d, 2H), 7.22 (d, 2H), 7.46 (d, 2H), 7.57 (d, 2H) |
| 1-50 | 1.16 (d, 6H), 2.68 (s, 3H), 3.17-3.27 (m, 1H), 3.74 (s, 3H), 4.08 (s, 2H), 7.08-7.56 (m, 8H) |
| 1-53 | (CD$_3$OD): 1.19 (d, 6H), 2.04 (s, 3H), 2.44 (s, 3H), 2.49 (s, 3H), 3.00-3.08 (m, 1H), 3.97 (s, 2H), 6.86 (d, 1H), 7.27 (d, 2H), 7.41 (s, 1H) |
| 1-54 | 1.17 (d, 6H), 2.08 (s, 3H), 2.47 (s, 3H), 2.54 (s, 3H), 2.95-3.05 (m, 1H), 3.60 (s, 3H), 3.90 (s, 2H), 6.76 (d, 1H), 7.23 (d, 2H), 7.38 (s, 1H) |
| 1-56 | 1.13 (d, 6H), 2.08 (s, 3H), 2.32 (s, 3H), 2.54 (s, 3H), 3.10-3.20 (m, 1H), 3.71 (s, 3H), 3.99 (s, 2H), 7.00-7.20 (m, 3H) |
| 1-58 | (CD$_3$OD): 1.17 (d, 6H), 2.57 (s, 3H), 3.29-3.39 (m, 1H), 4.09 (s, 2H), 7.24 (d, 2H), 7.30 (d, 2H), 7.50 (d, 2H), 7.65 (d, 2H) |
| 1-60 | (CD$_3$OD): 1.23 (d, 6H), 2.22 (s, 3H), 2.60 (s, 3H), 3.33-3.43 (m, 1H), 4.25 (s, 2H), 7.36 (d, 2H), 8.05 (d, 2H) |
| 1-61 | 1.17 (d, 6H), 2.10 (s, 3H), 2.54 (s, 3H), 3.10-3.19 (m, 1H), 3.75 (s, 3H), 4.05 (s, 2H), 7.23 (d, 2H), 8.01 (d, 2H) |

TABLE 8-continued

| No. | 1H-NMR data (δppm) |
|---|---|
| 1-64 | (CD$_3$OD): 1.16 (d, 6H), 2.06 (s, 3H), 2.41 (s, 3H), 3.20-3.29 (m, 1H), 4.13 (s, 2H), 7.40 (d, 2H), 7.98 (d, 2H) |
| 1-65 | 1.16 (d, 6H), 2.09 (s, 3H), 2.54 (s, 3H), 3.07-3.17 (m, 1H), 3.75 (s, 3H), 4.06 (s, 2H), 7.28 (d, 2H), 8.00 (d, 2H) |
| 1-66 | (CD$_3$OD): 1.27 (d, 6H), 2.27 (s, 3H), 2.65 (s, 3H), 3.45-3.55 (m, 1H), 4.26 (s, 2H), 7.43-7.98 (m, 4H) |
| 1-67 | 1.18 (d, 6H), 2.09 (s, 3H), 2.54 (s, 3H), 3.12-3.22 (m, 1H), 3.74 (s, 3H), 4.06 (s, 2H), 7.24-7.95 (m, 4H) |
| 1-69 | (CD$_3$OD): 1.27 (d, 6H), 2.21 (s, 3H), 2.59 (s, 3H), 3.26-3.36 (m, 1H), 4.25 (s, 2H), 7.15-8.02 (m, 3H) |
| 1-70 | 1.18 (d, 6H), 2.11 (s, 3H), 2.55 (s, 3H), 3.07-3.17 (m, 1H), 3.79 (s, 3H), 4.05 (s, 2H), 6.99-8.00 (m, 3H) |
| 1-73 | 1.16 (d, 6H), 1.44 (d, 6H), 2.10 (s, 3H), 2.53 (s, 3H), 3.08-3.14 (m, 1H), 3.24-3.34 (m, 1H), 3.78 (s, 3H), 4.02 (s, 2H), 6.92-7.95 (m, 3H) |
| 1-74 | (CD$_3$OD): 1.17 (d, 6H), 2.04 (s, 3H), 2.40 (s, 3H), 3.11-3.21 (m, 1H), 4.08 (s, 2H), 7.12-7.99 (m, 3H) |
| 1-79 | 1.19 (d, 6H), 2.08 (s, 3H), 2.52 (s, 3H), 3.25 (m, 1H), 3.69 (s, 3H), 4.05 (s, 2H), 7.10 (d, 1H), 7.32-7.36 (m, 2H), 7.40 (d, 1H), 7.53-7.57 (m, 2H), 7.72 (d, 1H), 7.80 (s, 1H). |
| 1-81 | 1.13 (d, 6H), 2.08 (s, 3H), 2.51 (s, 3H), 3.18 (m, 1H), 3.74 (s, 3H), 4.01 (s, 2H), 7.04 (s, 1H), 7.12 (dd, 2H), 7.26 (m, 2H), 7.44 (t, 1H), 7.53 (t, 1H), 7.71 (d, 1H). |
| 1-83 | 1.09 (d, 6H), 2.04 (s, 3H), 2.50 (s, 3H), 2.92 (m, 1H), 3.67 (s, 3H), 3.81 (s, 2H), 6.85 (d, 1H), 7.20-7.23 (m, 3H), 7.51 (d, 2H), 7.72 (d, 2H). |
| 1-86 | 1.08 (d, 6H), 2.04 (s, 3H), 2.50 (s, 3H), 2.90 (m, 1H), 3.70 (s, 3H), 3.80 (s, 2H), 6.86 (d, 1H), 7.19-7.23 (m, 3H), 7.57 (d, 2H), 7.63 (m, 2H). |
| 1-88 | 1.11 (dd, 6H), 2.06 (s, 3H), 2.52 (s, 3H), 2.92 (m, 1H), 3.57 (s, 2H), 3.71 (s, 3H), 6.70 (m, 1H), 7.14-7.22 (m, 3H), 7.37 (d, 1H), 7.51 (t, 1H), 7.61 (t, 1H), 7.81 (d, 1H). |
| 1-90 | 1.19 (d, 6H), 2.09 (s, 3H), 2.54 (s, 3H), 3.21 (m, 1H), 3.72 (s, 3H), 4.03 (s, 2H), 7.19 (d, 2H), 7.48 (d, 2H), 7.63-7.65 (m, 4H). |
| 1-100 | 1.18 (d, 6H), 2.08 (s, 3H), 2.52 (s, 3H), 3.23 (m, 1H), 3.67 (s, 3H), 4.04 (s, 2H), 7.11 (d, 1H), 7.34 (m, 2H), 7.40 (d, 1H), 7.65 (m, 4H). |
| 1-109 | 1.15 (d, 6H), 2.09 (s, 3H), 2.52 (s, 3H), 2.75 (s, 3H), 3.19 (m, 1H), 3.71 (s, 3H), 3.99 (s, 2H), 7.11 (d, 2H), 7.23 (s, 1H), 7.75 (d, 2H). |
| 1-110 | (CD$_3$OD)1.16 (d, 6H), 2.07 (s, 3H), 2.41 (s, 3H), 3.24-3.34 (m, 1H), 4.10 (s, 2H), 7.30 (d, 2H), 7.97 (d, 2H), 8.01 (d, 1H), 8.12 (d, 1H), 8.87 (s, 1H). |
| 1-113 | 1.16 (d, 6H), 2.09 (s, 3H), 2.53 (s, 3H), 2.69 (s, 3H), 3.11-3.21 (m, 1H), 3.72 (s, 3H), 4.02 (s, 2H), 7.19 (d, 2H), 7.93 (d, 2H) |
| 1-115 | 1.16 (d, 6H), 1.45 (t, 3H), 2.09 (s, 3H), 2.53 (s, 3H), 2.96 (q, 2H), 3.11-3.21 (m, 1H), 3.72 (s, 3H), 4.02 (s, 2H), 7.19 (d, 2H), 7.95 (d, 2H) |
| 1-117 | 1.16 (d, 6H), 1.47 (s, 9H), 2.09 (s, 3H), 2.53 (s, 3H), 3.11-3.21 (m, 1H), 3.72 (s, 3H), 4.02 (s, 2H), 7.17 (d, 2H), 7.95 (d, 2H) |
| 1-119 | 1.17 (d, 6H), 2.09 (s, 3H), 2.49 (s, 3H), 2.53 (s, 3H), 2.92-2.99 (m, 1H), 3.72 (s, 3H), 3.93 (s, 2H), 6.79 (d, 1H), 7.76 (d, 1H), 7.93 (s, 1H) |
| 1-131 | 1.17 (d, 6H), 2.08 (s, 3H), 2.53 (s, 3H), 3.17 (m, 1H), 3.73 (s, 3H), 3.99 (s, 2H), 7.14 (d, 2H), 7.29 (s, 1H), 7.52 (d, 2H), 7.88 (s, 1H). |
| 1-133 | 1.14 (d, 6H), 1.32 (s, 12H), 2.08 (s, 3H), 2.52 (s, 3H), 3.14 (m, 1H), 3.71 (s, 3H), 3.98 (s, 2H), 7.07 (d, 2H), 7.66 (d, 2H). |
| 1-139 | 1.16 (d, 6H), 2.09 (s, 3H), 2.53 (s, 3H), 3.11-3.21 (m, 1H), 3.72 (s, 3H), 4.02 (s, 2H), 6.85 (t, 1H), 7.23 (d, 2H), 7.99 (d, 2H) |
| 1-141 | 1.17 (d, 6H), 2.09 (s, 3H), 2.49 (s, 3H), 2.53 (s, 3H), 2.91-2.99 (m, 1H), 3.72 (s, 3H), 3.93 (s, 2H), 6.80 (d, 1H), 7.77 (d, 1H), 7.94 (s, 1H) |
| 1-142 | (CD$_3$OD): 1.18 (d, 6H), 1.42 (d, 6H), 2.05 (s, 3H), 2.43 (s, 3H), 2.48 (s, 3H), 3.00-3.08 (m, 1H), 3.29-3.39 (m, 1H), 3.99 (s, 2H), 6.81 (d, 1H), 7.67 (d, 1H), 7.85 (s, 1H) |
| 1-143 | 1.17 (d, 6H), 1.44 (d, 6H), 2.09 (s, 3H), 2.46 (s, 3H), 2.55 (s, 3H), 2.90-3.00 (m, 1H), 3.22-3.32 (m, 1H), 3.72 (s, 3H), 3.93 (s, 2H), 6.73 (d, 1H), 7.71 (d, 1H), 7.88 (s, 1H) |
| 1-145 | (CD$_3$OD): 1.14 (d, 6H), 2.05 (s, 3H), 2.40 (s, 3H), 3.13-3.23 (m, 1H), 4.08 (s, 2H), 7.32 (d, 2H), 7.57 (d, 2H) |
| 1-148 | 1.16 (d, 6H), 2.25 (s, 3H), 2.50 (s, 3H), 3.02-3.12 (m, 1H), 4.14 (s, 2H), 4.70 (s, 2H), 7.20-7.38 (m, 5H), 7.80 (d, 2H), 7.99 (d, 2H), 8.73 (s, 1H) |
| 1-152 | 1.19 (d, 6H), 2.07 (s, 3H), 2.41 (s, 3H), 2.52 (s, 3H), 3.26 (sep, 1H), 3.66 (s, 3H), 4.03 (s, 2H), 7.02 (d, 1H), 7.15 (d, 1H), 7.26-7.40 (m, 12H) |
| 1-157 | 1.16 (d, 6H), 2.10 (s, 3H), 2.54 (s, 3H), 3.10 (m, 1H), 3.75 (s, 3H), 4.07 (s, 2H), 7.29 (d, 2H), 8.06 (d, 2H). |
| 1-159 | 1.16 (d, 6H), 2.09 (s, 3H), 2.54 (s, 3H), 3.10 (m, 1H), 3.75 (s, 3H), 4.07 (s, 2H), 7.29 (d, 2H), 8.07 (d, 2H). |
| 1-161 | 1.16 (d, 6H), 2.10 (s, 3H), 2.53 (s, 3H), 3.13 (m, 1H), 3.76 (s, 3H), 4.00 (s, 3H), 4.05 (s, 2H), 7.25 (d, 2H), 7.59 (d, 2H). |
| 1-163 | 1.16 (d, 6H), 2.10 (s, 3H), 2.53 (s, 3H), 3.12 (m, 1H), 3.77 (s, 3H), 4.02 (s, 3H), 4.05 (s, 2H), 7.24 (d, 2H), 7.58 (d, 2H). |
| 1-164 | (CD$_3$OD): 1.15 (d, 6H), 2.04, 2.06 (s, 3H), 2.40 (s, 3H), 3.16-3.30 (m, 1H), 4.07 (s, 2H), 7.30-7.96. (m, 4H), 9.21 (s, 0.4H) |
| 1-166 | 1.10-1.13 (m, 12H), 2.17 (s, 3H), 2.37-2.47 (m, 1H), 2.51 (s, 3H), 3.00-3.08 (m, 1H), 4.16 (s, 2H), 5.50 (s, 2H), 7.22 (d, 2H), 7.99 (d, 2H) |
| 1-169 | (CD$_3$OD) 1.17 (d, 6H), 2.34 (s, 3H), 2.57 (s, 3H), 3.31 (m, 1H), 4.07 (s, 2H), 7.20 (d, 4H), 7.45 (m, 4H), 7.90 (s, 1H). |

TABLE 8-continued

| No. | 1H-NMR data (δppm) |
|---|---|
| 1-170 | 1.17 (d, 6H), 2.38 (s, 3H), 2.68 (s, 3H), 3.23 (m, 1H), 3.76 (s, 3H), 4.05 (s, 2H), 7.13 (d, 2H), 7.22 (d, 2H), 7.44-7.48 (m, 4H). |
| 1-175 | 0.86 (t, 3H), 0.94 (d, 3H), 1.14 (d, 6H), 1.17-1.28 (m, 1H), 1.33-1.44 (m, 1H), 1.91-1.96 (m, 1H), 2.34 (dd, 1H), 2.54 (dd, 1H), 2.68 (s, 3H), 3.13 (sep, 1H), 4.00 (s, 2H), 7.12 (d, 2H), 7.26 (d, 2H), 7.44 (dt, 2H), 7.56 (dt, 2H) |
| 1-176 | 1.16 (d, 6H), 1.29 (t, 3H), 2.69 (s, 3H), 3.20 (sep, 1H), 4.06 (s, 2H), 4.20 (q, 2H), 7.17 (d, 2H), 7.26 (d, 2H), 7.45 (d, 2H), 7.55 (d, 2H) |
| 1-177 | 1.17-1.19 (m, 12H), 2.38 (s, 3H), 2.59 (m, 1H), 2.68 (s, 3H), 3.11 (m, 1H), 4.13 (s, 2H), 5.71 (s, 2H), 7.10 (d, 2H), 7.22 (d, 2H), 7.44-7.47 (m, 4H). |
| 1-179 | 1.19 (d, 6H), 2.09 (s, 3H), 2.53 (s, 3H), 2.59 (s, 3H), 3.21 (m, 1H), 3.72 (s, 3H), 4.01 (s, 2H), 7.18 (t, 3H), 7.44-7.46 (m, 1H), 7.73 (dd, 1H), 8.67 (d, 1H). |
| 1-181 | 1.03 (d, 3H), 1.16 (d, 3H), 1.73 (d, 3H), 2.67 (s, 3H), 3.09 (sep, 1H), 3.62 (s, 3H), 3.98 (d, 1H), 4.43 (d, 1H), 6.41 (q, 1H), 7.12 (d, 2H), 7.25 (d, 2H), 7.44 (d, 2H), 7.56 (d, 2H) |
| 1-182 | 1.16 (d, 6H), 2.63 (s, 3H), 3.20 (sep, 1H), 3.79 (s, 3H), 4.05 (s, 2H), 7.16 (d, 2H), 7.26 (d, 2H), 7.45 (d, 2H), 7.55 (d, 2H) |
| 1-186 | 1.18 (d, 6H), 2.08 (s, 3H), 2.52 (s, 3H), 3.19 (sep, 1H), 3.72 (s, 3H), 4.02 (s, 2H), 7.04-7.15 (m, 3H), 7.27 (s, 1H), 7.32-7.42 (m, 3H) |
| 1-188 | 1.18 (d, 6H), 2.09 (s, 3H), 2.53 (s, 3H), 3.20 (m, 1H), 3.74 (s, 3H), 4.02 (s, 2H), 6.98 (d, 1H), 7.19 (d, 2H), 7.42 (dd, 2H), 7.93 (m, 1H), 8.38 (d, 1H). |
| 1-190 | 1.19 (d, 6H), 1.37 (d, 6H), 2.08 (s, 3H), 2.52 (s, 3H), 3.22 (m, 1H), 3.72 (s, 3H), 4.00 (s, 2H), 5.32 (m, 1H), 6.72 (d, 1H), 7.13 (d, 2H), 7.40 (d, 2H), 7.72 (dd, 1H), 8.32 (d, 1H). |
| 1-194 | 1.09-1.12 (m, 12H), 2.39 (sep, 1H), 2.68 (s, 3H), 3.09 (sep, 1H), 4.14 (s, 2H), 5.72 (s, 2H), 7.12 (d, 2H), 7.26 (d, 2H), 7.44 (d, 2H), 7.55 (d, 2H) |
| 1-196 | 1.07-1.12 (m, 12H), 2.39 (sep, 1H), 2.62 (s, 3H), 3.10 (sep, 1H), 4.11 (s, 2H), 5.73 (s, 2H), 7.13 (d, 2H), 7.26 (d, 2H), 7.44 (d, 2H), 7.55 (d, 2H) |
| 1-198 | 1.16 (d, 6H), 2.09 (s, 3H), 2.53 (s, 3H), 3.03-3.13 (m, 1H), 3.78 (s, 3H), 4.04 (s, 2H), 6.96-7.82 (m, 3H) |
| 1-201 | 1.10-1.13 (m, 12H), 2.22 (s, 3H), 2.45 (m, 1H), 2.51 (s, 3H), 3.00 (m, 1H), 4.18 (s, 2H), 5.52 (s, 2H), 7.27 (d, 2H), 8.06 (d, 2H). |
| 1-204 | 1.15 (d, 6H), 1.37 (d, 6H), 2.08 (s, 3H), 2.52 (s, 3H), 3.09-3.21 (m, 2H), 3.72 (s, 3H), 3.98 (s, 2H), 7.09 (d, 2H), 7.59 (d, 2H), 7.75 (s, 1H). |
| 1-206 | 1.15 (d, 6H), 1.41 (s, 9H), 2.08 (s, 3H), 2.52 (s, 3H), 3.17 (m, 1H), 3.72 (s, 3H), 3.97 (s, 2H), 7.09 (d, 2H), 7.60 (d, 2H), 7.74 (s, 1H). |
| 1-208 | 1.18 (d, 6H), 2.07 (s, 3H), 2.52 (s, 3H), 3.22 (sep, 1H), 3.68 (s, 3H), 4.04 (s, 2H), 7.11 (td, 1H), 7.27 (s, 1H), 7.31-7.36 (m, 2H), 7.41 (dd, 1H), 7.50 (d, 2H) |
| 1-210 | 1.16 (d, 6H), 2.09 (s, 3H), 2.53 (s, 3H), 3.03-3.13 (m, 1H), 3.78 (s, 3H), 4.04 (s, 2H), 6.96-7.82 (m, 3H) |
| 1-212 | 1.16 (d, 6H), 1.44 (d, 6H), 2.09 (s, 3H), 2.53 (s, 3H), 3.07-3.17 (m, 1H), 3.23-3.33 (m, 1H), 3.76 (s, 3H), 4.01 (s, 2H), 6.88-7.77 (m, 3H) |
| 1-213 | 1.16 (d, 6H), 1.44 (d, 6H), 2.04 (s, 3H), 2.20 (s, 3H), 2.53 (s, 3H), 3.07-3.17 (m, 1H), 3.23-3.33 (m, 1H), 3.96 (s, 2H), 6.88-7.77 (m, 3H) |
| 1-215 | 1.16 (d, 6H), 1.42 (s, 9H), 2.09 (s, 3H), 2.53 (s, 3H), 3.07-3.17 (m, 1H), 3.76 (s, 3H), 4.01 (s, 2H), 6.88-7.78 (m, 3H) |
| 1-216 | 1.16 (d, 6H), 1.42 (s, 9H), 2.09 (s, 3H), 2.22 (s, 3H), 2.53 (s, 3H), 3.07-3.17 (m, 1H), 3.96 (s, 2H), 6.85-7.78 (m, 3H) |
| 1-217 | 1.16 (d, 6H), 2.09 (s, 3H), 2.53 (s, 3H), 2.64 (s, 3H), 3.03-3.13 (m, 1H), 3.78 (s, 3H), 4.04 (s, 2H), 6.89-7.75 (m, 3H) |
| 1-219 | 1.16 (d, 6H), 1.42 (s, 9H), 2.09 (s, 3H), 2.53 (s, 3H), 3.07-3.17 (m, 1H), 3.68 (s, 3H), 4.11 (s, 2H), 7.20-8.04 (m, 4H) |
| 1-220 | 1.16 (d, 6H), 1.50 (s, 9H), 2.10 (s, 3H), 2.53 (s, 3H), 2.91 (s, 3H), 3.07-3.17 (m, 1H), 3.74 (s, 3H), 4.11 (s, 2H), 7.17-8.17 (m, 3H) |
| 1-222 | 0.86 (t, 3H), 1.16 (d, 6H), 1.44 (s, 6H), 1.83 (q, 2H), 2.09 (s, 3H), 2.53 (s, 3H), 3.09-3.19 (m, 1H), 3.73 (s, 3H), 4.04 (s, 2H), 7.17 (d, 2H), 7.95 (d, 2H) |
| 1-224 | 1.16 (d, 6H), 2.09 (s, 3H), 2.53 (s, 3H), 3.09-3.19 (m, 1H), 3.73 (s, 3H), 4.04 (s, 2H), 6.26 (t, 1H), 7.23 (d, 2H), 7.99 (d, 2H) |
| 1-225 | (CD$_3$OD): 1.16 (d, 6H), 1.48 (s, 9H), 2.04 (s, 3H), 2.41 (s, 3H), 3.18-3.28 (m, 1H), 4.10 (s, 2H), 7.06-7.98 (m, 3H) |
| 1-226 | 1.16 (d, 6H), 1.48 (s, 9H), 2.09 (s, 3H), 2.53 (s, 3H), 3.07-3.17 (m, 1H), 3.73 (s, 3H), 4.04 (s, 2H), 6.91-7.96 (m, 3H) |
| 1-238 | 1.06 (t, 3H), 1.16 (d, 6H), 1.86-1.95 (m, 2H), 2.09 (s, 3H), 2.53 (s, 3H), 2.93 (t, 2H), 3.07-3.17 (m, 1H), 3.78 (s, 3H), 4.03 (s, 2H), 6.93-7.95 (m, 3H) |
| 1-239 | (CD$_3$OD) 1.15 (d, 6H), 2.07 (s, 3H), 2.34 (s, 3H), 2.41 (s, 3H), 3.26 (m, 1H), 4.10 (s, 2H), 7.26 (d, 2H), 7.90 (s, 1H), 8.20 (d, 2H), 8.65 (s, 2H) |
| 1-242 | 1.16 (d, 6H), 2.09 (s, 3H), 2.08-2.50 (m, 6H), 2.53 (s, 3H), 3.11-3.19 (m, 1H), 3.72 (s, 3H), 3.73-3.83 (m, 1H), 4.01 (s, 2H), 7.18 (d, 2H), 7.95 (d, 2H) |
| 1-245 | 1.15 (d, 6H), 2.19 (s, 3H), 2.49 (s, 3H), 3.05 (sep, 1H), 3.60 (s, 3H), 4.09 (s, 2H), 7.15 (d, 1H), 7.43 (d, 1H), 7.76 (s, 1H) |
| 1-247 | 1.06 (d, 3H), 1.13 (d, 3H), 1.64 (d, 3H), 2.21 (s, 3H), 2.50 (s, 3H), 2.98 (sep, 1H), 3.63 (s, 3H), 4.04 (d, 1H), 4.38 (d, 1H), 6.04 (q, 1H), 7.26 (d, 2H), 8.05 (d, 2H) |
| 1-248 | 1.14 (d, 6H), 2.64 (s, 3H), 3.13 (sep, 1H), 3.80 (s, 3H), 4.08 (s, 2H), 7.24 (d, 2H), 8.01 (d, 2H) |
| 1-249 | 1.14 (d, 6H), 2.64 (s, 3H), 3.13 (sep, 1H), 3.81 (s, 3H), 4.08 (s, 2H), 7.25 (d, 2H), 8.02 (d, 2H) |
| 1-251 | 1.14 (d, 6H), 2.64 (s, 3H), 3.10 (sep, 1H), 3.82 (s, 3H), 4.11 (s, 2H), 7.30 (d, 2H), 8.08 (d, 2H) |

TABLE 8-continued

| No. | 1H-NMR data (δppm) |
|---|---|
| 1-253 | 1.14 (d, 6H), 2.64 (s, 3H), 3.09 (sep, 1H), 3.82 (s, 3H), 4.11 (s, 2H), 7.30 (d, 2H), 8.09 (d, 2H) |
| 1-254 | (CD$_3$OD): 1.19 (d, 6H), 2.58 (s, 3H), 3.25-3.32 (m, 1H), 4.17 (s, 2H), 7.45 (d, 2H), 8.09 (d, 2H) |
| 1-255 | 1.14 (d, 6H), 2.70 (s, 3H), 3.09 (sep, 1H), 3.82 (s, 3H), 4.12 (s, 2H), 7.30 (d, 2H), 8.09 (d, 2H) |
| 1-264 | 1.16 (d, 6H), 2.09 (s, 3H), 2.53 (s, 3H), 3.13-3.20 (m, 1H), 3.72 (s, 3H), 4.05 (s, 2H), 7.27-9.44 (m, 8H) |
| 1-266 | 1.16 (d, 6H), 1.30-2.15 (m, 10H), 2.09 (s, 3H), 2.53 (s, 3H), 2.91-3.00 (m, 1H), 3.11-3.19 (m, 1H), 3.72 (s, 3H), 4.01 (s, 2H), 7.18 (d, 2H), 7.95 (d, 2H) |
| 1-269 | (CD$_3$OD): 1.17 (d, 6H), 2.07 (s, 3H), 2.41 (s, 3H), 3.21-3.30 (m, 1H), 4.11 (s, 2H), 7.31-8.46 (m, 7H) |
| 1-270 | 1.16 (d, 6H), 2.09 (s, 3H), 2.53 (s, 3H), 3.13-3.20 (m, 1H), 3.72 (s, 3H), 4.04 (s, 2H), 7.21-8.27 (m, 7H) |
| 1-274 | 0.92 (d, 3H), 1.16 (d, 6H), 1.30-3.18 (m, 11H), 2.09 (s, 3H), 2.53 (s, 3H), 3.72 (s, 3H), 4.01 (s, 2H), 7.18 (d, 2H), 7.95 (d, 2H) |
| 1-279 | (CD$_3$OD): 1.19 (d, 6H), 2.58 (s, 3H), 3.25-3.31 (m, 1H), 4.17 (s, 2H), 7.45 (d, 2H), 8.09 (d, 2H) |
| 1-280 | 1.14 (d, 6H), 2.70 (s, 3H), 3.10 (sep, 1H), 3.81 (s, 3H), 4.12 (s, 2H), 7.30 (d, 2H), 8.08 (d, 2H) |
| 1-282 | 1.16 (d, 6H), 1.39 (d, 6H), 2.09 (s, 3H), 2.53 (s, 3H), 3.01-3.21 (m, 2H), 3.74 (s, 3H), 4.04 (s, 2H), 7.23 (d, 2H), 8.00 (d, 2H). |
| 1-284 | 0.95 (t, 3H), 1.14 (d, 6H), 1.39 (m, 2H), 1.91 (m, 2H), 2.07 (s, 3H), 2.51 (s, 3H), 3.14 (m, 1H), 3.70 (s, 3H), 3.99 (s, 2H), 4.29 (t, 2H), 7.13 (d, 2H), 7.95 (d, 2H). |
| 1-288 | 0.87 (t, 3H), 1.14 (d, 6H), 1.30 (m, 2H), 1.86 (m, 2H), 2.04 (s, 3H), 2.20 (s, 3H), 2.52 (s, 3H), 3.09 (m, 1H), 3.99 (s, 2H), 4.21 (m, 2H), 7.21 (d, 2H), 7.52 (d, 2H). |
| 1-290 | 1.06 (t, 3H), 1.16 (d, 6H), 1.86-1.95 (m, 2H), 2.09 (s, 3H), 2.53 (s, 3H), 2.93 (t, 2H), 3.07-3.17 (m, 1H), 3.78 (s, 3H), 4.03 (s, 2H), 7.18 (d, 2H), 7.94 (d, 2H) |
| 1-292 | 0.97 (t, 3H), 1.16 (d, 6H), 1.40-1.48 (m, 2H), 1.80-1.88 (m, 2H), 2.09 (s, 3H), 2.53 (s, 3H), 2.93 (t, 2H), 3.07-3.17 (m, 1H), 3.78 (s, 3H), 4.03 (s, 2H), 7.18 (d, 2H), 7.94 (d, 2H) |
| 1-293 | 1.16 (d, 6H), 2.09 (s, 3H), 2.53 (s, 3H), 3.07-3.17 (m, 1H), 3.19 (s, 6H), 3.70 (s, 3H), 4.00 (s, 2H), 7.14 (d, 2H), 7.86 (d, 2H) |
| 1-300 | 1.03 (d, 6H), 1.16 (d, 6H), 2.09 (s, 3H), 2.22-2.32 (m, 1H), 2.53 (s, 3H), 2.81 (d, 2H), 3.12-3.19 (m, 1H), 3.73 (s, 3H), 4.01 (s, 2H), 7.18 (d, 2H), 7.96 (d, 2H) |
| 1-301 | 1.13-1.17 (m, 12H), 1.48 (s, 9H), 2.20 (s, 3H), 2.38-2.47 (m, 1H), 2.52 (s, 3H), 2.98-3.05 (m, 1H), 4.15 (s, 2H), 5.47 (s, 2H), 7.16 (d, 2H), 7.95 (d, 2H) |
| 1-302 | 1.16 (d, 6H), 1.47 (s, 9H), 1.88 (s, 3H), 2.19 (s, 3H), 2.53 (s, 3H), 2.95-3.05 (m, 1H), 4.13 (s, 2H), 5.45 (s, 2H), 7.16 (d, 2H), 7.96 (d, 2H) |
| 1-305 | (CD$_3$OD): 1.15 (d, 6H), 1.48 (s, 9H), 2.06 (s, 3H), 2.41 (s, 3H), 2.50 (s, 3H), 3.25-3.32 (m, 1H), 4.05 (s, 2H), 7.08-7.80 (m, 3H) |
| 1-307 | (CD$_3$OD): 1.15 (d, 6H), 1.48 (s, 9H), 2.06 (s, 3H), 2.41 (s, 3H), 3.22-3.32 (m, 1H), 4.08 (s, 2H), 7.24-7.76 (m, 3H) |
| 1-310 | 1.13-1.17 (m, 12H), 2.22 (s, 3H), 2.42-2.49 (m, 1H), 2.52 (s, 3H), 2.98-3.05 (m, 1H), 4.15 (s, 2H), 5.53 (s, 2H), 6.95-7.98 (m, 3H) |
| 1-311 | 1.15 (d, 6H), 1.73 (s, 6H), 2.09 (s, 3H), 2.53 (s, 3H), 3.11-3.19 (m, 1H), 3.72 (s, 3H), 4.03 (s, 2H), 7.19 (d, 2H), 7.96 (d, 2H) |
| 1-313 | 1.15 (d, 6H), 1.22-1.31 (m, 4H), 2.09 (s, 3H), 2.20-2.27 (m, 1H), 2.53 (s, 3H), 3.11-3.19 (m, 1H), 3.72 (s, 3H), 4.03 (s, 2H), 7.17 (d, 2H), 7.90 (d, 2H) |
| 1-314 | 1.15 (d, 6H), 2.09 (s, 3H), 2.53 (s, 3H), 3.11-3.19 (m, 1H), 3.72 (s, 3H),, 3.73-3.90 (m, 8H), 4.03 (s, 2H), 7.21 (d, 2H), 7.97 (d, 2H) |
| 1-315 | 1.17 (d, 6H), 2.09 (s, 3H), 2.53 (s, 3H), 3.11-3.19 (m, 1H), 3.20 (s, 3H), 3.30 (s, 3H), 3.72 (s, 3H), 4.03 (s, 2H), 7.22 (d, 2H), 8.00 (d, 2H) |
| 1-316 | 1.10 (d, 6H), 1.42 (s, 9H), 1.90 (s, 3H), 2.20 (s, 3H), 2.51 (s, 3H), 2.98 (sep, 1H), 4.15 (s, 2H), 5.46 (s, 2H), 7.21 (d, 2H), 8.01 (d, 2H) |
| 1-318 | 0.97 (t, 3H), 1.15 (d, 6H), 1.40 (td, 2H), 1.88-1.96 (m, 2H), 2.09 (s, 3H), 2.53 (s, 3H), 3.16 (sep, 1H), 3.72 (s, 3H), 4.01 (s, 2H), 4.28 (t, 2H), 7.15 (d, 2H), 7.97 (d, 2H) |
| 1-321 | 0.88 (t, 3H), 1.14 (d, 6H), 1.29 (td, 2H), 1.83-1.90 (m, 2H), 2.10 (s, 2H), 2.53 (s, 3H), 3.12 (sep, 1H), 3.77 (s, 3H), 4.05 (s, 2H), 4.21 (t, 2H), 7.25 (d, 2H), 7.52 (d, 2H) |
| 1-322 | 0.88 (t, 3H), 1.14 (d, 6H), 1.24-1.34 (m, 2H), 1.83-1.90 (m, 2H), 2.04 (s, 3H), 2.20 (s, 3H), 2.53 (s, 3H), 3.08 (sep, 1H), 4.00 (s, 2H), 4.21 (t, 2H), 7.22 (d, 2H), 7.52 (d, 2H) |
| 1-324 | 0.98 (t, 3H), 1.15 (d, 6H), 1.98 (td, 2H), 2.09 (s, 3H), 2.53 (s, 3H), 3.16 (sep, 1H), 3.72 (s, 3H), 4.01 (s, 2H), 4.25 (t, 2H), 7.15 (d, 2H), 7.97 (d, 2H) |
| 1-327 | 0.89 (t, 3H), 1.15 (d, 6H), 1.92 (td, 2H), 2.10 (s, 3H), 2.53 (s, 3H), 3.12 (sep, 1H), 3.77 (s, 3H), 4.04 (s, 2H), 4.18 (t, 2H), 7.25 (d, 2H), 7.52 (d, 2H) |
| 1-330 | 0.45-0.49 (m, 2H), 0.62-0.67 (m, 2H), 1.15 (d, 6H), 1.34-1.42 (m, 1H). 2.09 (s, 3H), 2.53 (s, 3H), 3.16 (sep, 1H), 3.72 (s, 3H), 4.01 (s, 2H), 4.16 (d, 2H), 7.15 (d, 2H), 7.98 (d, 2H) |
| 1-332 | 0.26-0.30 (m, 2H), 0.55-0.59 (m 2H), 1.14 (d, 6H), 1.21-1.29 (m, 2H), 2.10 (s, 3H), 2.53 (s, 3H), 3.12 (m, 1H), 3.77 (s, 3H), 4.04 (s, 2H), 4.10 (d, 2H), 7.24 (d, 2H), 7.54 (d, 2H) |
| 1-334 | 1.10-1.13 (m, 12H), 1.42 (s, 9H), 2.21 (s, 3H), 2.44 (m, 1H), 2.51 (s, 3H), 3.02 (m, 1H), 4.16 (s, 2H), 5.50 (s, 2H), 7.21 (d, 2H), 8.01 (d, 2H). |
| 1-335 | 1.19 (d, 6H), 2.10 (s, 3H), 2.54 (s, 3H), 3.20 (m, 1H), 3.75 (s, 3H), 4.08 (s, 2H), 6.84 (t, 1H), 7.29 (d, 2H), 7.51 (d, 2H), 7.72 (d, 1H), 8.23 (d, 2H). |

TABLE 8-continued

| No. | 1H-NMR data (δppm) |
|---|---|
| 1-336 | 1.09 (d, 6H), 1.36 (s, 9H), 2.06 (s, 3H), 2.32 (s, 3H), 3.16 (m, 1H), 4.11 (s, 2H), 6.93 (dd, 1H), 7.40 (d, 2H), 7.60 (d, 2H), 7.65 (s, 1H), 8.14 (d, 1H), 9.97 (brs, 1H). |
| 1-341 | 1.17 (d, 6H), 2.08 (s, 3H), 2.52 (s, 3H), 3.19 (m, 1H), 3.76 (s, 3H), 3.98 (s, 2H), 7.00-7.03 (m, 2H), 7.12 (d, 2H), 7.73 (d, 1H), 7.93 (d, 1H). |
| 1-343 | 1.18 (d, 6H), 2.09 (s, 3H), 2.53 (s, 3H), 3.15-3.22 (m, 1H), 3.70 (s, 3H), 3.90 (s, 2H), 5.00 (s, 2H), 6.82 (d, 2H), 7.00 (d, 2H), 7.20 (d, 2H), 7.43 (d, 2H) |
| 1-344 | 1.16 (d, 6H), 2.09 (s, 3H), 2.53 (s, 3H), 3.12-3.75 (m, 1H), 3.73 (s, 3H), 4.03 (s, 2H), 5.97-6.79 (m, 3H), 7.20 (d, 2H), 7.97 (d, 2H) |
| 1-346 | 1.18 (t, 3H), 2.09 (s, 3H), 2.53 (s, 3H), 2.72 (q, 2H), 3.73 (s, 3H), 4.03 (s, 2H), 7.23 (d, 2H), 7.99 (d, 2H) |
| 1-348 | 1.18 (t, 3H), 2.09 (s, 3H), 2.53 (s, 3H), 2.72 (q, 2H), 3.73 (s, 3H), 4.03 (s, 2H), 7.23 (d, 2H), 8.01 (d, 2H) |
| 1-351 | (CD$_3$OD): 1.07 (t, 3H), 1.48 (s, 9H), 2.05 (s, 3H), 2.36 (s, 3H), 2.62 (q, 2H), 4.03 (s, 2H), 7.29 (d, 2H), 7.90 (d, 2H) |
| 1-352 | 1.18 (t, 3H), 1.48 (s, 9H), 2.09 (s, 3H), 2.53 (s, 3H), 2.72 (q, 2H), 3.73 (s, 3H), 4.03 (s, 2H), 7.18 (d, 2H), 7.95 (d, 2H) |
| 1-353 | 1.11 (d, 6H), 1.25 (s, 9H), 2.06 (s, 3H), 2.50 (s, 3H), 3.11 (sep, 1H), 3.69 (s, 3H), 3.82 (s, 2H), 3.89 (s, 2H), 6.87-6.94 (m, 3H), 7.07-7.09 (m, 2H), 7.17 (dd, 1H), 7.22-7.26 (m, 2H) |
| 1-355 | 1.12 (d, 6H), 2.07 (s, 3H), 2.51 (s, 3H), 3.15 (sep, 1H), 3.67 (s, 3H), 3.91 (s, 2H), 3.93 (s, 2H), 6.89 (d, 1H), 6.95-6.99 (m, 2H), 7.12-7.20 (m, 4H), 7.24-7.28 (m, 2H |
| 1-356 | 0.82 (t, 3H), 1.14 (d, 3H), 1.39 (s, 9H), 1.78-1.87 (m, 2H), 2.09 (s, 3H), 2.52 (s, 3H), 3.12 (sep, 1H), 3.77 (s, 3H), 4.00-4.04 (m, 4H), 7.17 (d, 2H), 7.46 (d, 2H) |
| 1-359 | (CD$_3$OD): 2.20 (s, 3H), 2.48 (s, 3H), 2.54 (s, 3H), 4.17 (s, 2H), 7.37 (d, 2H), 8.20 (d, 2H) |
| 1-362 | 0.95 (d, 3H), 1.21 (d, 3H), 2.07 (s, 3H), 2.53 (s, 3H), 3.21-3.29 (m, 1H), 3.35 (s, 3H), 3.83 (s, 3H), 5.68 (s, 1H), 7.12 (d, 2H), 7.30 (d, 2H) |
| 1-363 | 1.08 (d, 3H), 1.21 (d, 3H), 2.07 (s, 3H), 2.53 (s, 3H), 3.22-3.31 (m, 1H), 3.80 (s, 3H), 3.83 (s, 3H), 7.15-7.29 (m, 5H) |
| 1-364 | (CD$_3$OD): 1.14 (d, 6H), 2.06 (s, 3H), 2.40 (s, 3H), 3.25 (sep, 1H), 4.02 (s, 3H), 4.06 (s, 3H), 7.20 (d, 2H), 7.83 (d, 2H) |
| 1-365 | 1.13 (d, 6H), 1.48 (s, 9H), 2.09 (s, 3H), 2.52 (s, 3H), 3.15 (sep, 1H), 3.71 (s, 3H), 3.99 (m, 5H), 7.10 (d, 2H), 7.92 (d, 2H) |
| 1-366 | (CD$_3$OD): 2.23 (s, 3H), 2.50 (s, 3H), 2.54 (s, 3H), 4.17 (s, 2H), 7.37 (d, 2H), 8.20 (d, 2H) |
| 1-368 | (CD$_3$OD): 1.48 (s, 9H), 2.05 (s, 3H), 2.27 (s, 3H), 2.35 (s, 3H), 4.01 (s, 2H), 7.30 (d, 2H), 7.90 (d, 2H) |
| 1-369 | 1.48 (s, 9H), 2.11 (s, 3H), 2.45 (s, 3H), 2.53 (s, 3H), 3.77 (s, 3H), 4.00 (s, 2H), 7.19 (d, 2H), 7.96 (d, 2H) |
| 1-370 | 1.05 (d, 3H), 1.21 (d, 3H), 2.07 (s, 3H), 2.53 (s, 3H), 3.07-3.14 (m, 1H), 3.77 (s, 3H), 6.86 (d, 1H), 7.18-7.29 (m, 4H) |
| 1-374 | 1.18 (d, 6H), 2.09 (s, 3H), 2.53 (s, 3H), 3.15-3.22 (m, 1H), 3.73 (s, 3H), 4.02 (s, 2H), 7.18 (d, 2H), 7.48 (d, 2H), 7.64 (d, 2H), 7.70 (d, 2H) |
| 1-376 | 1.18 (d, 6H), 2.09 (s, 3H), 2.53 (s, 3H), 3.15-3.22 (m, 1H), 3.73 (s, 3H), 4.02 (s, 2H), 7.18 (d, 2H), 7.48 (d, 2H), 7.61 (d, 2H), 7.80 (d, 2H) |
| 1-377 | 1.18 (d, 6H), 2.09 (s, 3H), 2.53 (s, 3H), 3.15-3.22 (m, 1H), 3.73 (s, 3H), 4.02 (s, 2H), 7.17 (d, 2H), 7.48 (d, 2H), 7.58 (d, 2H), 7.68 (d, 2H) |
| 1-378 | 1.18 (d, 6H), 2.09 (s, 3H), 2.53 (s, 3H), 3.15-3.22 (m, 1H), 3.73 (s, 3H), 4.02 (s, 2H), 7.17 (d, 2H), 7.48 (d, 2H), 7.75 (d, 2H), 7.82 (d, 2H) |
| 1-379 | 1.18 (d, 6H), 2.09 (s, 3H), 2.53 (s, 3H), 3.09-3.16 (m, 1H), 3.73 (s, 3H), 3.93 (s, 2H), 7.00 (d, 2H), 7.36 (d, 2H) |
| 1-381 | 1.18 (d, 6H), 2.09 (s, 3H), 2.53 (s, 3H), 2.76 (s, 3H), 3.17-3.24 (m, 1H), 3.73 (s, 3H), 4.02 (s, 2H), 7.18 (d, 2H), 7.48 (d, 2H), 7.69-7.72 (m, 4H) |
| 1-384 | 1.18 (d, 6H), 2.09 (s, 3H), 2.53 (s, 3H), 3.17-3.24 (m, 1H), 3.73 (s, 3H), 4.02 (s, 2H), 7.10-7.38 (m, 6H) |
| 1-388 | 0.95, 1.03 (d, 3H), 1.13-1.16 (m, 6H), 1.40-2.02 (m, 9H), 2.09 (s, 3H), 2.52, 2.53 (s, 3H), 2.83-2.87 (m, 1H), 3.10-3.20 (m, 1H), 3.71, 3.76 (s, 3H), 3.83, 3.88 (s, 3H), 3.99, 4.02 (s, 2H), 7.11, 7.19 (d, 2H), 7.53, 7.94 (d, 2H) |
| 1-390 | 1.17 (d, 6H), 2.07 (s, 3H), 2.11 (s, 3H), 2.52 (s, 3H), 3.20 (m, 1H), 3.70 (s, 3H), 3.96 (s, 2H), 5.02 (s, 1H), 5.32 (s, 1H), 7.03 (d, 2H), 7.35 (m, 2H). |
| 1-391 | (CD$_3$OD): 1.16 (d, 6H), 2.06 (s, 3H), 2.40 (s, 3H), 3.22-3.30 (m, 1H), 4.08 (s, 2H), 7.20-7.52 (m, 7H) |
| 1-392 | 1.18 (d, 6H), 2.09 (s, 3H), 2.53 (s, 3H), 3.17-3.24 (m, 1H), 3.73 (s, 3H), 4.02 (s, 2H), 7.14-7.47 (m, 7H) |
| 1-393 | 1.18 (d, 6H), 2.09 (s, 3H), 2.53 (s, 3H), 3.15-3.22 (m, 1H), 3.73 (s, 3H), 4.02 (s, 2H), 7.21 (d, 2H), 7.52 (d, 2H), 7.82 (d, 2H), 8.06 (d, 2H) |
| 1-394 | 1.18 (d, 6H), 1.68 (s, 3H), 2.09 (s, 3H), 2.53 (s, 3H), 3.18-3.24 (m, 1H), 3.70 (s, 3H), 3.81-4.05 (m, 6H), 7.14 (d, 2H), 7.46 (d, 2H), 7.48-7.52 (m, 4H) |
| 1-395 | 1.08 (s, 9H), 1.16 (d, 6H), 2.07 (s, 3H), 2.19 (s, 2H), 2.51 (s, 3H), 3.17 (m, 1H), 3.73 (s, 3H), 3.92 (s, 2H), 7.02 (d, 2H), 7.03 (s, 1H), 7.37 (d, 2H). |
| 1-396 | 0.92 (s, 9H), 1.12 (d, 6H), 1.99, 2.18 (s, 2H), 2.10 (s, 3H), 2.52 (s, 3H), 3.14 (m, 1H), 3.20 (s, 3H), 3.79 (s, 3H), 3.98 (s, 2H), 7.01 (d, 2H), 7.12 (d, 2H). |
| 1-397 | 1.18 (d, 6H), 2.19 (s, 3H), 2.49 (s, 3H), 3.05-3.14 (m, 2H), 3.60 (s, 3H), 4.10 (s, 2H), 7.17 (d, 2H), 7.48-7.56 (m, 6H) |
| 1-399 | 1.32 (3H, d), 2.09 (3H, s), 2.53 (3H, s), 3.73 (3H, s), 3.90 (2H, s), 4.78-5.01 (2H, m), 6.86-6.95 (4H, m), 7.03-7.08 (2H, m), 7.10-7.15 (2H, m) |

TABLE 8-continued

| No. | 1H-NMR data (δppm) |
|---|---|
| 1-401 | 1.47 (d, 3H), 2.11 (s, 3H), 2.55 (s, 3H), 3.70 (s, 3H), 3.77 (s, 3H), 4.08 (dd, 2H), 5.91 (q, 1H), 6.89-6.95 (m, 4H), 7.09-7.15 (m, 4H) |
| 1-402 | 2.15 (s, 3H), 2.57 (s, 3H), 2.67 (s, 3H), 3.78 (s, 3H), 4.25 (s, 2H), 6.86-6.94 (m, 4H), 7.12-7.26 (m, 4H) |
| 2-1 | (CD$_3$OD): 1.23 (d, 6H), 2.04 (s, 3H), 2.40 (s, 3H), 3.33-3.43 (m, 1H), 4.03 (s, 2H), 7.36 (d, 2H), 8.44 (d, 2H), 8.70 (s, 2H) |
| 2-4 | 1.18 (d, 6H), 2.09 (s, 3H), 2.54 (s, 3H), 3.12 (m, 1H), 3.77 (s, 3H), 4.06 (s, 2H), 7.50 (dd, 1H), 8.03 (d, 1H), 8.69 (d, 1H). |
| 2-6 | 1.17 (d, 6H), 2.08 (s, 3H), 2.53 (s, 3H), 3.08 (m, 1H), 3.78 (s, 3H), 4.08 (s, 2H), 7.56 (d, 1H), 8.15 (d, 1H), 8.72 (s, 1H). |
| 2-7 | (CD$_3$OD): 1.25 (d, 6H), 2.58 (s, 3H), 3.34 (m, 1H), 4.18 (s, 2H), 7.88 (m, 1H), 8.25 (d, 1H), 8.68 (d, 1H). |
| 2-8 | 1.17 (d, 6H), 2.70 (s, 3H), 3.09 (m, 1H), 3.84 (s, 3H), 4.14 (s, 2H), 7.59 (d, 1H), 8.17 (d, 1H), 8.72 (d, 1H). |
| 2-10 | 1.17 (d, 6H), 1.51 (s, 9H), 2.09 (s, 3H). 2.53 (s, 3H), 3.12 (m, 1H), 3.77 (s, 3H), 4.03 (s, 2H), 7.43 (dd, 1H), 7.97 (d, 1H), 8.68 (d, 1H). |
| 2-13 | 1.18 (d, 6H), 2.09 (s, 3H), 2.54 (s, 3H), 3.12 (m, 1H), 3.78 (s, 3H), 4.06 (s, 2H), 7.51 (dd, 1H), 8.04 (d, 1H), 8.71 (d, 1H). |
| 2-15 | 1.13 (d, 6H), 1.98 (s, 3H), 2.21 (s, 3H), 2.51 (s, 3H), 2.99 (sep, 1H), 4.19 (s, 2H), 5.53 (s, 2H), 7.56 (d, 1H), 8.15 (d, 1H), 8.70 (s, 1H) |
| 2-17 | 1.18 (d, 6H), 2.09 (s, 3H), 2.54 (s, 3H), 3.11 (m, 1H), 3.78 (s, 3H), 4.09 (s, 2H), 7.55 (d, 1H), 8.14 (d, 1H), 8.73 (d, 1H). |
| 2-19 | 1.18 (d, 6H), 1.45 (s, 9H), 2.08 (s, 3H), 2.53 (s, 3H), 3.78 (s, 3H), 4.05 (s, 2H), 7.48 (d, 1H), 8.03 (d, 1H), 8.70 (d, 1H). |
| 2-20 | 1.17 (d, 6H), 1.45 (s, 9H), 2.03 (s, 3H), 2.22 (s, 3H), 2.53 (s, 3H), 3.08 (m, 1H), 4.00 (s, 2H), 7.45 (dd, 1H), 8.04 (d, 1H), 8.70 (s, 1H). |
| 2-23 | 1.15 (d, 6H) 2.19 (s, 3H) 2.46 (s, 3H) 3.03 (m, 1H) 3.62 (s, 3H) 4.00 (s, 2H) 7.18 (d, 1H), 7.30-7.32 (m, 1H) 8.23 (d, 1H). |
| 2-25 | 0.91 (d, 3H) 1.16 (d, 6H) 1.22-3.23 (m, 11H) 2.09 (s, 3H) 2.53 (s, 3H) 3.77 (s, 3H), 4.03 (s, 2H), 7.43-8.67 (m, 3H) |
| 2-27 | 1.20 (d, 6H) 1.53 (s, 9H) 2.08 (s, 3H) 2.53 (s, 3H) 3.13 (m, 1H) 3.81 (s, 3H) 4.01 (s, 2H), 8.71 (s, 2H). |
| 2-37 | 1.18 (d, 6H) 2.09 (s, 3H) 2.54 (s, 3H) 3.12 (m, 1H) 3.78 (s, 3H) 4.06 (s, 2H) 7.51 (dd, 1H), 8.04 (d, 1H), 8.71 (d, 1H). |
| 3-1 | (CD$_3$OD): 2.24 (m, 3H), 2.52 (m, 3H), 6.50 (m, 1H), 6.64 (m, 2H), 7.05 (m, 2H), 7.24 (m, 3H). |
| 4-2 | 2.00 (s, 3H), 2.23 (s, 3H), 2.31 (s, 3H), 2.87-3.00, 3.45-3.52 (m, 2H), 3.67 (m, 2H), 5.51 (m, 1H), 7.39 (m, 2H), 7.57 (m, 2H), 10.15 (brs, 1H). |
| 4-3 | 2.02 (s, 3H), 2.37 (s, 3H), 2.48 (s, 3H), 2.52 (s, 3H), 2.65 (dd, 1H), 3.18 (dd, 1H), 3.66 (m, 2H), 5.26 (t, 1H), 7.39 (d, 2H), 7.59 (d, 2H). |
| 4-5 | 2.00 (s, 3H), 2.10 (2, 3H), 2.25 (s, 3H), 2.60-2.70, 3.00-3.10 (m, 2H), 2.71-2.89 (m, 2H), 3.49 (dd, 2H), 4.78 (m, 1H), 7.28 (d, 2H), 7.45 (d, 2H), 7.95 (brs, 1H). |
| 4-8 | 2.00 (s, 3H), 2.26 (s, 3H), 2.30 (s, 3H), 3.35 (s, 2H), 3.63 (dd, 2H), 7.47 (t, 1H), 7.63 (m, 2H), 7.75 (s, 1H), 8.52 (brs, 1H). |
| 4-9 | 2.01 (s, 3H), 2.31 (s, 3H), 2.48 (s, 3H), 2.50 (s, 3H), 3.08 (d, 1H), 3.46 (d, 1H), 3.63 (s, 2H), 7.52 (t, 1H), 7.65 (t, 2H), 7.75 (s, 1H). |
| 4-11 | 1.61 (s, 3H), 1.99 (s, 3H), 2.22 (s, 3H), 2.25 (s, 3H), 3.12 (q, 2H), 3.60 (q, 2H), 7.49 (d, 2H), 7.55 (d, 2H), 9.93 (brs, 1H). |
| 4-14 | 2.00 (s, 3H), 2.00-2.20 (m, 2H), 2.23 (s, 3H), 2.30 (s, 3H), 2.80 (dd, 1H), 3.17 (dd, 1H), 3.61 (m, 2H), 4.52 (t, 2H), 4.72 (m, 1H), 7.82 (d, 1H), 8.30 (s, 1H), 8.74 (brs, 1H). |
| 4-15 | 2.01 (s, 3H), 2.04-2.20 (m, 2H), 2.35 (s, 3H), 2.48 (s, 3H), 2.54 (s, 3H), 2.41-2.60, 2.86-2.93 (m, 2H), 3.60 (m, 2H), 4.40-4.56 (m, 2H), 4.73 (m, 1H), 7.81 (s, 1H), 8.28 (s, 1H). |
| 4-17 | 2.00 (s, 3H), 2.25 (s, 3H), 2.31 (s, 3H), 3.01 (dd, 1H), 3.17 (dd, 1H), 3.62 (q, 2H), 4.44 (ddd, 2H), 4.90 (m, 1H), 7.82 (d, 1H), 8.28 (d, 1H), 8.75 (brs, 1H). |
| 4-19 | 0.86 (t, 3H), 1.23-1.33 (m, 10H), 1.33-1.66 (m, 2H), 2.21 (s, 3H), 2.37 (dd, 1H), 2.47 (m, 6H), 2.79 (dd, 1H), 3.61 (m, 2H), 4.44 (m, 1H), 4.82 (m, 2H), 7.32-7.46 (m, 5H). |
| 4-20 | 0.83 (t, 3H), 1.14-1.68 (m, 14H), 2.00 (s, 3H), 2.22 (s, 3H), 2.28 (s, 3H), 2.59 (dd, 1H), 3.00 (dd, 1H), 3.58 (d, 2H), 4.43 (m, 1H), 8.50 (brs, 1H). |
| 5-1 | (DMSO-d$_6$): 1.78 (s, 3H), 2.16 (s, 3H), 2.23 (s, 3H), 3.90 (s, 2H), 7.47-7.63 (m, 2H), 8.14 (d, 2H). |
| 5-5 | 2.01 (s, 3H), 2.32 (s, 3H), 2.49 (s, 3H), 2.60 (s, 3H), 3.12-3.15 (m, 4H), 3.88-3.92 (m, 2H), 7.28 (d, 2H), 7.51 (d, 2H). |
| 6-1 | 1.66-2.74 (20H, m), 3.47 (2H, s), 4.28-4.35 (1H, m), 7.02-7.35 (4H, m) |
| 6-2 | 1.85-2.80 (17H, m), 3.74 (2H, s), 4.41-4.47 (1H, m), 7.05-7.40 (4H, m) |
| 6-3 | 1.65-2.75 (17H, m), 3.48 (2H, s), 4.28-4.37 (3H, m), 5.28-5.47 (2H, m), 7.02-7.35 (4H, m) |
| 6-4 | 1.74-2.73 (20H, m), 3.47 (2H, s), 4.18-4.27 (1H, m), 6.84-7.11 (4H, m) |
| 6-5 | 1.74-2.73 (17H, m), 3.47 (2H, s), 3.72 (1H, m), 6.88-7.14 (4H, m) |
| 6-6 | 1.72-2.65 (19H, m), 3.13 (2H, d), 3.75 (2H, s), 7.13-7.7.25 (4H, m) |
| 7-1 | 2.02 (3H, s), 2.34 (3H, s), 2.52 (3H, s), 2.61 (3H, s), 3.17 (1H, d), 3.48 (1H, d), 4.61 (1H, d), 4.93 (1H, d), 7.43-7.66 (4H, m) |
| 7-2 | 1.98 (3H, s), 2.25 (3H, s), 2.27 (3H, s), 3.16 (1H, d), 3.49 (1H, d), 4.76 (1H, d), 4.93 (1H, d), 7.47-7.66 (4H, m) |
| 7-3 | 2.19 (3H, s), 2.44 (3H, s), 2.49 (3H, s), 3.22 (1H, d), 3.54 (1H, d), 4.29-4.41 (2H, m), 4.80 (1H, d), 4.97 (1H, d), 5.26-5.43 (2H, m), 7.41-7.66 (4H, m) |

TABLE 8-continued

| No. | 1H-NMR data (δppm) |
|---|---|
| 7-5 | (DMSO-d$_6$): 1.78-1.85 (m, 3H), 2.13-2.25 (m, 3H), 3.19 (s, 3H), 3.81 (s, 2H), 6.86 (s, 1H), 7.84 (d, 2H), 8.03 (d, 2H), 10.9 (brs, 1H). |
| 7-8 | (CD$_3$OD): 1.26 (d, 6H), 2.06 (s, 3H), 2.40 (s, 3H), 3.30-3.40 (m, 1H), 4.18 (s, 2H), 6.80-7.62 (m, 6H) |
| 7-10 | 1.14 (d, 6H), 1.96 (m, 1H), 2.53 (m, 1H), 2.67 (s, 3H), 2.81-3.00 (m, 2H), 3.23 (m, 1H), 3.78 (s, 3H), 3.99 (s, 2H), 4.28 (t, 1H), 6.81 (d, 1H), 6.86 (d, 1H), 6.96 (m, 3H), 7.08 (m, 2H). |
| 7-12 | 1.17 (d, 6H), 2.09 (s, 3H), 2.54 (s, 3H), 3.25 (sep, 1H), 3.56 (s, 3H), 4.13 (s, 2H), 7.24-7.26 (m, 1H), 7.38-7.44 (m, 2H), 7.46 (s, 2H), 7.78-7.70 (m, 3H) |
| 7-18 | 1.18 (d, 6H), 2.00-2.09 (m, 1H), 2.09 (s, 3H), 2.53 (s, 3H), 2.61 (m, 1H), 2.91 (m, 1H), 3.06 (m, 1H), 3.12 (m, 1H), 3.67 (s, 3H), 3.93 (d, 2H), 4.33 (t, 1H), 6.62 (d, 1H), 6.76 (d, 1H), 6.97 (m, 3H), 7.14 (m, 2H). |
| 7-20 | 1.16 (d, 6H), 2.08 (s, 3H), 2.53 (s, 3H), 3.18 (sep, 1H), 3.72 (s, 3H), 4.14 (s, 2H), 7.33 (dd, 1H), 7.86 (d, 1H), 7.89 (s, 1H) |
| 7-23 | 1.18 (d, 6H), 2.09 (s, 3H), 2.53 (s, 3H), 3.12-3.22 (m, 1H), 3.70-4.01 (m, 8H), 6.26, 6.48 (d, 1H), 7.10-7.67 (m, 5H) |
| 7-29 | 1.09 (dd, 6H), 1.96 (m, 1H), 2.05 (s, 3H), 2.49 (s, 3H), 2.53 (m, 1H), 2.87 (m, 1H), 2.94 (m, 1H), 3.12 (m, 1H), 3.71 (s, 3H), 3.86 (dd, 2H), 4.26 (t, 1H), 6.69 (s, 1H), 6.85 (m, 1H), 6.97 (t, 1H), 7.07-7.14 (m, 3H). |
| 7-30 | (CD$_3$OD): 1.14 (d, 6H), 2.07 (s, 3H), 2.42 (s, 3H), 3.33-3.38 (m, 1H), 4.36 (s, 2H), 7.06 (d, 1H), 7.19 (t, 1H), 7.35 (t, 1H), 7.48 (t, 1H), 7.62 (d, 1H), 7.81 (d, 1H), 8.00 (d, 1H) |
| 7-32 | (CD$_3$OD): 1.15 (d, 6H), 2.09 (s, 3H), 2.42 (s, 3H), 3.33-3.40 (m, 1H), 4.21 (s, 2H), 7.30 (dd, 1H), 7.42 (ddd, 2H), 7.73 (d, 1H), 7.83 (dt, 1H), 8.02 (d, 1H), 8.12-8.16 (m, 1H) |
| 7-35 | 1.16 (dd, 6H), 1.74 (m, 1H), 2.08 (s, 3H), 2.48 (t, 2H), 2.52 (s, 3H), 2.56 (m, 1H), 2.80 (m, 1H), 2.87 (m, 1H), 3.18 (m, 1H), 3.33 (s, 3H), 3.65 (t, 2H), 3.74 (s, 3H), 3.94 (s, 2H), 5.42 (q, 1H), 6.31 (d, 1H), 6.93 (s, 1H), 6.94 (d, 1H), 7.14 (d, 1H). |
| 7-36 | 1.17-1.19 (m, 6H), 2.05, 2.09 (s, 3H), 2.31, 2.40 (s, 3H), 2.53 (s, 3H), 3.17 (m, 1H), 3.71, 3.74 (s, 3H), 4.00 (s, 2H), 7.12-7.27 (m, 6H), 7.65 (d, 2H). |
| 7-37 | 1.16 (d, 6H), 2.07 (s, 3H), 2.22 (s, 3H), 2.52 (s, 3H), 3.15 (m, 1H), 3.72 (s, 3H), 3.98 (s, 2H), 4.67 (t, 2H), 6.05 (m, 1H), 7.09 (d, 2H), 7.52 (d, 2H). |
| 7-38 | 1.16 (d, 6H), 1.21-2.30 (m, 8H), 2.08 (s, 3H), 2.17, 2.22 (s, 3H), 2.52 (s, 3H), 3.16 (m, 1H), 3.73 (s, 3H), 3.97 (s, 2H), 3.88-4.16 (m, 1H), 4.29, 4.44 (m, 1H), 7.07 (d, 2H), 7.51-7.55 (m, 2H). |
| 7-39 | 1.16 (d, 6H), 2.07 (s, 3H), 2.08 (s, 3H), 2.52 (s, 3H), 3.17 (m, 1H), 3.71 (s, 3H), 3.88 (m, 2H), 3.96 (s, 2H), 5.19 (m, 1H), 7.05 (d, 2H), 7.53 (d, 2H). |
| 7-40 | 1.36 (d, 6H), 2.15 (s, 3H), 2.52 (s, 3H), 3.28 (bs, 1H), 3.75 (s, 3H), 4.03 (s, 2H), 7.18 (d, 2H), 7.50 (d, 2H), 7.58 (d, 2H), 7.68 (d, 2H) |
| 7-41 | 1.18 (d, 6H), 1.89 (t, 2H), 2.09 (s, 3H), 2.43-2.62 (m, 4H), 2.47 (s, 3H), 3.08-3.15 (m, 1H), 3.69 (s, 3H), 3.95-4.03 (m, 6H), 5.92-5.95 (m, 1H), 7.00 (d, 2H), 7.27 (d, 2H) 1.18 (d, 6H), 2.09 (s, 3H), 2.47 (s, 3H), 2.61-3.05 (m, 6H), 3.10-3.22 (m, 1H), 3.71 (s, 3H), 3.98 (s, 2H), 6.02-6.06 (m, 1H), 7.06 (d, 2H), 7.27 (d, 2H) |
| 7-44 | 0.89, 0.92 (d, 3H), 1.16 (d, 6H), 1.31 (t, 3H), 1.35-1.93 (m, 9H), 2.07 (s, 3H), 2.15-2.48 (m, 1H), 2.51 (s, 3H), 3.16 (sep, 1H), 3.73 (s, 3H), 3.96 (s, 2H), 4.19 (q, 2H), 7.04-7.07 (m, 2H), 7.32-7.34 (m, 2H), 7.90, 8.00 (s, 1H) |
| 7-48 | 1.15-1.85 (m, 7H), 1.22-1.25 (m, 6H), 2.05, 2.06 (s, 3H), 2.05-2.21 (m, 2H), 2.47-2.49 (m, 5H), 2.84-3.22 (m, 1H), 3.17 (sep, 1H), 3.91, 3.93 (s, 3H) ESI-MS [M + H]+: 456.9 |
| 7-49 | 0.99-1.09, 1.44-1.77, 1.97-2.11, 2.35-2.48, 2.91 (m, 12H), 1.22-1.24 (m, 6H), 2.06 (s, 3H), 2.48 (s, 3H), 3.09-3.20 (m, 1H), 3.92, 3.93 (s, 3H) ESI-MS [M + H]+: 345.7 |
| 7-50 | 1.18 (d, 6H), 1.82-1.98 (m, 2H), 2.07 (s, 3H), 2.14-2.20 (m, 2H), 2.46-2.57 (m, 7H), 2.93-3.22 (m, 2H), 3.73 (s, 3H), 3.94 (s, 2H), 7.03 (d, 2H), 7.12 (d, 2H) |

\* Unless otherwise specified in the table, NMR measurement solvent is CDCl$_3$.

As described above, the compound of the present invention can be easily produced by using known chemical reactions as in the above examples.

[Biological Test]

The following test examples show that the compound of the present invention is useful as an active ingredient of agricultural and horticultural fungicides, insecticidal or acaricidal agents.

(Test Example 1) Test for Controlling Wheat Powdery Mildew 5 parts of the compound of the present invention, 1.5 parts of polyoxyethylene sorbitan monolaurate, and 93.5 parts of dimethylformamide were mixed to prepare an emulsion having an active ingredient of 5%. The emulsion was diluted with water so that the compound of the present invention is to be 125 ppm to obtain a chemical solution.

Subsequently, the chemical solution was sprayed on wheat seedlings cultivated in a seedling-raising pot (variety "Chihoku", 1-2 leaf stage). After air-drying, conidia of wheat powdery mildew fungus (*Erysiphe graminis* f.sp. *tritici*) were shaken off and inoculated, and kept in a temperature-controlled room at 20° C. On the 6th day after inoculation, the appearance of disease spots on the leaves was examined (treatment group).

Meanwhile, the wheat was grown without spraying the diluted solution, and the appearance of disease spots was likewise investigated (untreated group).

The controlling value based on the untreated group was calculated by the following formula.

Controlling value (%)=100−{area where disease spots appeared (treated group)/area where disease spots appeared (untreated group)}×100

The compounds shown in Table 9 was subjected to the test for controlling wheat powdery mildew. The controlling value of the all compounds was 75% or more.

TABLE 9

1-3
1-6
1-8
1-9
1-24
1-25
1-26
1-27
1-28
1-29
1-30
1-31
1-32
1-33
1-35
1-37
1-39
1-40
1-41
1-42
1-43
1-44
1-45
1-46
1-47
1-48
1-49
1-50
1-51
1-52
1-60
1-61
1-62
1-63
1-64
1-65
1-66
1-67
1-68
1-69
1-70
1-71
1-72
1-73
1-75
1-78
1-79
1-80
1-81
1-89
1-90
1-92
1-93
1-94
1-99
1-100
1-101
1-102
1-103
1-104
1-105
1-107
1-109
1-110
1-111
1-113
1-114
1-115
1-116
1-117
1-119
1-120
1-121
1-122
1-123

TABLE 9-continued 1-124
1-125
1-126
1-127
1-128
1-129
1-130
1-134
1-135
1-136
1-137
1-138
1-139
1-141
1-144
1-145
1-146
1-147
1-148
1-149
1-150
1-151
1-152
1-153
1-157
1-158
1-159
1-160
1-161
1-162
1-163
1-164
1-165
1-166
1-167
1-168
1-169
1-170
1-171
1-172
1-173
1-177
1-178
1-179
1-180
1-182
1-183
1-184
1-185
1-186
1-188
1-190
1-191
1-192
1-193
1-194
1-196
1-197
1-198
1-199
1-200
1-201
1-202
1-203
1-204
1-206
1-207
1-208
1-209
1-210
1-211
1-212
1-213
1-215
1-216
1-217
1-222
1-223
1-224
1-225

TABLE 9-continued

| | |
|---|---|
| 1-226 | 1-348 |
| 1-227 | 1-350 |
| 1-228 | 1-351 |
| 1-229 | 1-352 |
| 1-231 | 1-355 |
| 1-233 | 1-358 |
| 1-234 | 1-360 |
| 1-235 | 1-361 |
| 1-236 | 1-399 |
| 1-237 | 1-400 |
| 1-238 | 1-401 |
| 1-240 | 2-1 |
| 1-242 | 2-2 |
| 1-244 | 2-4 |
| 1-247 | 2-5 |
| 1-248 | 2-6 |
| 1-249 | 2-7 |
| 1-250 | 2-8 |
| 1-251 | 2-9 |
| 1-252 | 2-11 |
| 1-253 | 2-12 |
| 1-254 | 2-13 |
| 1-255 | 2-14 |
| 1-257 | 2-15 |
| 1-259 | 2-16 |
| 1-260 | 2-17 |
| 1-261 | 2-18 |
| 1-262 | 2-19 |
| 1-264 | 2-20 |
| 1-266 | 2-23 |
| 1-268 | 2-29 |
| 1-270 | 2-32 |
| 1-272 | 3-7 |
| 1-279 | 3-8 |
| 1-280 | 3-10 |
| 1-281 | 7-9 |
| 1-282 | 7-10 |
| 1-283 | 7-11 |
| 1-284 | 7-12 |
| 1-285 | 7-14 |
| 1-286 | 7-15 |
| 1-287 | 7-16 |
| 1-288 | 7-18 |
| 1-290 | 7-20 |
| 1-294 | 7-21 |
| 1-295 | 7-22 |
| 1-296 | 7-23 |
| 1-297 | 7-24 |
| 1-298 | 7-25 |
| 1-301 | 7-27 |
| 1-302 | 7-28 |
| 1-304 | 7-29 |
| 1-305 | 7-32 |
| 1-306 | 7-33 |
| 1-308 | 7-37 |
| 1-309 | 7-38 |
| 1-310 | |
| 1-313 | |
| 1-316 | |
| 1-317 | |
| 1-318 | |
| 1-319 | |
| 1-320 | |
| 1-321 | |
| 1-322 | |
| 1-324 | |
| 1-325 | |
| 1-327 | |
| 1-329 | |
| 1-330 | |
| 1-333 | |
| 1-334 | |
| 1-339 | |
| 1-340 | |
| 1-341 | |
| 1-342 | |
| 1-343 | |
| 1-345 | |
| 1-346 | |
| 1-347 | |

(Test Example 2) Test for Controlling Wheat Red Rust Disease

An emulsion was prepared in the same manner as in Test Example 1. The emulsion was diluted with water so that the compound of the present invention is to be 125 ppm to obtain a chemical solution.

Subsequently, the chemical solution was sprayed on the wheat seedlings cultivated in a seedling-raising pot (variety: "Norin No. 61", 1-2 leaf stage). After air-drying, summer spores of wheat *Pseudomonas aeruginosa* (*Puccinia recondita*) were shaken off and inoculated, and kept in a temperature-controlled room at 20° C. On the 12th day after inoculation, the appearance of disease spots on the leaves was examined (treatment group).

Meanwhile, the wheat was grown without spraying the diluted solution, and the appearance of disease spots was likewise investigated (untreated group).

The controlling value was calculated in the same manner as in Test Example 1.

The compounds shown in TABLE 10 were subjected to the test for controlling wheat red rust disease. The controlling value of the all compounds was 75% or more.

TABLE 10

1-3
1-24
1-25
1-26
1-27
1-41
1-42
1-43
1-44
1-45
1-47
1-60
1-61
1-64
1-65
1-70
1-71
1-90
1-93
1-105
1-116
1-117
1-130
1-135
1-137
1-139
1-144
1-147
1-150
1-157
1-158
1-159
1-165
1-166
1-201
1-203
1-204
1-206
1-209
1-210
1-212
1-214
1-215
1-216
1-221
1-224
1-225
1-226
1-227
1-233
1-235
1-236
1-241
1-242
1-244
1-247
1-248
1-249
1-255
1-256
1-257
1-261
1-262
1-263
1-264
1-266
1-268
1-269
1-271
1-273
1-274
1-281
1-282

TABLE 10-continued 1-289
1-290
1-291
1-293
1-294
1-295
1-296
1-299
1-300
1-301
1-302
1-306
1-310
1-312
1-313
1-333
1-334
1-342
1-346
1-347
1-348
1-351
1-352
1-360
1-361
1-400
2-1
2-5
2-6
2-12
2-13
2-15
2-16
2-24
2-32
7-37
7-38

(Test Example 3) Efficacy Confirmation Test on *Pseudaletia Separata*

In the same manner as in Test Example 1, an emulsion with an active ingredient of 5% was prepared.

0.8 g of commercially available artificial feed (Insecta LFS, manufactured by Nosan Corporation) and 1 μl of the emulsion were mixed thoroughly, and 0.2 g per each treatment group was packed in a plastic test container (1.4 ml) to prepare test feed. Two second instar larvae were inoculated into each treatment group and sealed with a plastic lid. It was placed in a thermostatic chamber at 25° C., and the mortality rate and feed intake were examined on the 5th day. The test was performed in duplicate. Further, a test conducted under the same conditions except that the compound of the present invention was removed from the emulsion was used as a solvent control group. The mortality rate was calculated by the following formula.

Mortality rate (%)=(number of dead insects/number of test insects)×100

The compounds shown in TABLE 11 were subjected to the efficacy confirmation test on *pseudaletia separata*. In all of the compounds, the mortality rate on *pseudaletia separata* was 100%, and the feed intake in ratio of the solvent control group was 10% or less.

TABLE 11

1-20
1-21
1-74
1-89

TABLE 11-continued 1-90
1-150
1-158
1-159
1-348

(Test Example 4) Efficacy Confirmation Test on Bean Aphid

An emulsion was prepared in the same manner as in Test Example 1. The emulsion was diluted with water so that the compound of the present invention is to be 125 ppm to obtain a chemical solution.

Cowpea plants were raised in No. 3 pots and inoculated with bean aphid nymphs on primary leaves. The chemical solution was sprayed on the cowpea seedlings. The cowpea seedlings were placed in a thermostatic chamber at a temperature of 25° C. and a humidity of 60%. On the 4th day after spraying, the life and death of the aphid were determined and the mortality rate was calculated. The test was performed in duplicate.

The mortality rate was calculated in the same manner as in Test Example 3.

The compounds shown in TABLE 12 were subjected to the efficacy confirmation test on bean aphid. All of the compounds showed a mortality rate of 100% on bean aphid.

TABLE 12

1-3
1-5
1-9
1-18
1-21
1-23
1-27
1-29
1-31
1-33
1-35
1-37
1-39
1-40
1-44
1-46
1-49
1-50
1-51
1-61
1-67
1-68
1-70
1-72
1-79
1-90
1-103
1-121
1-135
1-137
1-150
1-165
1-166
1-168
1-171
1-172
1-173
1-176
1-194
1-198
1-199
1-208
1-210
1-211
1-224
1-227
1-229
1-233
1-247
1-248
1-249
1-253
1-255
1-257
1-260
1-301
1-302
1-304
1-316
1-346
1-348
1-350
1-360
1-399
1-401
1-402
2-15
3-2
3-4
3-5
3-7
3-8
4-3
4-9
4-12
4-21
7-9

(Test Example 5) Efficacy Confirmation Test on *Tetranychus kanzawai*

An emulsion was prepared in the same manner as in Test Example 1. The emulsion was diluted with water so that the compound of the present invention is to be 125 ppm to obtain a chemical solution.

Kidney bean plants were raised in 3 pots, and inoculated with 10 female imagoes of *tetranychus kanzawai* on primary leaves. The medicinal solution was sprayed on the kidney bean seedlings. The kidney bean seedlings were placed in a thermostatic chamber at a temperature of 25° C. and a humidity of 65%. On the 10th day after spraying, the survival and death of imagoes of *tetranychus kanzawai* were determined and the mortality rate was calculated. The test was performed in duplicate.

The mortality rate was calculated in the same manner as in Test Example 3.

The compounds shown in TABLE 13 were subjected to the efficacy confirmation test on *tetranychus kanzawai*. All of the compounds showed a mortality rate of 100% on *tetranychus kanzawai*.

TABLE 13

1-3
1-5
1-9
1-21
1-23
1-25
1-27
1-28
1-44
1-51
1-54
1-56

TABLE 13-continued 1-65
1-66
1-67
1-68
1-90
1-98
1-100
1-106
1-111
1-117
1-119
1-139
1-149
1-150
1-157
1-159
1-166
1-210
1-215
1-224
1-231
1-247
1-302
1-304
1-348
1-399
2-15
3-7
7-12
7-16
7-20
7-25

Since any one of the compounds randomly selected from the compounds of the present invention exhibits the above-mentioned effects, it can be understood that the compounds of the present invention including the compounds which have not been exemplified above have effect such as a harmful organism control effect, fungicidal effect, acaricidal effect, insecticidal effect or the like, and do not cause phytotoxicity to plants, and have little toxicity to livestocks and fish and environmental impact.

INDUSTRIAL APPLICABILITY

The pyridine compound according to the present invention is a novel compound having effects such as a harmful organism control effect, fungicidal effect, acaricidal effect, insecticidal effect or the like without causing phytotoxicity to the plant and with less toxicity to livestocks and fish and less environmental impact. In particular, it shows an excellent controlling effect against wheat disease. The pyridine compound according to the present invention is useful as an active ingredient of agricultural and horticultural fungicides, harmful organism control agents, insecticidal or acaricidal agents, and is industrially applicable.

The invention claimed is:
1. A pyridine compound represented by formula (I), an N-oxide compound thereof, or a tautomer or salt thereof,

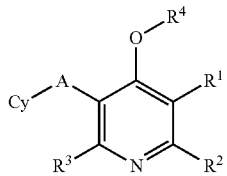
(I)

in formula (I), $R^1$ represents a hydrogen atom, an unsubstituted or $G^1$-substituted C1-6 alkyl group, an unsubstituted or $G^1$-substituted C2-6 alkenyl group, an unsubstituted or $G^1$-substituted C1-6 alkoxycarbonyl group, an unsubstituted or $G^1$-substituted C1-6 alkylthio group, an unsubstituted or $G^1$-substituted C1-6 alkylaminocarbonyl group, an unsubstituted or $G^2$-substituted C6-10 aryl group, a cyano group or a halogeno group, in formula (I), $R^2$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, a formyloxy group, an unsubstituted or $G^1$-substituted C1-6 alkylcarbonyloxy group, an unsubstituted or $G^2$-substituted C6-10 aryl group, an (unsubstituted or $G^1$-substituted C1-6 alkoxyimino)-C1-6 alkyl group, an unsubstituted or $G^2$-substituted 3- to 10-membered heterocyclyl C1-6 alkyl group, a cyano group or a halogeno group, in formula (I), $R^3$ represents a hydrogen atom, an unsubstituted or $G^1$-substituted C1-6 alkyl group, an unsubstituted or $G^1$-substituted C2-6 alkenyl group, an unsubstituted or $G^2$-substituted C3-8 cycloalkyl group, an unsubstituted or $G^1$-substituted C1-6 alkoxy group, an unsubstituted or $G^1$-substituted C1-6 alkylcarbonyl group, an unsubstituted or $G^1$-substituted C1-6 alkoxycarbonyl group, a carboxyl group, a formyl group, a formyloxy group, an unsubstituted or $G^1$-substituted C1-6 alkylcarbonyloxy group, an unsubstituted or $G^2$-substituted C6-10 aryl group, an unsubstituted or $G^2$-substituted 3- to 10-membered heterocyclyl group, an (unsubstituted or $G^1$-substituted C1-6 alkoxyimino)-C1-6 alkyl group, an unsubstituted or $G^1$-substituted mono C1-6 alkylamino group, an unsubstituted or $G^1$-substituted di C1-6 alkylamino group, a cyano group or a halogeno group, in formula (I), $R^4$ represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl C1-6 alkyl group, an unsubstituted or $G^2$-substituted 3- to 10-membered heterocyclyl C1-6 alkyl group, a formyl group, an unsubstituted or $G^1$-substituted C1-6 alkylcarbonyl group, an unsubstituted or $G^2$-substituted C3-8 cycloalkylcarbonyl group, an unsubstituted or $G^1$-substituted C2-6 alkenylcarbonyl group, an unsubstituted or $G^2$-substituted C6-10 arylcarbonyl group, an unsubstituted or $G^1$-substituted C1-6 alkoxycarbonyl group, an unsubstituted or $G^1$-substituted C2-6 alkenyloxycarbonyl group, an unsubstituted or $G^1$-substituted C1-6 alkylsulfonyl group, an unsubstituted or $G^1$-substituted C1-6 alkylaminocarbonyl group, an unsubstituted or $G^1$-substituted (C1-6 alkylthio) carbonyl group, an unsubstituted or $G^1$-substituted C1-6 alkylamino (thiocarbonyl) group or an organic group represented by formula (II),

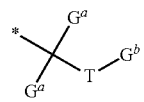
(II)

in formula (II), * represents bonding site, in formula (II), each $G^a$ independently represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, or an unsubstituted or $G^2$-substituted C6-10 aryl group, in formula (II), $G^b$ represents a hydrogen atom, an unsubstituted or $G^1$-substituted C1-6 alkyl group, an unsubstituted or $G^1$-substituted C2-6 alkenyl group, an unsubstituted or $G^1$-substituted C2-6 alkynyl group, an unsubstituted or $G^2$-substituted C3-8 cycloalkyl group, an unsubstituted or $G^2$-substituted C6-10 aryl group, or an unsubstituted or $G^2$-substituted 3- to 10-membered heterocyclyl group, in formula (II), T represents an oxygen atom, an oxycarbonyl group, a carbonyloxy group, an oxycarbonyloxy group, a sulfur atom, a (thio) carbonyl group, a carbonyl (thio) group, a (thio) carbonyloxy group, an oxycarbonyl (thio) group or a divalent group represented by —O—C(=O)—N($G^b$)-, in formula (I), A represents an oxygen atom or a divalent organic group represented by formula (III),

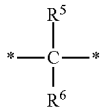

(III)

in formula (III), * represents bonding site, in formula (III), $R^5$ and $R^6$ each independently represent a hydrogen atom, an unsubstituted or $G^1$-substituted C1-6 alkyl group, an unsubstituted or $G^1$-substituted C1-6 alkoxy group, an unsubstituted or $G^2$-substituted C6-10 aryloxy group, an unsubstituted or $G^1$-substituted alkoxycarbonyloxy group, a halogeno group, a hydroxyl group, $R^5$ and $R^6$ may bond to form a 3- to 6-membered ring together with the carbon atom to which $R^5$ and $R^6$ are bonded, in formula (I), Cy represents an unsubstituted or $G^2$-substituted C6-10 aryl group, a $G^2$-substituted C3-8 cycloalkyl group, an unsubstituted or $G^2$-substituted 3- to 10-membered heterocyclyl group or a 13-membered heteroaryl group, $G^1$ represents a hydroxyl group, a C1-6 alkoxy group, a C1-6 alkoxy C1-6 alkoxy group, a C1-6 alkoxycarbonyl group, a formyloxy group, a C1-6 alkylcarbonyloxy group, a C1-6 alkoxycarbonyloxy group, a mono C1-6 alkoxycarbonylamino group, a cyano group, an amino group or a halogeno group, when there are two or more $G^1$-substituted groups, such G's may be the same as or different from each other, $G^2$ represents an unsubstituted or $G^{21}$-substituted C1-8 alkyl group, an unsubstituted or $G^1$-substituted C2-6 alkenyl group, an unsubstituted or $G^1$-substituted C2-6 alkynyl group, a hydroxyl group, an unsubstituted or $G^1$-substituted C1-6 alkoxy group, a formyl group, an unsubstituted or $G^1$-substituted C1-6 alkylcarbonyl group, an unsubstituted or $G^1$-substituted C1-6 alkoxycarbonyl group, a formyloxy group, an unsubstituted or $G^1$-substituted C1-6 alkylcarbonyloxy group, a formylamino group, an unsubstituted or $G^{21}$-substituted mono C1-6 alkylcarbonylamino group, an unsubstituted or $G^1$-substituted N—(C1-6 alkylcarbonyl)-N—(C1-6 alkyl) amino group, an unsubstituted or $G^1$-substituted N—(C1-6 alkylcarbonyl)-N—(C1-6 alkoxycarbonyl) amino group, an unsubstituted or $G^1$-substituted C1-6 alkoxycarbonyloxy group, an unsubstituted or $G^{21}$-substituted mono C1-6 alkoxycarbonylamino group, an unsubstituted or $G^{22}$-substituted C3-8 cycloalkyl group, an unsubstituted or $G^{22}$-substituted C3-8 cycloalkenyl group, an unsubstituted or $G^1$-substituted C 3-8 cycloalkylcarbonylaminocarbonyl group, an unsubstituted or $G^{22}$-substituted C6-10 aryl group, an unsubstituted or $G^{22}$-substituted C6-10 aryl C2-6 alkynyl group, an unsubstituted or $G^{22}$-substituted C6-10 aryloxy group, an unsubstituted or $G^{22}$-substituted 3- to 10-membered heterocyclyl group, a 13-membered heteroaryl group, an unsubstituted or $G^{22}$-substituted 3- to 10-membered heterocyclyloxy group, a mercapto group, an unsubstituted or $G^1$-substituted C1-6 alkylthio group, an unsubstituted or $G^1$-substituted C1-6 alkylsulfinyl group, an unsubstituted or $G^1$-substituted C1-6 alkylsulfonyl group, a pentafluorosulfanyl group, an unsubstituted or $G^{22}$-substituted unsubstituted C6-10 arylthio group, an unsubstituted or $G^{22}$-substituted C6-10 arylsulfinyl group, an unsubstituted or $G^{22}$-substituted C6-10 arylsulfonyl group, an unsubstituted or $G^{22}$-substituted monovalent C6-10 arylamino group, a dihydroboryl group, a nitro group, a cyano group, a halogeno group, an unsubstituted or $G^1$-substituted C1-6 alkylene group, an unsubstituted or $G^1$-substituted C1-6 alkylene monooxy group, an unsubstituted or $G^{21}$-substituted C1-6 alkylenedioxy group, a group represented by —$CR^a$=$NR^b$, here, $R^a$ represents a hydrogen atom, a C1-6 alkyl group, an unsubstituted or $G^{21}$-substituted mono C1-6 alkylcarbonylamino group, or an unsubstituted or $G^{22}$-substituted mono C 3-8 cycloalkylcarbonylamino group, $R^b$ represents an unsubstituted or $G^{21}$-substituted C1-6 alkoxy group, an unsubstituted or $G^{22}$-substituted C3-8 cycloalkoxy group, an unsubstituted or $G^{22}$-substituted phenoxy group, an unsubstituted or $G^{21}$-substituted mono C1-6 alkylamino group, or an unsubstituted or $G^{21}$-substituted di C1-6 alkylamino group, when there are two or more $G^2$-substituted groups, such $G^2$s may be the same as or different from each other, $G^{21}$ represents a C1-6 alkoxy group, a C1-6 haloalkoxy group, a mono C1-6 alkylamino group, a di C1-6 alkylamino group, a mono (C1-6 alkoxy C1-6 alkylcarbonyl) amino group, an unsubstituted or $G^{211}$-substituted C6-10 aryl group, an unsubstituted or $G^{211}$-substituted C6-10 aryloxy group, an unsubstituted or $G^{211}$-substituted 3- to 10-membered heterocyclyl group, an unsubstituted or $G^{211}$-substituted 3- to 10-membered heterocyclyloxy group or a halogeno group, when there are two or more $G^{21}$-substituted groups, such $G^{21}$s may be the same as or different from each other, $G^{211}$ represents a C1-6 alkyl group, a C1-6 haloalkyl group, a C1-6 alkoxy group, a C1-6 haloalkoxy group or a halogeno group, when there are two or more $G^{211}$-substituted groups, such $G^{211}$s may be the same as or different from each other, $G^{22}$ represents an unsubstituted or hydroxyl-substituted C1-6 alkyl group, a C1-6 haloalkyl group, a C2-6 alkenyl group, a C2-6 haloalkenyl group, a C2-6 alkynyl group, a C1-6 alkoxy group, a C1-6 haloalkoxy group, a C1-6 alkylcarbonyl group, a mono C1-6 alkylamino group, a di C1-6 alkylamino group, a C1-6 alkylaminocarbonyl group, a C1-6 alkylthio group, a C1-6 haloalkylthio group, a C1-6 alkylsulfinyl group, a C1-6 haloalkylsulfinyl group, a C1-6 alkylsulfonyl group, a C1-6 haloalkylsulfonyl group, an unsubstituted or $G^{221}$-substituted C3-8 cycloalkyl group, an unsubstituted or $G^{221}$-substituted C3-8 cycloalkyl C1-6 alkyl group, an unsubstituted or $G^{221}$-substituted C 6-10 aryl group, an unsubstituted or $G^{221}$-substituted 3- to 10-membered heterocyclyl group, an unsubstituted or $G^{221}$-substituted 3- to 10-membered heterocyclylcarbonyl group, a pentafluorosulfanyl group, a nitro group, a cyano group, a halogeno group, an oxo group, an unsubstituted or $G^{211}$-substituted C1-6 alkylenedioxy group or a group represented by —$CR^c$=$NOR^d$, here, $R^c$ represents a C1-6 alkyl group, $R^d$ represents an unsubstituted or $G^{221}$-substituted C3-8 cycloalkyl group, when there are two or more $G^{22}$-substituted groups, such $G^{22}$s may be the same as or different from each other, $G^{221}$ represents a C1-6 alkyl group, a C1-6 haloalkyl group, a C1-6 alkoxy group, a C1-6 haloalkoxy group, a mono C1-6 alkylamino group, a di C1-6 alkylamino group, a C6-10 aryl group or a halogeno group, when there are two or more $G^{221}$-substituted groups, such $G^{221}$'s may be the same as or different from each other.

2. An agricultural and horticultural fungicide comprising as an active ingredient at least one selected from the group consisting of the pyridine compound, the N-oxide compound thereof, and the tautomer and salt thereof according to claim 1.

3. A harmful organism control agent comprising as an active ingredient at least one selected from the group consisting of the pyridine compound, the N-oxide compound thereof, and the tautomer and salt thereof according to claim 1.

* * * * *